(12) United States Patent
Klein et al.

(10) Patent No.: US 11,077,266 B2
(45) Date of Patent: Aug. 3, 2021

(54) METHOD AND APPARATUS TO ATTAIN AND MAINTAIN TARGET ARTERIAL BLOOD GAS CONCENTRATIONS USING RAMP SEQUENCES

(71) Applicant: THORNHILL SCIENTIFIC INC., Toronto (CA)

(72) Inventors: Michael Klein, Toronto (CA); Joseph Fisher, Thornhill (CA); James Duffin, Toronto (CA); Marat Slessarev, Toronto (CA); Cathie Kessler, Toronto (CA); Shoji Ito, Toronto (CA); Olivia Sobczyk, Etobicoke (CA); Anne Battisti-Charbonney, Trois-Rivieres (CA); Daniel Michael Mandell, Toronto (CA)

(73) Assignee: THORNHILL SCIENTIFIC INC., Toronto (CA)

( * ) Notice: Subject to any disclaimer, the term of this patent is extended or adjusted under 35 U.S.C. 154(b) by 416 days.

(21) Appl. No.: 15/904,235

(22) Filed: Feb. 23, 2018

(65) Prior Publication Data

US 2018/0311454 A1 Nov. 1, 2018

Related U.S. Application Data

(63) Continuation of application No. 14/398,034, filed as application No. PCT/CA2013/000427 on Apr. 30, 2013, now abandoned.
(Continued)

(51) Int. Cl.
*A61M 16/00* (2006.01)
*A61M 16/12* (2006.01)
(Continued)

(52) U.S. Cl.
CPC .... *A61M 16/0066* (2013.01); *A61M 16/0045* (2013.01); *A61M 16/026* (2017.08);
(Continued)

(58) Field of Classification Search
CPC .......... A61M 16/0066; A61M 16/1005; A61M 16/122; A61M 16/026; A61M 16/0045;
(Continued)

(56) References Cited

U.S. PATENT DOCUMENTS

| 4,463,764 A | * | 8/1984 | Anderson | ............... A61B 5/222 600/532 |
| 4,986,268 A | * | 1/1991 | Tehrani | ............... A61M 16/024 128/204.22 |

(Continued)

FOREIGN PATENT DOCUMENTS

| EP | 1189649 B1 | 6/2005 |
| EP | 2098163 A1 | 9/2009 |

(Continued)

OTHER PUBLICATIONS

CIPO, Examination Report, dated Feb. 27, 2019, re Canadian Patent Application No. 2872055.
(Continued)

*Primary Examiner* — Kendra D Carter
*Assistant Examiner* — Jonathan S Paciorek
(74) *Attorney, Agent, or Firm* — Perry + Currier Inc.

(57) ABSTRACT

An apparatus and method for controlling the end tidal partial pressure of a gas X in a subject's lung, and to the use of such an apparatus and method for research, diagnostic and therapeutic purposes, wherein the method consists of: —obtaining input of a series of logistically attainable PetX values for a series of respective breaths: —determining an amount of gas X required to be inspired by the subject in an inspired gas to target the PetX for each of said respective breaths:
(Continued)

Overall system and—controlling a gas delivery device to deliver the amount of gas in a volume of gas delivered to the subject in each of said respective breaths to target the respective PetX for that breath.

19 Claims, 16 Drawing Sheets

Related U.S. Application Data

(60) Provisional application No. 61/640,570, filed on Apr. 30, 2012.

(51) Int. Cl.
*A61M 16/10* (2006.01)
*A61B 5/08* (2006.01)
*A61B 5/091* (2006.01)

(52) U.S. Cl.
CPC ........ *A61M 16/1005* (2014.02); *A61M 16/12* (2013.01); *A61M 16/122* (2014.02); *A61B 5/082* (2013.01); *A61B 5/091* (2013.01); *A61M 2016/0027* (2013.01); *A61M 2016/0036* (2013.01); *A61M 2016/103* (2013.01); *A61M 2016/1025* (2013.01); *A61M 2202/0208* (2013.01); *A61M 2202/0225* (2013.01); *A61M 2205/3303* (2013.01); *A61M 2205/502* (2013.01); *A61M 2205/52* (2013.01); *A61M 2230/04* (2013.01); *A61M 2230/202* (2013.01); *A61M 2230/205* (2013.01); *A61M 2230/208* (2013.01); *A61M 2230/432* (2013.01); *A61M 2230/435* (2013.01)

(58) Field of Classification Search
CPC .......... A61M 16/12; A61M 2016/0027; A61M 2016/0036; A61M 2016/1025; A61M 2016/103; A61M 2202/0208; A61M 2202/0225; A61M 2205/3303; A61M 2205/502; A61M 2205/52; A61M 2230/04; A61M 2230/202; A61M 2230/205; A61M 2230/208; A61M 2230/432; A61M 2230/435; A61B 5/082; A61B 5/091

See application file for complete search history.

(56) References Cited

U.S. PATENT DOCUMENTS

| | | | |
|---|---|---|---|
| 6,217,524 B1 * | 4/2001 | Orr | A61B 5/0836 128/204.12 |
| 2001/0029339 A1 | 10/2001 | Orr et al. | |
| 2003/0167016 A1 * | 9/2003 | Mault | A61B 5/029 600/529 |
| 2005/0217671 A1 * | 10/2005 | Fisher | A61B 5/083 128/204.18 |
| 2008/0230061 A1 | 9/2008 | Tham | |
| 2009/0120435 A1 * | 5/2009 | Slessarev | A61M 16/12 128/203.14 |
| 2012/0215124 A1 | 8/2012 | Fisher et al. | |
| 2013/0109978 A1 | 5/2013 | Fisher et al. | |

FOREIGN PATENT DOCUMENTS

| | | |
|---|---|---|
| WO | WO-2007012197 A1 | 2/2007 |
| WO | WO-2011143751 A1 | 11/2011 |
| WO | WO-2012139204 A1 | 10/2012 |
| WO | WO-2013082703 A1 | 6/2013 |
| WO | WO-2013138910 A1 | 9/2013 |

OTHER PUBLICATIONS

EPO, Extended European Search Report, dated Nov. 26, 2015, re European Patent Application No. 13784953.5.
ISA/CA, International Search Report and Written Opinion, dated Jul. 30, 2013 re PCT International Patent Application No. PCT/CA2013/000427.
Slessarev et al.; "Prospective targeting and control of end-tidal CO2 and O2 concentrations"; Department of Physiology; p. 1207-1219; Apr. 5, 2007.
EPO, Communication pursuant to Article 93(4) EPC, dated Mar. 6, 2020, re European Patent Application No. 13784953.5.
CIPO, Examination Report, dated Mar. 31, 2020, re Canadian Patent Application No. 2872055.

* cited by examiner

Overall system**

The Tissues**

$$P_{ET}X[i]^T = \frac{\overbrace{P_{ET}X[i-1]^T \cdot FRC}^{\text{gas X in FRC}} + \overbrace{P_{ET}X[i-1]^T \cdot V_D}^{\substack{\text{gas X re-inspired} \\ \text{from } V_D}} + \overbrace{P_I X[i] \cdot (V_T - V_D)}^{\substack{\text{gas X in controlled} \\ \text{gas mixture}}} + \overbrace{PB \cdot Q \cdot (1-s) \cdot T_B \cdot (C_{MV}X[i] - C_p X[i])}^{\substack{\text{gas X transfered into lung from} \\ \text{the circulation (VB}_X)}}}{\underbrace{V_T + FRC}_{\text{Total volume of the alveolar space}}}$$

**Figure 3
Lung No SGD**

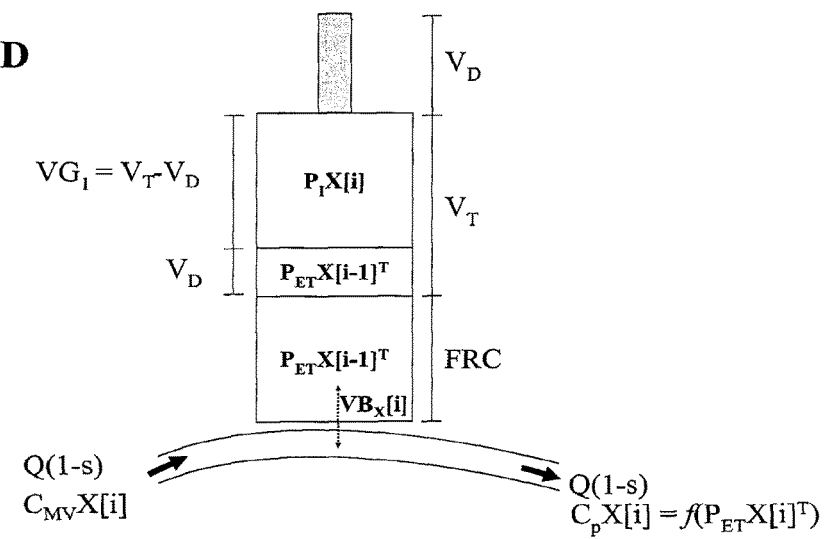

Lung SGD

Figure 5 Apparatus

Tuning**

Figure 7

Definitions of abbreviated terms

| Term | Units | Definition |
|---|---|---|
| $n$ | | Total number of breaths in the target sequence |
| $i$ | | Index of breath number in the target sequence |
| $P_{ET}O2[i]^T$ | mmHg | Target end-tidal partial pressure of O2 during breath $i$ |
| $P_{ET}CO2[i]^T$ | mmHg | Target end-tidal partial pressure of CO2 during breath $i$ |
| $P_{ET}O2[i]^M$ | mmHg | Measured end-tidal partial pressure of O2 during breath $i$ |
| $P_{ET}CO2[i]^M$ | mmHg | Measured end-tidal partial pressure of CO2 during breath $i$ |
| $pH[i]$ | | pH of pulmonary end-capillary blood during breath $i$ |
| $[HCO_3]$ | mmol/L | Bicarbonate concentration of the blood throughout the circulation |
| $P_pO2[i]$ | mmHg | Partial pressure of O2 in the pulmonary end-capillary blood during breath $i$ |
| $P_pCO2[i]$ | mmHg | Partial pressure of CO2 in the pulmonary end-capillary blood during breath $i$ |
| $T$ | C | Body temperature |
| $S_pO2[i]$ | % | O2 saturation of the pulmonary end-capillary blood during breath $i$ |
| $Hb$ | g/dL | Concentration of haemoglobin in the blood throughout the circulation |
| $C_pO2[i]$ | ml/dL | O2 content of the pulmonary end-capillary blood during breath $i$ |
| $C_pCO2[i]$ | ml/dL | CO2 content of the pulmonary end-capillary blood during breath $i$ |

Figure 7 – (continued)

| | | |
|---|---|---|
| $C_aO2[i]$ | ml/dL | O2 content of the arterial blood during breath $i$ |
| $C_aCO2[i]$ | ml/dL | CO2 content of the arterial blood during breath $i$ |
| $C_{MV(T)}O2[i]$ | ml/dL | O2 content of the mixed-venous blood leaving the tissues during breath $i$ |
| $C_{MV(T)}CO2[i]$ | ml/dL | CO2 content of the mixed-venous blood leaving the tissues during breath $i$ |
| $C_{MV}O2[i]$ | ml/dL | O2 content of the mixed-venous blood entering the pulmonary circulation during breath $i$ |
| $C_{MV}CO2[i]$ | ml/dL | CO2 content of the mixed-venous blood entering the pulmonary circulation during during breath $i$ |
| $s$ | %/100 | Intrapulmonary shunt fraction |
| $Q$ | dL/min | Cardiac output |
| $T_B$ | min | Breath period |
| $VO2$ | ml/min | Overall metabolic consumption of O2 |
| $VCO2$ | ml/min | Overall metabolic production of CO2 |
| $n_{O2}$ | | Total number of compartments in the model of O2 in the tissues |
| $j$ | | Index of the compartments in the model of O2 in the tissues |
| $vo2_j$ | %/100 | Fraction of the overall metabolic consumption of O2 assigned to compartment $j$ of the model of O2 in the tissues |
| $q_j$ | %/100 | Fraction of the overall cardiac output assigned to compartment $j$ of the model of O2 in the tissues |
| $dO2_j$ | ml | Storage capacity for O2 of compartment $j$ of the model of |

Figure 7 – (continued)

| | | |
|---|---|---|
| | | O2 in the tissues |
| $n_{CO2}$ | | Total number of compartments in the model of CO2 in the tissues |
| $k$ | | Index of the compartments in the model of CO2 in the tissues |
| $vco2_k$ | %/100 | Fraction of the overall metabolic production of CO2 assigned to compartment $k$ of the model of CO2 in the tissues |
| $q_k$ | %/100 | Fraction of the overall cardiac output assigned to compartment $k$ of the model of CO2 in the tissues |
| $dCO2_k$ | ml | Storage capacity for CO2 of compartment $k$ of the model of CO2 in the tissues |
| SGDC | | Sequential gas delivery circuit |
| PT | | Pressure transducer |
| GA | | O2/CO2 gas analyzer |
| DX | | Display |
| CPU | | Computer |
| ID | | Input device |
| GB | | Gas blender |
| FT | | Flow transducer |
| $G_1$ | | The controlled gas mixture inspired by the subject |

Figure 7 – (continued)

| | | |
|---|---|---|
| $G_2$ | | Neutral gas inspired by the subject |
| $FG_1$ | ml/min | Rate at which the controlled gas mixture ($G_1$) is made available for inspiration |
| $VG_1$ | ml | Average volume of the controlled gas mixture ($G_1$) inspired into the alveoli per breath |
| $VG_2$ | ml | Average volume of neutral gas ($G_2$) inspired into the alveoli per breath |
| $V_T$ | ml | Tidal volume |
| $V_D$ | ml | Anatomical dead space |
| $P_IO2[i]$ | mmHg | Partial pressure of O2 in the controlled gas mixture ($G_1$) during breath $i$ |
| $P_ICO2[i]$ | mmHg | Partial pressure of CO2 in the controlled gas mixture ($G_1$) during breath $i$ |
| $F_IO2[i]$ | %/100 | Fractional concentration of O2 in the controlled gas mixture ($G_1$) during breath $i$ |
| $F_ICO2[i]$ | %/100 | Fractional concentration of CO2 in the controlled gas mixture ($G_1$) during breath $i$ |
| $FRC$ | ml | Functional residual capacity |
| $W$ | kg | Subject weight |
| $H$ | m | Subject height |
| $A$ | years | Subject age |
| $G$ | male/female | Subject sex |
| $n_R$ | # breaths | Recirculation time |

Figure 7 – (continued)

| | | |
|---|---|---|
| $PB$ | mmHg | Barometric pressure |
| $n_{SG}$ | | Total number of source gases blended to create the controlled gas mixture |
| $m$ | | Index of source gases blended to create the controlled gas mixture |
| $SG_m$ | | Source gas $m$ blended to create the controlled gas mixture |
| $FSG_m[i]$ | ml/min | Flow rate of source gas $m$ ($SG_m$) during breath $i$ |
| $fo2_m$ | %/100 | Fractional concentration of O2 in source gas $m$ ($SG_m$) |
| $fco2_m$ | %/100 | Fractional concentration of CO2 in source gas $m$ ($SG_m$) |
| $P_{ET}O2_0^M$ | mmHg | Baseline/resting measured end-tidal partial pressure of O2 |
| $P_{ET}CO2_0^M$ | mmHg | Baseline/resting measured end-tidal partial pressure CO2 |
| $VB_{O2}[i]$ | ml | The volume of O2 transferred between the alveolar space and the pulmonary circulation during breath $i$ |
| $VB_{CO2}[i]$ | ml | The volume of CO2 transferred between the alveolar space and the pulmonary circulation during breath $i$ |
| $\alpha$ | ml/mmHg | Correction factor for tuning the estimate of the functional residual capacity ($FRC$) |
| $\beta$ | ml/min/mmHg | Correction factor for tuning the overall metabolic production of O2 ($VO2$) |
| $\gamma$ | ml/min/mmHg | Correction factor for tuning the overall metabolic consumption of CO2 ($VCO2$) |

Table 2

| Starting PCO2 (mm Hg) | 1st Baseline (40mmHg) | 1st Step (50mmHg) | 2nd baseline (40mmHg) | 2nd Step (50mmHg) | 3rd baseline (40mmHg) | Delta PCO2 First step | Delta PCO2 Second Step |
|---|---|---|---|---|---|---|---|
| 40 | 40 | 50 | 41 | 50 | 40 | 10 | 9 |
| 39 | 39 | 49 | 40 | 49 | 40 | 10 | 9 |
| 41 | 41 | 49 | 42 | 50 | 41 | 8 | 8 |
| 40 | 39 | 48.5 | 40 | 49 | 40 | 9 | 9 |
| 35 | 39 | 48 | 40 | 48 | 40 | 9 | 8 |
| 40 | 39 | 48 | 39 | 49 | 40 | 9 | 10 |

Figure 11

METHOD AND APPARATUS TO ATTAIN AND MAINTAIN TARGET ARTERIAL BLOOD GAS CONCENTRATIONS USING RAMP SEQUENCES

FIELD OF THE INVENTION

The present invention relates to an apparatus and method for controlling end tidal gas partial pressures in spontaneously breathing or ventilated subjects and to the use of such an apparatus and method for research, diagnostic and therapeutic purposes.

BACKGROUND OF THE INVENTION

Techniques for controlling end-tidal partial pressures of carbon dioxide, oxygen and other gases are gaining increasing importance for a variety of research, diagnostic and medicinal purposes. Methods for controlling end tidal pressures of gases have gained particular importance as a means for manipulating arterial levels of carbon dioxide (and also oxygen), for example to provide a controlled vasoactive stimulus to enable the measurement of cerebrovascular reactivity (CVR) e.g. by MRI.

Conventional methods of manipulating arterial carbon dioxide levels such as breath holding, hyperventilation and inhalation of fixed concentration of carbon dioxide balanced with medical air or oxygen are deficient in their ability to rapidly and accurately attain targeted arterial carbon dioxide partial pressures for the purposes of routinely measuring vascular reactivity in a rapid and reliable manner.

The end-tidal partial pressures of gases are determined by the gases inspired into the lungs, the mixed venous partial pressures of gases in the pulmonary circulation, and the exchange of gases between the alveolar space and the blood in transit through the pulmonary capillaries. Changes in the end-tidal partial pressures of gases are reflected in the pulmonary end-capillary partial pressures of gases, which in turn flow into the arterial circulation. The gases in the mixed-venous blood are determined by the arterial inflow of gases to the tissues and the exchange of gases between the tissue stores and the blood, while the blood is in transit through the tissue capillary beds.

Robust control of the end-tidal partial pressures of gases therefore requires precise determination of the gas storage, transport, and exchange dynamics at the lungs and throughout the body. Previous attempts at controlling the end-tidal partial pressures of gases have failed to account for these complex dynamics, and have therefore produced mediocre results.

In the simplest approaches, manipulation of the end-tidal partial pressures of gases has been attempted with fixed changes to the composition of the inspired gas. However, without any additional intervention, the end-tidal partial pressures of gases vary slowly and irregularly as exchange occurs at the lungs and tissues. Furthermore, the ventilatory response to perturbations in the end-tidal partial pressures of gases is generally unpredictable and potentially unstable. Often, the ventilatory response acts to restore the condition of the blood to homeostatic norms. Therefore, any changes in the end-tidal partial pressures of gases are immediately challenged by a disruptive response in the alveolar ventilation. Consequently, fixed changes in the inspired gas composition provoke only slow, irregular, and transient changes in blood gas partial pressures.

In more complex approaches, manipulation of the end-tidal partial pressures of gases has been attempted with negative feedback control. These approaches continuously vary the composition of the inspired gas so as to minimize error between measured and desired end-tidal partial pressures of gases. Technically, such a system suffers from the same limitations as all negative feedback control systems—an inherent trade-off between response time and stability.

Consequently, there is a need to overcome previous limitations in end-tidal gas control, allowing for more precise and rapid execution of end tidal gas targeting sequences in a wide range of subjects and environments.

SUMMARY OF INVENTION

According to one aspect the invention is directed to a method of controlling an amount of at least one gas X in a subject's lung to attain at least one targeted end tidal partial pressure of the at least one gas X, comprising the steps of:

a. Obtaining input of a logistically attainable end tidal partial pressure of gas X ($PetX[i]^T$) for one or more respective breaths [i];

b. Obtaining input of a prospective computation of an amount of gas X required to be inspired by the subject in an inspired gas to target the $PetX[i]^T$ for a respective breath [i] using inputs required to compute a mass balance equation, wherein one or more values required to control the amount of gas X in a volume of gas delivered to the subject is output from the mass balance equation; and optionally c. Controlling the amount gas X in a volume of gas delivered to the subject in a respective breath [i] to target the respective $PetX[i]^T$ based on the prospective computation.

For present purposes a mass balance equation is understood to be a mathematical relationship that applies the law of conservation of mass (i.e. the amount of at least one gas X) to the analysis of movement of at least one gas X, in and out of the lung, for the purpose of prospectively targeting an end tidal partial pressure of gas X. Optionally, where an end tidal partial pressure of gas X is sought to be changed from a baseline steady state value or controlled for a sequence of respective breaths [i] the mass balance equation will account for the transfer of a mass of gas X between a subject's lung and pulmonary circulation (i.e. the mixed venous blood entering the pulmonary capillaries ($C_{MV}X[i]$)); so that this key source of flux affecting the end tidal partial pressure of gas X in the breath(s) of interest, is accounted for.

Preferably the mass balance equation is computed based on a tidal model of the lung as described hereafter.

In one embodiment of the method, a concentration of gas X ($F_IX$), for example in a first inspired gas (the first inspired gas also referred to, in one embodiment of the invention, as a controlled gas mixture) is computed to target or attain $PetX[i]^T$ in a respective breath [i].

Optionally, the mass balance equation is solved for $F_IX$.

It will be appreciated that $F_IX$ may be output from the mass balance equation by testing iterations of its value without directly solving for $F_IX$.

Optionally, the volume of gas delivered to the subject is a fixed tidal volume controlled by a ventilator.

Optionally, the volume of gas delivered to the subject in a respective breath [i] comprises a first inspired gas of known volume and a second inspired neutral gas.

In accordance with a tidal model of the lung, in one embodiment of the invention, the mass balance equation is computed in terms of discrete respective breaths [i] including one or more discrete volumes corresponding to a subject's FRC, anatomic dead space, a volume of gas transferred between the subject's lung and pulmonary circulation in the respective breath [i] and an individual tidal volume of the respective breath [i].

According to another aspect, the invention is directed to a method of controlling an amount of at least one gas X in a subject's lung to attain a targeted end tidal partial pressure of the at least one gas X, comprising the steps of:
a. Obtaining input of a concentration of gas X in the mixed venous blood entering the subject's pulmonary circulation for gas exchange in one or more respective breaths [i] ($C_{MV}X[i]$);
b. Obtaining input of a logistically attainable end tidal partial pressure of gas X ($PetX[i]^T$) for a respective breath [i];
c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and optionally
d. Controlling the amount gas X in a volume of gas delivered to the subject in a respective breath [i] to target the respective $PetX[i]^T$ based on the prospective computation.

In one embodiment of the method, a concentration of gas X ($F_IX$) is computed to target or attain $PetX[i]^T$ in a respective breath [i].

Optionally, the mass balance equation is solved for $F_IX$.

According to one embodiment of the method, the mass balance equation is computed based on a tidal model of the lung.

In accordance with a tidal model of the lung, in one embodiment of the invention, the mass balance equation is computed in terms of discrete respective breaths [i] including one or more discrete volumes corresponding to a subject's FRC, anatomic dead space, a volume of gas transferred between the subject's lung and pulmonary circulation in the respective breath [i] and an individual tidal volume of the respective breath [i].

According to another embodiment of the method, the method comprises the step of tuning one or more inputs required for computation of $F_IX$, for example, with respect to any terms and/or by any methods described in this application.

According to another embodiment of the method, the volume of inspired gas entering the subject's alveoli is controlled by fixing a tidal volume of an inspired gas containing gas X using a ventilator and subtracting a volume of gas corresponding to an estimated or measured value for the subject's anatomic dead space volume.

According to another embodiment of the method, the gas inspired by the subject is inspired via a sequential gas delivery circuit (as defined below). Optionally, the rate of flow of gas into the sequential gas delivery circuit is used to compute the volume of inspired gas entering the subject's alveoli in a respective breath [i].

According to one aspect of the method, the gas inspired by the subject in each respective breath [i] comprises a first inspired gas and a second inspired optionally neutral gas, wherein the first inspired gas is delivered in the first part of a respective breath [i] followed by a second inspired neutral gas for the remainder of the respective breath [i], the volume of the first inspired gas selected so that intake of the second inspired neutral gas at least fills the entirety of the anatomic dead space. $F_IX$ is computed prospectively from a mass balance equation expressed in terms which correspond to all or an application-specific subset of the terms in equation 1 and the first inspired gas has a concentration of gas X which corresponds to $F_IX$ for the respective breath [i]

A "tidal model of the lung" means any model of the movement of gases into and out of the lung that acknowledges that inspiration of gas into, and the expiration of gas from the lung, occurs in distinct phases, each inspiration-expiration cycle comprising a discrete breath, and that gases are inspired in to, and expired from, the lungs via the same conduit.

In terms of computing a mass balance equation and capturing relevant aspects of movement of gases into and out of the lung, a tidal model of lung is preferably understood to yield a value of $F_IX$ on a breath by breath basis from a mass balance equation. The mass balance equation is computed in terms of discrete respective breaths [i] including one or more discrete volumes corresponding to a subject's FRC, anatomic dead space, a volume of gas transferred between the subject's lung and pulmonary circulation in the respective breath [i] and an individual tidal volume of the respective breath [i]. Optionally, the mass balance equation is solved for $F_IX$.

Preferably for optimal accuracy in a universal set of circumstances, all these discrete volumes are accounted for in the mass balance equation. However, it is possible for the invention to be exploited sub-optimally or for individual circumstances in which the relative sizes of certain of these respective volumes (e.g. anatomic dead space, volume of gas X transferred between the pulmonary circulation and lung and even tidal volume (shallow breaths) may be relatively small (compared to other volumes) depending on the circumstances and hence failing to account for all of these volumes may affect achievement of a target end tidal partial pressure to an acceptable extent particularly where less accuracy is demanded.

In one embodiment of the invention, the mass balance equation (optionally written in terms of one or more concentration of gas X in one or more discrete volumes of gas):
a. Preferably accounts for the total amount of gas X in the lung following inhalation of the inspired gas in a respective breath [i] ($M_LX[i]$) including transfer of gas X between the lung and the pulmonary circulation;
b. Assumes distribution of $M_LX[i]$ into compartments including the subject's FRC ($M_LX[i]_{FRC}$), a fixed or spontaneously inspired tidal volume ($M_LX[i]_{VT}$) and preferably the subject's anatomic dead space volume ($M_LX[I]_{VD}$);
c. Assumes uniform distribution of the $M_LX[i]_{FRC}$ a and $M_LX[i]_{VT}$ in the cumulative volume $FRC+V_T$;
d. Preferably includes a term that accounts for re-inspiration in a respective breath [i] of an amount of gas X left in the dead space volume after exhalation in a previous breath [i−1].

As detailed below, according to one embodiment, in which the invention is implemented via sequential gas delivery, the individual respective tidal volume for a breath [i] may consist of a first inspired gas having a concentration of gas X corresponding to $F_IX$ and second inspired neutral gas. The volume of the first inspired gas may be fixed, for example by controlling the rate of flow of first inspired gas into a sequential gas delivery circuit.

In one embodiment of the invention the mass balance equation comprises terms corresponding to all or an application-specific subset of the terms in equations 1 or 2 forth below as described hereafter. An "application-specific subset" means a subset tailored to either a minimum, intermediate or logistically optimal standard of accuracy having regard to the medical or diagnostic application of the invention in question or the sequence of $PetX[i]^T$ values targeted. Optional terms and mandatory inclusions in the subset may be considered application-specific as a function of the sequence of $PetX[i]^T$ values targeted in terms of the absolute size of the target value and/or the relative size of the target value going from one breath to the next as discussed below. For example, in most cases, the $O_2$ or $CO_2$ re-inspired from the anatomical dead space ($V_D$) is small compared to the $O_2$ or $CO_2$ in the other volumes that contribute to the end-tidal partial pressures. For example, where the volume of $O_2$ or $CO_2$ in the first inspired gas is very large, in trying to induce a large increase in the target end-tidal partial pressures, the $O_2$ or $CO_2$ transferred into the lung from the circulation may be comparatively small and neglected. Neglecting any terms of the mass balance equations will decrease computational complexity at the expense of the accuracy of the induced end-tidal partial pressures of gases.

The demands of a diagnostic application may be ascertained empirically or from the literature. For example, a measure of short response times of brain blood vessels to hypercapnic stimulus can be determined to require a square wave change in the stimulus such as a change of 10 mmHg $P_{ET}CO_2$ from one breath to the next. Another example is when measuring response of BOLD signal with MRI to changes in partial pressure of $CO_2$ in the blood, the changes needed may be determined to be abrupt as the BOLD signal has considerable random drift over time.

Optionally, one or more inputs for computation of $PetX[i]^T$ are "tuned" as defined below to adjust, as necessary or desirable, estimated or measured values for FRC and/or total metabolic production/consumption of gas X so as to reduce the discrepancy between targeted and measured end tidal partial pressures of gas X i.e. an actual value, optionally measured at the mouth. Tuning can be done when a measured baseline steady state value of PetX[i] is defined for a series of test breaths.

According to another aspect, the present invention is directed to an apparatus for controlling an amount of at least one gas X in a subject's lung to attain a targeted end tidal partial pressure of the at least one gas X, comprising:
(1) a gas delivery device;
(2) a control system for controlling the gas delivery device including means for:
  a. Obtaining input of a concentration of gas X in the mixed venous blood entering the subject's pulmonary circulation for gas exchange in one or more respective breaths [i] ($C_{MV}X[i]$);
  b. Obtaining input of a logistically attainable end tidal partial pressure of gas X ($PetX[i]^T$) for a respective breath [i];
  c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and
  d. Controlling the amount of gas X in a volume of gas delivered to the subject in a respective breath [i] to target the respective $PetX[i]^T$ based on the prospective computation.

In one embodiment of the method, a concentration of gas X ($F_IX$) is computed to target or attain $PetX[i]^T$ in a respective breath [i].

Optionally, the mass balance equation is solved for $F_IX$.

It will be appreciated the control system may implement one or more embodiments of the method described herein.

In one embodiment of the apparatus the gas delivery device is a sequential gas delivery device.

In one embodiment of the apparatus, the control system is implemented by a computer.

In one embodiment of the apparatus, the computer provides output signals to one or more rapid flow controllers.

In one embodiment of the apparatus, the apparatus is connected to a sequential gas delivery circuit.

In one embodiment of the apparatus, the computer receives input from a gas analyzer and an input device adapted for providing input of one or more logistically attainable target end tidal partial pressure of gas X ($PetX[i]^T$) for a series of respective breaths [i].

In one embodiment of the apparatus, the control system, in each respective breath [i], controls the delivery of at least a first inspired gas and wherein delivery of the first inspired gas is coordinated with delivery a second inspired neutral gas, wherein a selected volume of the first inspired gas is delivered in the first part of a respective breath [i] followed by the second inspired neutral gas for the remainder of the respective breath [i], wherein volume of the first inspired gas is fixed or selected for one or more sequential breaths by way of user input so that intake of the second inspired neutral gas at least fill the entirety of the anatomic dead space.

In one embodiment of the apparatus, the apparatus is connected to a sequential gas delivery circuit.

In one embodiment of the apparatus, the gas delivery device is a gas blender.

In one embodiment of the apparatus, the control system implements program code stored in a computer readable memory or comprises a signal processor embodied in one or more programmable IC chips.

According to another aspect, the present invention is directed to a computer program product for use in conjunction with a gas delivery device to control an amount of at least one gas X in a subject's lung to attain a target end tidal partial pressure of a gas X in the subject's lung, comprising program code for:
  a. Obtaining input of a concentration of gas X in the mixed venous blood entering the subject's pulmonary circulation for gas exchange in one or more respective breaths [i] ($C_{MV}X[i]$);
  b. Obtaining input of a logistically attainable end tidal partial pressure of gas X ($PetX[i]^T$) for a respective breath [i];
  c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and
  d. Controlling the amount in a volume of gas delivered to the subject in a respective breath [i] to target the respective $PetX[i]^T$ based on the prospective computation.

In one embodiment of the method, a concentration of gas X ($F_IX$) is computed to target or attain $PetX[i]^T$ in a respective breath [i].

Optionally, the mass balance equation is solved for $F_IX$.

It will be appreciated the computer program product may be used in conjunction with a gas delivery device, to at least partially implement a control system for carrying out one or more embodiments of the method described herein.

The program code may be stored in a computer readable memory or embodied in one or more programmable IC chips.

The present invention is also directed to the use of an aforementioned method, apparatus or computer program product to:
  a) Provide a controlled vasoactive stimulus for measurement of vascular reactivity;
  b) Provide a controlled vasoactive stimulus for measurement of cerebrovascular reactivity;
  c) Provide a controlled vasoactive stimulus for measurement of liver, kidney, heart or eye vascular reactivity; or
  d) Simultaneously change the subject's end tidal partial pressures of oxygen and carbon dioxide to selected values, for example to potentiate a diagnosis or treat cancer.

According to another aspect, the present invention is directed to a method of controlling an amount of at least one gas X in a subject's lung to attain a targeted end tidal partial pressure of the at least one gas X, comprising the steps of:
  a. Obtaining input of a concentration of gas X in the mixed venous blood entering the subject's pulmonary circulation for gas exchange in one or more respective breaths [i] ($C_{MV}X[I]$);
  b. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation, the mass balance equation comprising terms corresponding to all or an application-specific subset of the terms set forth in:

$$F_I X[i] = \frac{(P_{ET}X[i]^T - P_{ET}X[i-1]^T) \cdot (FRC + V_T) + P_{ET}X[i-1]^T \cdot (FG_1 \cdot T_B) - PB \cdot Q \cdot (1-s) \cdot T_B \cdot (C_{MV}X[i] - C_P X[i])}{FG_1 \cdot T_B \cdot PB} \quad \text{eq. 1}$$

$$F_I X[i] = \frac{P_{ET}X[i]^T \cdot (FRC + V_T) - P_{ET}X[i-1]^T \cdot (FRC + V_D) - PB \cdot Q \cdot (1-s) \cdot T_B \cdot (C_{MV}X[i] - C_P X[i])}{(V_T - V_D) \cdot PB} \quad \text{eq. 2}$$

c. Controlling the amount of gas X in a volume of gas delivered to the subject in a respective breath [i] to target the respective $PetX[i]^T$ based on the prospective computation.

The terms referred to the equations are defined herein.

In one embodiment of the method, a concentration of gas X ($F_I X$) is computed to target or attain $PetX[i]^T$ in a respective breath [i].

Optionally, the mass balance equation is solved for $F_I X$.

According to one embodiment, the gas inspired by the subject in each respective breath [i] comprises a first inspired gas and a second inspired neutral gas (as define hereafter), wherein a selected volume of the first inspired gas is delivered in the first part of a respective breath [i] followed by a second inspired neutral gas for the remainder of the respective breath [i], the volume of the first inspired gas selected so that intake of the second inspired neutral gas at least fills the entirety of the anatomic dead space.

The verb "target" used with reference to achieving a logistically attainable $PetX[i]^T$ value for a respective breath [i] means "attain" with the relative precision pragmatically demanded by the particular therapeutic or diagnostic application in question or the sequence of targets sought to be attained in both absolute and relative (between contiguous breaths) terms. For example, as discussed below, by "tuning" values for certain inputs into equation 1 or 2 (particularly functional residual capacity and total metabolic consumption or production of gas X) a logistically attainable end tidal partial pressure of gas X could be attained with relative precision in one breath. The logistically attainable $PetX[i]^T$ value could theoretically be attained with a clinically acceptable reduced precision by not tuning those values or foregoing other optimizations, as described herein, for example, by tuning total metabolic production or consumption of gas X without tuning FRC, which would be expected to delay getting to the target value more precisely by several breaths.

For purposes herein, it is understood that limitations of a physiological or other nature may impinge on attaining a $PetX[i]^T$. Given a logistically attainable target for which parameters known to impinge on accuracy, that can be optimized (described herein e.g. tuning FRC and total metabolic consumption/production of gas X) are optimized, we have found that a $PetX[i]^T$ can be considered to be "attained" as a function of the difference between the targeted value and a steady state value measured for an individual. For example, assuming a measurement error of +/−2 mm. of Hg, in the case of $CO_2$, for a $PetX[i]^T$ between 30 and 50 mmHg, a measured $PetCO_2$ value that is within 1 to 3 mm. of Hg of $PetX[i]^T$ can be considered to be "attained". Tuning to an extent that achieves a measured value within this range will serve as an indicator as to whether tuning has been successfully completed or should be continued. However in principle, tuning may be iterated until the difference between the measured and targeted PetX is minimized. However, for a $PetCO_2[i]^T$ between 51 and 65 mmHg, a measured PetX value that is within (i.e +/−) 1 to 5 mm. of Hg of $PetCO_2[i]^T$ can be considered to be "attained" and the success of a given tuning sequence can be judged accordingly.

In the case of oxygen, a measured $PetO_2$ value that is within 5-10% of $PetO_2[i]^T$ can be considered to be one which has "attained" $PetO_2[i]^T$. For example, if the target $PetO_2$ value is between 75 mm of Hg and 150 mm of Hg a range of measured values that proportionately is within (i.e. +/−) 4 mm and 8 mm of Hg (5 and 10% of 75 respectively) to +/−8 mm to 15 mm of Hg (5-10% of 150) can be considered to be attained (similarly for a target of 100 mm of Hg, +/−5-10 mm of Hg; and for a $PetO2[i]^T$ of 200 mm Hg, +/−10-20 mm of Hg).

However, as described above, depending on the demands of the application and the circumstances, a $PetX[i]^T$ can be considered to be "targeted" with a deliberately reduced precision (as opposed to "attained" as a goal) if parameters known to impinge on accuracy, that can be optimized (described herein e.g. tuning FRC and total metabolic consumption/production of gas X) are deliberately not optimized. The invention as defined herein (not to the exclusion of variations apparent to those skilled in the art) is nevertheless exploited inasmuch as various aspects of the invention described herein provide for a prospective targeting system, a system that can be judiciously optimized (or not) to accommodate a variety of circumstances and sub-optimal uses thereof. A $PetX[i]^T$ can be considered to have been "targeted" by exploiting the invention as defined, in one embodiment, after executing a sequence of tuning breaths, wherein the tuning sequence optionally establishes that the optimizations defined herein make the target "attainable".

According to another aspect, the present invention is also directed to a preparatory method for using a gas delivery device to control an amount of at least one gas X in a subject's lung to attain a targeted end tidal partial pressure of the at least one gas X, comprising the step of executing a sequence of "tuning" breaths as described hereafter.

Optionally, one or more inputs for computation of PetX$[i]^T$ are "tuned" as defined below to adjust, as necessary or desirable, estimated or measured values for FRC and/or total metabolic production/consumption of gas X so as to reduce the discrepancy between targeted and measured end tidal partial pressure of gas X i.e. an actual value, optionally measured at the mouth. Tuning is preferably done when a measured baseline steady state value of PetX[i] is ascertained for a series of ensuing test breaths.

According to one embodiment of the invention, an estimated or measured value for the subject's functional residual capacity (FRC) is tuned.

Optionally, FRC is tuned in a series of tuning breaths by:
a. changing the targeted end tidal partial pressure of gas X between a tuning breath [i+x] and a previous tuning breath [i+x−1];
b. comparing the magnitude of the difference between the targeted end tidal partial pressure of gas X for said tuning breaths [i+x] and [i+x−1] with the magnitude of the difference between the measured end tidal partial pressure of gas X for the same tuning breaths to quantify any discrepancy in relative magnitude; and
c. adjusting the value of FRC in proportion to the discrepancy to reduce the discrepancy in any subsequent prospective computation of $F_I X$.

Optionally, FRC is tuned in a series of tuning breaths in which a sequence of end tidal partial pressures of gas X is targeted at least once by:
(a) obtaining input of a measured baseline steady state value for PetX[i] for computing $F_I X$ at start of a sequence;
(b) selecting a target end tidal partial pressure of gas X (PetX$[i]^T$) for at least one tuning breath [i+x] wherein PetX$[i+x]^T$ differs from PetX$[i+x−1]^T$; and
(c) comparing the magnitude of the difference between the targeted end tidal partial pressure of gas X for said tuning breaths [i+x] and [i+x−1] with the magnitude of the difference between the measured end tidal partial pressure of gas X for the same tuning breaths to quantify any discrepancy in relative magnitude;
(d) adjusting the value of FRC in proportion to any discrepancy in magnitude to reduce the discrepancy in a subsequent prospective computation of $F_I X$ including in any subsequent corresponding tuning breaths[i+x−1] and [i+x] forming part of an iteration of the sequence.

According to one embodiment of the invention, an estimated or measured value of the subject's total metabolic production or consumption of gas X is tuned.

Optionally, the total metabolic production or consumption of gas X is tuned in a series of tuning breaths by comparing a targeted end tidal partial pressure of gas X (PetX$[i+x]^T$) for the at least one tuning breath [i+x] with a corresponding measured end tidal partial pressure of gas X for the corresponding breath [i+x] to quantify any discrepancy and adjusting the value of the total metabolic production or consumption of gas X in proportion to any discrepancy to reduce the discrepancy in any subsequent prospective computation of $F_I X$.

Optionally, the total metabolic consumption or production of gas X is tuned in a series of tuning breaths in which a sequence of end tidal partial pressures of gas X is targeted at least once by:
(a) obtaining input of a measured baseline steady state value for PetX[i] for computing $F_I X$ at start of a sequence;
(b) targeting a selected target end tidal partial pressure of gas X (PetX$[i]^T$) for each of a series of tuning breaths [i+1 . . . i+n], wherein PetX$[i]^T$ differs from the baseline steady state value for PetX[i];
(c) comparing the targeted end tidal partial pressure of gas X (PetX$[i+x]^T$) for at least one tuning breath [i+x] in which the targeted end tidal gas concentration of gas X has been achieved without drift in a plurality of prior breaths [1+x−1, 1+x−2 . . . ] with a corresponding measured end tidal partial pressure of gas X for a corresponding breath [i+x] to quantify any discrepancy and adjusting the value of the total metabolic consumption or production of gas X in proportion to the discrepancy to reduce the discrepancy in a subsequent prospective computation of $F_I X$ including in any subsequent corresponding tuning breath [i+x] forming part of an iteration of the sequence.

All key inputs for computing $F_I X$ are itemized below.

We have found that a prospective model which predicts an $F_I X$ that is required to target a logistically attainable end tidal partial pressure of a gas X is simplified and enhanced by using a sequential gas delivery system (alternatively called a sequential gas delivery device, or sequential rebreathing).

According to another embodiment, the apparatus according to the invention is a "sequential gas delivery device" as defined hereafter. The sequential gas delivery device optionally comprises a partial rebreathing circuit or a sequential gas delivery circuit as defined hereafter.

The rate of gas exchange between the subject's mixed venous blood and alveoli for a respective breath [i] may be controlled by providing a partial re-breathing circuit through which the subject inspires a first gas in which the concentration of gas X is $F_I X$ and a second gas having a partial pressure of gas X which is substantially equivalent to the partial pressure of gas X in the subject's end tidal expired gas prior to gas exchange in the current respective breath [i] (the subject's last expired gas which is made available for re-breathing) or a gas formulated in situ to match a concentration of gas X which would have been exhaled in a prior breath. Practically, this may be accomplished by setting the rate of gas flow into the partial rebreathing circuit for a respective breath [i] to be less than the patient's minute ventilation or minute ventilation minus anatomic dead space ventilation (i.e. such that the last inspired second gas at least fills the anatomical dead space if not also part of the alveolar space) and using this rate or the volume of inspired gas it represents in a current breath to compute $F_I X$ for a respective breath [i].

With reference to parameters used to compute terms in equation 1 or 2, it is understood that phrases like "obtaining input" and similar expressions are intended to be understood broadly to encompass, without limitation, input obtained by or provided by an operator of a gas delivery device through any form of suitable hardware input device or via programming or any form of communication or recordation that is translatable into an electronic signal capable of controlling the gas delivery device.

According to another aspect, the invention is also directed to a method of controlling an amount of at least one gas X in a subject's lung to attain, preliminary to or during the course of a diagnostic or therapeutic procedure, at least one target end tidal partial pressure of a gas X.

A PetX[i] attained for any immediately previous breath [i−1] is:
 a. alterable, prospectively, to any other logistically attainable value, in one breath, using a method or apparatus according to the invention;
 b. maintainable, prospectively, without drift, in a respective breath [i] or in breath [i] and in one or more subsequent breaths [i+1] . . . [i+n] using a method or apparatus according to the invention.

According to one embodiment of the invention, a input of a concentration of gas X in the mixed venous blood entering the subject's lung for gas exchange in the respective breath [i]($C_{MV}X[i]$) can be obtained (e.g. predicted) by a compartmental modelling of gas dynamics. "Compartmental modeling of gas dynamics" means a method in which body tissues are modeled as system of one or more compartments characterized in terms of parameters from which the mixed-venous return of gas X can be predicted. These parameters include the total number of compartments, the fraction of the total cardiac output received by the respective compartment, the respective compartment's storage capacity for gas X and the fraction of the overall production/consumption of gas X that can be assigned to the compartment.

The total number of compartments (ncomp) in the model must be known or selected, and then each compartment (k) is assigned a fraction of the total cardiac output (qk), a storage capacity for gas X (dXk), and a fraction of the overall production/consumption rate of gas X (vXk). In general, the storage capacity for any gas X in a compartment is known for an average subject of a particular weight, and then scaled proportional to the actual weight of the subject under test.

Modeling/predicting the mixed-venous return can be done for any gas X using the following information:
1. A formula for conversion of end-tidal partial pressures to blood content of gas X (i.e. determining the content of the gas X in the pulmonary end-capillary blood based on data with respect to partial pressures).
2. the fraction of the overall production/consumption of the gas X which occurs in the compartment;
3. the storage capacity of the compartment for gas X;
4. blood flow to/from the compartment.

Some examples of gas X include isoflorane, carbon dioxide and oxygen.

Compartmental modeling of gas dynamics may be simplified using a single compartment model.

Means for controlling gas delivery typically include suitable gas flow controllers for controlling the rate of flow of one or more component gases. The gas delivery may be controlled by a computer for example an integrated computer chip or an external computer running specialized computer readable instructions via which inputs, computations and other determinations of parameter and controls are made/handled. The computer readable instructions may be embodied in non-transitory computer readable medium which be distributed as a computer program product.

It will be appreciated that logistically attainable target values for end tidal partial pressures of gas X may be set for respective breaths within a series breaths which are taken preliminary to or as part of a diagnostic or therapeutic procedure. Typically these values are defined in advance for the series or for at least part of the series of breaths. As described below, these individually logistically attainable values may be used to attain values in multiple breaths that are not logistically attainable in one breath.

The term "tuning" and related terms (e.g. tune, tuned etc.) means that a value for an estimated or measured parameter that is required to compute $F_IX$ is adjusted, as necessary or desirable, to enable more precise computation of the $F_IX$ required to achieve a $PetX[i]^T$, preferably based on observed differences between the target $PetX[i]^T$ set for one or more respective breaths and actual PetX[i] value(s) obtained for the respective breath(s), if any, such that post-adjustment observed value(s) more closely match the respective target value(s). The tuned parameter(s) can be understood to fall into two categories: lung and non-lung related parameters. Preferably, the lung related parameter is FRC. A step change in the end tidal partial pressure of gas X is required to tune this parameter. Non-lung related parameters are preferably tissue related parameters, preferably those required for computing a compartmental model of gas dynamics, preferably parameters governing total metabolic production or consumption of gas X in the body or the overall cardiac output, optionally parameters affecting assessment of the contribution of a respective compartment to the mixed venous content of gas X, preferably as a function of the production or consumption of gas X in the respective compartment, the assigned storage capacity for gas X in the respective compartment and the contribution of blood flow from the respective compartment to the total cardiac output, for example, by observing that a repeatedly targeted value does not drift when attained. Drift can be defined in the negative or considered to have been corrected for, for example, if an adjusted value for a tissue related parameter results in a variation of no greater than 1 to 2 mm of Hg (ideally approximately 1 mm of Hg or less) between observed and targeted end tidal values of gas X for a series of 5 consecutive breaths (i.e. where the end tidal partial pressure of gas X is sought to be maintained for a series of breaths e.g. 30 breaths and observed drift is corrected).

Tuning FRC is important for transitioning accurately between end-tidal values. Tuning non-lung related parameters e.g. VCO2 is important so that the steady state error between end-tidal values is small. The tuning requirements depend on the goals of the targeting sequence. For example, in the case of inducing a step increase in the end-tidal partial pressure of CO2 from 40 mmHg to 50 mmHg, if attaining 50 mmHg in the first breath is important, FRC is preferably tuned. If achieving 50 mmHg in the first breath is not vital, but achieving this target in 20 breaths is all that may matter, a non-lung related parameter such as VCO2 should be tuned. If the goal of the end tidal targeting sequence is to achieve 50 mmHg in one breath, and then maintain 50 mmHg for the ensuing 20 breaths, both FRC and a non-lung related parameter should be tuned. If you don't care if you get to 50 mmHg in the first breath, and then drift to 55 after 20 breaths, don't tune either.

The following are examples of end tidal values that would be achieved for each combination. Assume transition is made on the second breath (bold):

Tuned FRC (good transition), untuned VCO2 (bad steady state error)—40, 50, 51, 52, 53, 54, 55, 55, 55, 55, 55, 55

Untuned FRC (bad transition), tuned VCO2 (no steady state error)—40, 59, 56, 53, 52, 51, 50, 50, 50, 50, 50

Tuned FRC (good transition), tuned VCO2 (no steady state error)—40, 50, 50, 50, 50, 50, 50, 50, 50

Untuned FRC (bad transition), untuned VCO2 (bad steady state error)—40, 62, 60, 58, 57, 56, 55, 55, 55, 55.

For example, to achieve a progressively increasing end tidal partial pressure of gas X where the actual or absolute values are not of concern, only that the values keep increasing in each breath, it would not be necessary to tune FRC or VCO2. However, to transition from 40 to 50 mmHg (for example, where gas X is CO2), though not necessarily in one breath, it would be preferable to tune a non-lung related parameter e.g. VCO2 but not FRC. If it were important to transition from 40 mmHg to 50 mmHg in one breath, but not so important if the end tidal values drifted away from 50 mmHg after the first breath, it would be important to tune FRC but not VCO2 etc. Nevertheless, a target would be set for each respective breath [i] and that target would be effectively attained with a degree of accuracy and immediacy necessary for the application in question. Accordingly, a tidal based model for targeting end tidal partial pressure of a gas X provides a tunable flexible system for attaining those targets in line with a wide variety of objectives of the user.

It is to be understood that this tuning can be applied independently to each of the gases that are being targeted, as each gas can be targeted independently of the other gases.

An attainable target may be maintained in one or more subsequent breaths by setting the target end tidal value for the respective breath to be the same as PetX[i−1]. A target that is not attainable in one breath may be obtained in a series of breaths [i] . . . [i+n].

As suggested above and discussed below, it is possible that a particular end tidal partial pressure is not logistically attainable in one breath. If logistically attainable at all, such a target may be logistically attained only after multiple breaths. In contrast to methods requiring negative feedback, such as dynamic end tidal forcing, in one aspect of the method of the present invention this number of breaths may be pre-defined prospectively. This number of breaths may also be minimized so that the ultimate end tidal target is attained as rapidly as logistically feasible, for example by simple computational trial and error with respect to an incremented series of target. As described below, logistic constraints could be seen as limitations to inhaling the amount of the gas X that needs to be inhaled to reach a target concentration on the next breath; this could be because of limitations of available concentration X, or volume of inspired gas or both. Mandatory constraints are at least those inherent in any method of controlling the end tidal partial pressure of a gas X by way of inhalation of concentrations of gas X in that $F_IX$ cannot be less 0% and greater than 100% for any given breath. Constraints may also be selected as a matter of operational necessity or efficiency—so called "operational constraints" which may be self-imposed but not mandatory in all cases. For example, practically speaking, it may be inadvisable for safety reasons to administer a gas X (especially where gas X is not oxygen) in the highest feasible concentrations due to patient safety risks accompanying failure of the system. Accordingly, for safety reasons it may be advisable for a component gas comprising gas X to have at least 10% oxygen thereby defining an optional logistical limit of the method. Therefore what is logistically achievable is understood to be operationally limited by the composition of all the gas sources to which the apparatus is connected at any point in time. Furthermore, as described below, sequential gas delivery is typically effected by delivering a gas of a first composition followed by a neutral gas. The rate of flow and hence volume of the first gas generally controlled to within certain parameters so that the second gas at least fills the anatomic dead space. This is operationally mandatory in the sense that not all values for this parameter are workable, especially if a medically relevant target end tidal partial pressure of gas X is sought to be achieved in one breath as opposed to incrementally over several breaths. What is logistically attainable will be dictated by the extant rate of flow, if unvaried, or if varied, by the range of logistically practicable rates of flow. Hence, what is logistically attainable may be tied to independently controlled parameters which may or may not be varied. Hence, some of these operational parameters may be mandatory in a particular context or in a universal sense (running the system so that it always works without reset e.g. recalculation of prospectively calculated $F_IX$ values for a dynamic set of breaths of interest if the tidal volume falls outside established controls.

According to one embodiment of the method, the model of gas dynamics that is used to predict $C_{MV}X[i]$ in the mixed venous blood entering the subject's lung for gas exchange in the respective breath [i] estimates a value of $C_{MV}X[i])$ by: (a) dividing tissues to which the subject's arterial blood circulates into one or more compartments (k); and (b) determining the contribution of a respective compartment to the mixed venous content of gas X as a function of the production or consumption of gas X in the respective compartment, the assigned storage capacity for gas X in the respective compartment and the contribution of blood flow from the respective compartment to the total cardiac output or pulmonary blood flow. For example, where gas X is carbon dioxide the content of carbon dioxide in the mixed venous blood leaving a compartment $C_VCO2_k[i]$ is determined by assigning to a compartment a fraction of the overall metabolic carbon dioxide production ($vco2_k$), a fraction of the total cardiac output ($q_k$) and a storage capacity for carbon dioxide ($dCO2_k$).

In contrast to a negative feedback system, the aforedescribed system is a prospective end-tidal targeting system. Prior to execution of an end-tidal targeting sequence, the tissue model is used to predict the time course of the mixed-venous blood gases that will result from ideal execution of the sequence.

The time course of predicted mixed-venous gases is used to compute the series of inspired gas mixtures required to realize the target end-tidal partial pressures of gases. In this way, assuming that the end-tidal partial pressures of gases adhere to the targets allows prediction of the mixed-venous gases, and prediction of the mixed-venous gases allows a priori calculation of the inspired gas mixtures required to accurately implement the end-tidal targets. There is no requirement to modify the series of the inspired gas mixtures calculated before execution of the sequence based on deviations of the measured end-tidal partial pressures of gases from the targets during execution of the sequence.

Instead, the system is tuned to obtain tuned values for certain parameters before execution of the sequence so that the end-tidal partial pressures of gases induced during sequence execution closely adhere to the target functions without the need for any feedback control. Optionally, the program code includes code for directing a suitable gas delivery device such as a rapid flow controller to deliver a gas X containing gas having an $F_IX$ output from a mass balance equation. The term "gas delivery means" by contrast to gas delivery device refers to a discrete component of a gas delivery device that is used to control the volume of gas delivered at a particular increment in time such as a rapid flow controller.

It will be appreciated that each of the key method steps for carrying out the invention can be functionally apportioned to different physical components or different computer programs and combinations of both. Furthermore a device according to the invention will optionally comprise one or more physical components in the form of a gas analyzer, a pressure transducer, a display, a computer, a gas delivery device such as a rapid flow controller, a gas channeling means (gas conduits/tubes), standard electronic components making up a PCB, input devices for setting parameters etc. The various means for carrying out these steps include without limitation one in the same physical means, or different physical means on different devices, the same device or the same device component. Depending on the number of added gases these components may multiplied or where possible shared.

In another aspect, the present invention is also directed to a device comprising an integrated circuit chip configured for carrying out the method, or a printed circuit board (comprising discrete or integrated electronic components). The device optionally includes at least one gas delivery means such as a rapid flow controller. The device optionally includes an input device for inputting various parameters described herein. The parameters can be input via a variety of means including, but not limited to, a keyboard, mouse, dial, knob, touch screen, button, or set of buttons.

It is understood that any input, computation, output, etc. described herein can be accomplished by a variety of signal processing means including, but not limited to, a programmable processor, a programmable microcontroller, a dedicated integrated circuit, a programmable integrated circuit, discrete analog or digital circuitry, mechanical components, optical components, or electrical components. For example, the signal processing steps needed for executing the inputs, computations and outputs can physically embodied in a field programmable gate array or an application specific integrated circuit.

The term "blending" may be used to describe the act of organizing delivery of one gas in conjunction with at least one other and hence the term blending optionally encompasses physical blending and coordinated release of individual gas components.

The term "computer" is used broadly to refer to any device (constituted by one or any suitable combination of components) which may be employed in conjunction with discrete electronic components to perform the functions contemplated herein, including computing and obtaining input signals and providing output signals, and optionally storing data for computation, for example inputs/outputs to and from electronic components and application specific device components as contemplated herein. As contemplated herein a signal processor or processing device in the form of a computer may use machine readable instructions or dedicated circuits to perform the functions contemplated herein including without limitation by way of digital and/or analog signal processing capabilities, for example a CPU, for example a dedicated microprocessor embodied in an IC chip which may be integrated with other components, for example in the form of a microcontroller. Key inputs may include input signals from—a pressure transducer, a gas analyzer, any type of input device for inputting a target end tidal partial pressure of gas X (for example, a knob, dial, keyboard, keypad, mouse, touch screen etc.), input from a computer readable memory etc. Key outputs include output of the flow and/or composition of gas required to a flow controller.

For example of a compartmental model for mixed venous blood carbon dioxide dynamics may assign body tissues to k compartments e.g. 5 compartments and assign the contribution of a respective compartment to the mixed venous content of carbon dioxide as a function of the production of carbon dioxide in the respective compartment, the assigned storage capacity for carbon dioxide in the respective compartment and the contribution of blood flow from the respective compartment to the total cardiac output.

In one aspect, the present invention is directed to a non-transitory computer readable memory device having recorded thereon computer executable instructions for carrying out one or more embodiments of the above-identified method. The invention is not limited by a particular physical memory format on which such instructions are recorded for access by a computer. Non-volatile memory exists in a number of physical forms including non-erasable and erasable types. Hard drives, DVDs/CDs and various types of flash memory may be mentioned. The invention, in one broad aspect, is directed to a non-transitory computer readable medium comprising computer executable instructions for carrying out one or more embodiments of the above-identified method. The instructions may take the form of program code for controlling operation of an electronic device, the program code including code for carrying out the various steps of a method or control of an apparatus as defined above.

A "gas delivery device" means any device that can make a gas of variable/selectable composition available for inspiration. The gas delivery apparatus may be used in conjunction with a ventilator or any other device associated with a breathing circuit from which the subject is able to inspire a gas of variable/controllable composition without substantial resistance. Preferably, the composition of the gas and/or flow rate is under computer control. For example, such a device may be adapted to deliver at least one gas (pure or pre-blended) at a suitable pre-defined rate of flow. The rate of flow may be selectable using a form of input device such a dial, lever, mouse, key board, touch pad or touch screen. Preferably the device provides for one or more pure or blended gases to be combined i.e. "a gas blender".

A "gas blender" means a device that combines one or more stored (optionally stored under pressure or delivered by a pump) gases in a pre-defined or selectable proportion for delivery a selectable rate of flow, preferably under computer control. For example or more stored gases may be combined with pumped room air or a combination of pure or blended (each blended gas may have at least 10% oxygen for safety) gases respectively contain one of carbon dioxide, oxygen and nitrogen as the sole or predominant component. Optionally, the selectable proportion is controlled automatically using an input device, optionally by variably controlling the flow of each stored gas (pure or pre-blended) separately, preferably using rapid flow controllers, to enable various concentrations or partial pressures of a gas X to be selected at will within a pre-defined narrow or broad range. For example, a suitable blender may employ one or more gas reservoirs, or may be a high flow blender which blows gas past the mouth i.e. in which gas that is not inspired is vented to the room.

A "partial rebreathing circuit" is any breathing circuit in which a subject's gas requirements for a breath are made up in part by a first gas of a selectable composition, and a rebreathed gas to the extent that the first gas does not fully satisfy the subject's volume gas requirements for the breath. The first gas must be selectable in at least one of composition or amount. Preferably the amount and composition of the first gas is selectable. The rebreathed gas composition optionally consists of previously exhaled gas that has been stored or a gas formulated to have the same concentration of gas X as previously exhaled gas or a second gas has a gas X concentration that is selected to correspond (i.e. has the same concentration) as that of the targeted end tidal gas composition for a respective breath [i].

Preferably the circuit is designed or employable so that the subject receives the entirety of or a known amount of the first gas in every breath or in a consecutive series of breaths forming part of gas delivery regimen. In a general sense a re-breathed gas serves a key role in that it does not contribute significantly to the partial pressure gradient for gas flow between the lung and the pulmonary circulation when intake of the gas at least fills the entirety of the anatomic dead space. Therefore, in the case of a spontaneously breathing subject (whose tidal volume is not controlled e.g. via a ventilator) the subject's unpredictable tidal volume does not defeat prospective computation of the controlled gas composition required to attain or target PetX[i] for a respective breath [i].

Optionally, the "rebreathed gas" may be constituted by or substituted by a prepared gas (in terms of its gas X content). Thus, according to one embodiment of the invention, the second gas has a gas X concentration that is selected to correspond to that of the targeted end tidal gas composition for a respective breath [i]. The volume of the first inspired gas may also be adjusted (e.g. reduced) to target $PetX[i]^T$ for a respective breath [i] such that the subject receives an optimal amount of a gas having a gas X concentration that corresponds to $PetX[i]^T$.

As alluded to above, it will be appreciated that the gas X content of a prepared gas can be formulated to represent a gas of a "neutral" composition. Thus the total inspired gas for a respective breath [i] will comprise a first inspired gas having a controlled volume and gas X concentration ($F_I X$) and a second gas which has a gas X content whose contribution to establishing a partial pressure gradient between the lung and pulmonary circulation is optionally minimized. In a broader sense, the second inspired gas content of gas X can be optimized to attain a targeted end tidal concentration (for a universal set of circumstances) and in a sub-optimal sense this concentration at least does not defeat the ability to prospectively compute an $F_I X$ for the purposes of attaining or targeting a PetX[i] for a respective breath [i] (i.e. not knowing the subject's tidal volume for a respective breath [i] will not preclude such computation).

"Prospectively" or a "prospective computation" means, with reference to a determination of an amount of gas X required to be inspired by the subject in an inspired gas to attain or target a $PetX[i]^T$ for a respective breath [i] (optionally computed in terms of $F_I X$), using inputs required to compute a mass balance equation (preferably including $C_{MV} X[i]$), without necessary recourse to feedback to attain rapidly and repeatably. In contrast, to a negative feedback system, which relies on ongoing measurements of PetX[i] to provide feedback for continually adjusting computed $F_I X$ values to minimize the discrepancy between target and measured PetX[i] values, the system of the present invention is adapted to attain logistically achievable end tidal values rapidly and accurately (as defined herein) without recourse to feedback. As discussed herein, a negative feedback system suffers from an inherent trade-off between response time and stability. According to the present invention, recourse to feedback is designed to be unnecessary for the purpose of attaining logistically achievable PetX targets rapidly and predictably.

Of further consideration are the delays associated with measurement of the end-tidal partial pressures of gases which are required for feedback into the system. Gas composition analysis is performed by continuously drawing gas from proximal to the subject's airway into a gas analyzer through a sampling catheter. The gas analyzer returns a time varying signal of gas composition which is, however, delayed from the actual ventilatory phase of the subject by the travel time through the sampling catheter and the response time of the gas analyzer. Therefore, at the start of any inspiration, the end-tidal partial pressures of gases from the immediately previous breath are not yet known. Where the sampling catheters are long, such as in an MRI environment where the patient is in the MRI scanner and the gas analyzers must be placed in the control room, this delay can reach three or more breaths. As in any negative feedback system, this delay in measuring the controlled parameter will further destabilize and limit the response time of the system.

A "sequential gas delivery device" means, with respect to delivering a gas in successive respective breaths [i], a device for delivery of a controlled gas mixture in the first part of a respective breath [i] followed by a "neutral" gas in the second part of the respective breath [i]. A controlled gas mixture is any gas that has a controllable composition with respect to one or more gases of interest used to compose it. Accordingly, where the gas of interest is a gas X, the controlled gas mixture has an amount of gas X, optionally defined in terms of a concentration of gas X denoted as $F_I X$. The controlled gas mixture may be referred to, for convenience, as a first inspired gas. Gas inspired in any breath is "neutral", inter alia, if it has the same composition as gas expired by the subject in a previous breath. The term "neutral" gas is used because the gas in question is one which has the same partial pressure of one or more gases of interest as the blood, in the alveoli, or in the pulmonary capillaries, and hence, upon inspiration into the alveolar space, in the second part of a respective breath, this gas does not exchange any gas with the pulmonary circulation. Unless otherwise defined explicitly or implicitly a gas of interest is generally one for which the end tidal partial pressure is sought to be controlled according to the invention.

A volume of gas that enters the alveolar space and exchanges gas with the pulmonary circulation for a breath [i] may be defined independently of a fixed tidal volume, for example by:
  a. setting the rate of flow of a controlled gas mixture (also termed fresh gas flow rate) in a rebreathing circuit to be less than the patient's minute ventilation or minute ventilation minus anatomic dead space ventilation (i.e. such that the last inspired second gas at least fills the anatomical dead space if not also part of the alveolar space);
  b. obtaining input of the rate of flow or volume of the controlled gas mixture into the circuit for the respective breath (this rate can be maintained from breath to breath or varied) and computing the effective volume of alveolar gas exchange for the respective breath based on the rate of fresh gas flow for the respective breath.

According to one embodiment, the rebreathing circuit is a sequential gas delivery circuit.

According to another embodiment, volume of gas that enters the alveolar space and exchanges gas with the pulmonary circulation is determined by utilizing a fixed tidal volume set for the respective breath (e.g. using a ventilator) and subtracting a volume corresponding to the subject's anatomic dead space volume.

The $F_I X$ may be set independently of the concentration of any other component of the inspiratory gas.

Optionally, a gas X and a gas Y are components of the inspired gas and a target arterial concentration of gas X and a target arterial concentration of a gas Y are selected for a respective breath, independently of each other, and, if present, independently of the concentration of any other component Z of the inspiratory gas.

A mass balance equation that comprises terms "corresponding to" all or an application-specific subset of the terms in equations 1 or 2 above means that the same underlying parameters are accounted for.

According to one aspect of the invention (which may be implemented in connection with any one or more of compatible embodiments of the invention defined hereinabove), the invention is directed to an apparatus for controlling an amount of at least one gas X in a subject's lung to attain a series of targeted end tidal partial pressures of at least one gas X ($PetX^T$), the series of targeted end tidal partial pressures of at least one gas X ($PetX^T$) adapted to stimulate a physiological response, the apparatus comprising:

(1) a gas delivery device;
(2) a control system for controlling the gas delivery device, wherein the control system is adapted to target a series of $PetX^T$ values for a respective series of intervals, the control system including means for:
   a. Obtaining input of a series of logistically attainable $PetX^T$ values for the series of respective intervals; and
   b. Determining an amount of gas X required to be inspired by the subject in an inspired gas to target the $PetX^T$ for a respective interval;
   c. Controlling the amount of gas X in a volume of gas delivered to the subject in a respective interval to target the respective $PetX^T$ for the interval.

The series of $PetX^T$ values preferably comprise at least one of a set of $PetX^T$ increments and a set of $PetX^T$ decrements.

The term "interval" is used broadly to mean a time interval of selected length, an interval defined by the duration of a respective inspiratory cycle and a previous or ensuing expiratory cycle, for example, a respective breath [i] defined by an inspiratory cycle and the expiratory cycle which follows it, and/or an interval defined by a pattern of a physiological response. The term 'pattern of a physiological response' means a pattern sufficient to define a dose-response (stimulus-response) relationship for a full range of the physiologic response or for at least a part thereof that reveals a pattern of interest, wherein the increments in dose or stimulus are selected to disclose the true shape of the dose response curve. A portion of interest may of diagnostic or medical interest to define a normal pattern of the response for example to differentiate between variations in a normal response for different groups e.g. ages, and optionally a differential response e.g. particular range or prevalence of a response or a different or pathologic response, associated with a condition or disease. For example, a pattern may disclose a linear, exponential or sigmoidal dose response curve for an individual or group of common individuals selected from at least one of persons having a 'normal' physiological response and persons disclosing a different or pathological physiological response. For example, a pattern may disclose that a response is sigmoidal and not linear (e.g. it is only linear over a certain range of the stimulus) when a fuller range of the response is probed using a suitable range and series of smaller changes in stimulus. For example, an interval of diagnostic interest may be a fraction of the amount of time required to observe the time course of the response wherein the fraction is sufficiently small to obtain a set of values defining the pattern of response. The ramp sequence may also be selected to determine a time course of a full or partial range of a physiological response by tracking signals signifying that a particular condition, associated with a direct or indirect measure of the response, has been met, the condition preferably of the type satisfied by attainment or projected attainment of a threshold amount change in a measurable parameter correlated with a physiologic response to a stimulus comprising or consisting of an increment or decrement in a subject's end tidal partial pressure of gas X. A fraction or proportionate amount of a time period required to observe a continuous time course of a physiological response or satisfy a set threshold amount of change in the response (attained or predicted to be attained based on a known or predictable mathematical relationship between the stimulus—an increment or decrement in PetX—and a measurable parameter that defines the time course of the response), is then defined to be sufficient to demarcate the end of a previous interval and the beginning of a next ensuing interval. The time course may be selected to grade individuals in terms of the overall appearance of the pattern (measurement of a continuous variable) or differentiate between populations with respect satisfying one or more individual criteria (e.g. a discontinuous variable eliciting a yes/no answer).

A gas delivery device can be controlled to attain a series of targeted end tidal partial pressures of at least one gas X ($PetX^T$) by the prospective model described herein; or by a combination of a prospective model and feedback control (known as dynamic end tidal forcing), for example, wherein the feedback loop (e.g. using a PID controller) adds a control signal to adjust a prospective determination of $F_I X$; the control signal generated based on the difference between the target and measured end tidal values. Computation of FIX can be accomplished using the tidal model equations herein by adapting the continuous flow equations published by Robbins and Swanson.

According to one aspect of the invention (which may be implemented in connection with any one or more of compatible embodiments of the invention defined hereinabove), the invention is directed to a method of controlling an amount of at least one gas X in a subject's lung to attain at least one targeted end tidal partial pressure of the at least one gas X, comprising the steps of:

a. Obtaining input of a logistically attainable end tidal partial pressure of gas X ($PetX[i]^T$) for a series of respective breaths [i];
b. Obtaining input of a prospective computation of an amount of gas X required to be inspired by the subject in an inspired gas to target the $PetX[i]^T$ for a respective breath [i] using inputs required to compute a mass balance equation, wherein one or more values required to control the amount of gas X in a volume of gas delivered to the subject is output from the mass balance equation; and optionally
c. Controlling the amount gas X in a volume of gas delivered to the subject in a respective breath [i] to target the respective $PetX[i]^T$ based on the prospective computation;
and wherein the respective $PetX[i]^T$ for the series of breaths [i] increases or decreases from the start of the series to the end of the series (from $PetX[i^1]^T$ to $PetX[i^n]^T$) in accordance with a ramp sequence (as defined below).

Optionally, the respective $PetX[i]^T$ for the series of breaths [i] increases every Nth breath in respective selected increments ("Z") from the start of the series to the end of the series (from $PetX[i^1]^T$ to $PetX[i^n]^T$), wherein either N equals 1 and Z is greater than 0 in each breath in the series, or N is greater than 1 and Z may be zero in breaths which are not the Nth breath and Z is greater than 0 in every Nth breath.

Optionally, the respective $PetX[i]^T$ for the series of breaths [i] decreases every Nth breath in respective selected decrements ("Z") from the start of the series to the end of the series (from $PetX[i^1]^T$ to $PetX[i^n]^T$), wherein either N equals 1 and Z is greater than 0, or N is greater than 1 and Z may be zero in breaths which are not the Nth breath and Z is greater than 0 in every Nth breath Accordingly, $PetX[i]^T$ may change every Nth breath in respective selected increments or decrements ("Z") from the start of the series to the end of the series (from $PetX[i^1]^T$ to $PetX[i^n]^T$), wherein N equals 1 and Z is greater than 0. In another embodiment, N is greater than 1 and Z may be zero in breaths which are not the Nth breath.

Embodiments in which $PetX[i^1]^T$ increases include the following. In one embodiment, "Z" is greater 0 and is the same in each breath in the series (N=1). For example, N may equal 1 and "Z" may equal 8. Therefore, for example, a target end tidal oxygen concentration may increase every breath (N=1) from $[i]^1$ to $[i]^n$ from $PetX[i^1]^T$=100 mm Hg to $PetX[i^n]^T$=180 mm Hg over the course of the next 10 contiguous breaths (respective targets in mm of Hg=108, 116, 124, 132, 140, 148, 156, 164, 172, 180). As another example, N may equal 5 and same end tidal target value may be maintained at the same target for the 4 breaths in between each $5^{th}$ breath such that it would take approximately 50 breath to span the same range of end tidal targets from $[i]^1=PetX[i^1]^T$=100 mm Hg to $[i]^{50}=PetX[i^{50}]^T$=180 mm Hg. This same sequence may be expressed another way i.e. Z is changing and for the series of fifty breaths as follows: Z equals, respectively 0, 0, 0, 0, 8, 0, 0, 0, 0, 8, 0, 0, 0, 0, 8, 0, 0, 0, 0, 8, 0, 0, 0, 0, 8, 0, 0, 0, 0, 8, 0, 0, 0, 0, 8, 0, 0, 0, 0, 8, 0, 0, 0, 0, 8 0, 0, 0, 0, 8.

In one embodiment, Z is selected to correspond to a selected rate of change in a physiological response to a stimulus (the stimulus being a correlate of $PetX[i]^T$ such as the arterial partial pressure of gas X (PaX)). The selected rate of change corresponds to a rate wherein a targeted physiologic response is substantially realized for each increment/decrement before the next increment/decrement, such that successive measurements of the response are substantially matched to an increment/decrement in a change in stimulus. Accordingly, it is possible to plot the change in response with respect to the change in $PetX[i]^T$ with substantial accuracy. For example, where the time course of the response of a physiologic parameter is exponential, the rate of change in $PetX[i]^T$ may be selected such that three time constants in the progress of the response (approximately 95% response) are achieved before the next increment/decrement in $PetX[i]^T$ stimulus is given. A time interval for executing the range in stimulus "R" or the range (extent) of the expected response "r" may be selected and the target change per breath in stimulus readily mathematically determined. For example, with respect to ramping up $PetCO_2[i]^T$ from 35 to 50 mm of Hg over a selected time period (e.g. approx. 5 minutes) increasing $PetCO_2[i]^T$ approx. 0.25 mm Hg every breath may define a suitable ramp sequence. Optionally, this rate may be corroborated. Corroboratively, a greater than 95% CVR response to a change in $PaCO_2$ may be determined to be achieved in 16-18 seconds. Thus increments of 1 mm of Hg every 16 second would be suitable. Assuming a subject inhales 15 times per minute (1 breath every 4 seconds, this corresponds to 0.25 mm of Hg every breath. Accordingly, according to one embodiment of the invention, optionally, the time interval over which the response is measured and the range of change in stimulus range may be input to facilitate execution of a ramp sequence so that a series of $PetCO_2[i]^T$ targets for the intervening breaths may be correspondingly obtained.

Optionally, with respect to increases in $PetCO_2[i]^T$, N is advantageously 1, 2 or 3 breaths, optionally 1 breath, and Z is the optionally the same for each increase, depending on the total time interval for executing the range in stimulus Z or desired response range optionally ranging from 0.2 to 2 mm Hg. Optionally, with respect to increases in $PetO2[i]^T$ N is advantageously 1 to 5, optionally 1, and Z is the optionally the same for each increase, Z ranging from 1 to 20 mm Hg. Simply by way of example, $PetO_2[i]^T$ may be increased every Nth breath wherein N=1 and Z=8 for each successive breath in the series e.g. ranging from 100 mm Hg to 350 mm Hg) while $PetCO2[i]^T$ is maintained constant. In another embodiment, $PetCO2[i]^T$ is increased each Nth breath e.g. from 35 mm Hg to 50 mm Hg (N=1, Z=0.25 for each successive breath in the series) while $PetO_2[i]^T$ is maintained constant.

Advantageously, as regards such sequences, where the targets are increased or decreased at a rate selected for observing a substantial response to an increment or decrement in stimulus (termed a "ramp sequence"); e.g. with respect to an exponential response, optionally at least a response corresponding to two time constants, optionally at least a 90-95% response or a response corresponding to three time constants, optionally approximately linearly with respect to time, the response (e.g. CVR) to a change in the end tidal concentration of gas X e.g. carbon dioxide, is substantially achieved within a given time increment e.g. spanning 4 breaths, and is optionally plotted (measurement may be more frequent) approximately every 4 breaths, in contrast to making the change in stimulus in one step, ideally, in one breath, in which case, the continuous plotting of the response reveals the time course of the response to the stimulus.

Accordingly the invention is also directed to an apparatus for controlling an amount of at least one gas X in a subject's lung to attain a targeted end tidal partial pressure of the at least one gas X, comprising:
(1) a gas delivery device;
(2) a control system for controlling the gas delivery device including means for:
a. Obtaining input of a concentration of gas X in the mixed venous blood entering the subject's pulmonary circulation for gas exchange in one or more respective breaths [i] ($C_{MV}X[i]$);
b. Obtaining input of a logistically attainable end tidal partial pressure of gas X ($PetX[i]^T$) for a respective breath [i];
c. Obtaining input of a prospective computation of an amount of gas X required to be inspired by the subject in an inspired gas to target the $PetX[i]^T$ for a respective breath [i] using inputs required to compute a mass balance equation including $C_{MV}X[i]$, wherein one or more values required to control the amount of gas X in a volume of gas delivered to the subject is output from the mass balance equation; and
d. Controlling the amount of gas X in a volume of gas delivered to the subject in a respective breath [i] to target the respective $PetX[i]^T$ based on the prospective computation; and optionally
e. Inputting values for execution of a ramp sequence (optionally via means for setting a cumulative time interval for measuring the response and a range of the stimulus or response to be canvassed, or optionally an increment or decrement Z (in the example above 0.25 mm of Hg) for each a series of respective breaths $[i]^1$ to $[i]^n$, and optionally N.

N may be fixed at 1 in which case Z will be greater than 0 or or N is greater than 1 and Z may be zero in breaths which are not the Nth breath and Z is greater than 0 in every Nth breath.

BRIEF DESCRIPTION OF THE FIGURES

The invention will now be described with reference to the figures, in which:

FIG. 3 is a detailed schematic representation of the movement of blood and the exchange of gases at the lungs when sequential rebreathing is not employed.

FIG. 7 is a Table of abbreviations (Table 1) used in the specification

FIG. 11 is a tabulated raw data set showing measured end $PetCO_2$ attained for 6 subjects when the end tidal gas concentrations described in Example 1 were targeted.

DETAILED DESCRIPTION OF A PREFERRED EMBODIMENT

Figure 1:
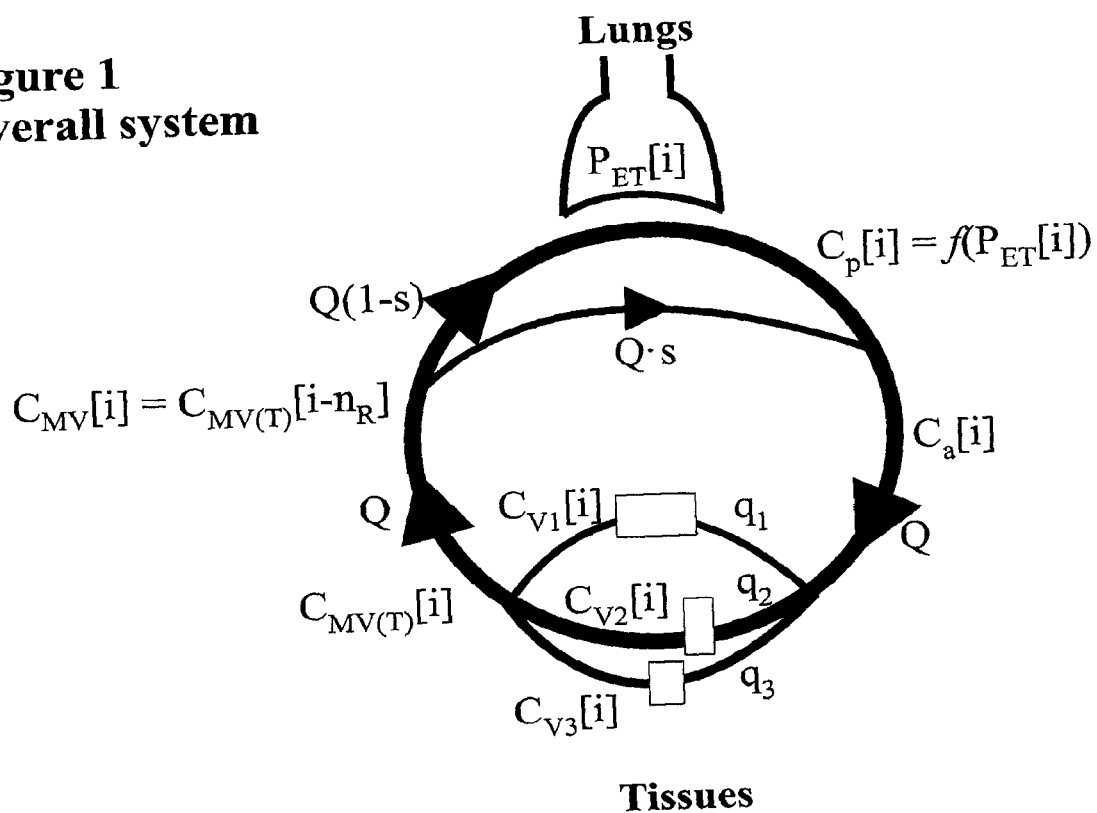
FIG. 1 is a schematic overview of the movement of blood and the exchange of gases throughout the entire system.

The invention is described hereafter in terms of one or more optional embodiments of a gas X, namely carbon dioxide and oxygen.

Prospective Modelling

Mass balance equations of gases in the lung are conventionally derived from a continuous flow model of the pulmonary ventilation. In this model, ventilation is represented as a continuous flow through the lungs, which enters and exits the lungs through separate conduits. As a consequence, for example, the anatomical dead space would not factor into the mass balance other than to reduce the overall ventilatory flow into the alveolar space. In reality, however, ventilation in humans is not continuous, but tidal. Gas does not flow through the lungs, but enters the lungs during a distinct inspiration phase of the breath and exits during a subsequent expiration phase of the breath. In each breath cycle, gas is inspired into the lungs via the airways and expired from the lungs via the same airways through which gas was inspired. One possible implication, for example, is that the first gas inspired into the alveolar space in any breath is residual gas which remains in the anatomical dead space following the previous expiration. Continuous flow models neglect the inspiration of residual gas from the anatomical dead space, and therefore, since accounting for such a factor is generally desirable, do not accurately represent the flux of gases in the lungs.

As continuous flow models of pulmonary ventilation do not correctly represent the flux of gases in the lungs, the end-tidal partial pressures of gases induced from the inspiration of gas mixtures computed from such a model will, necessarily, deviate from the targets.

By contrast, according to one aspect of the present invention, a mass balance equation of gases in the lungs is preferably formulated in terms discrete respective breaths [i] including respective discrete volumes corresponding to one or more of the FRC, anatomic dead space, the volume of gas X transferred between the pulmonary circulation and the lung in a respective breath [i] and an individual tidal volume of a respective breath [i]) is adaptable to account, for example, for inspiration of residual gas from the anatomical dead space into the alveolar space in each breath. Inasmuch as a tidal model more faithfully represents the actual flux of gases in the lungs compared with the conventional model, the induced end-tidal partial pressures of gases, to an extent that the model is fully exploited, it will more closely adhere to the targets compared with results achieved using a continuous flow model.

Moreover, we have found that using a tidal model of pulmonary ventilation, can be synergistically employed with a sequential gas delivery system to facilitate closer adherence to targets in both ventilated and spontaneously breathing subjects without reliance on a negative feedback system.

According to the present invention, a prospective determination of pulmonary ventilation and gas exchange with the blood can efficiently exploited even in spontaneously breathing subjects where the ventilatory parameters are highly variable and difficult to measure.

Where mechanical ventilation is employed, a prospective model of pulmonary ventilation and gas exchange with the blood envisages that the subject's ventilatory parameters can be estimated or measured to a level of accuracy sufficient to employ prospective control of the end-tidal partial pressures of one of more gases.

According to one embodiment of the invention, a technique of inspiratory gas delivery, sequential rebreathing, which, when using a tidal model of the pulmonary ventilation, significantly reduces or eliminates the dependence of the calculation of the inspired gas composition to be delivered in each breath, and therefore the actual end-tidal partial pressures of gases induced, on the subject's ventilatory parameters.

In parallel to what we have observed from studies with respect to the subject's ventilatory parameters, we have found that when we run a set of standardized tuning sequences, our model of the tissues more accurately reflects the actual dynamics of the gas stored in the subject's tissues. The model parameters may be refined until the end-tidal partial pressures of gases induced by execution of the tuning sequences sufficiently adhere to the targets without the use of any feedback control.

Sequential Gas Delivery

Sequential rebreathing is a technique whereby two different gases are inspired in each breath a controlled gas mixture followed by a "neutral" gas. A controlled gas mixture is any gas that has a controllable composition. Gas inspired in any breath is neutral if it has the same composition as gas expired by the subject in a previous breath. Neutral gas is termed as such since it has substantially the same partial pressures of gases as the blood in the pulmonary capillaries, and hence, upon inspiration into the alveolar space, does not substantially exchange any gas with the pulmonary circulation. Optionally, the rebreathed gas has a composition that is selected to correspond (i.e. have the same gas X concentration as that of) the targeted end tidal gas composition for a respective breath [i]. It will be appreciated that a modified sequential gas delivery circuit in which the subject exhales via a port leading to atmosphere and draws on a second gas formulated by a second gas delivery device (e.g. a gas blender) could be used for this purpose, for example where the second gas is deposited in an open ended reservoir downstream of a sequential gas delivery valve, for example within a conduit of suitable volume as exemplified in FIG. 7 of U.S. Pat. No. 6,799,570.

Sequential rebreathing is implemented with a sequential gas delivery breathing circuit which controls the sequence and volumes of gases inspired by the subject. A sequential gas delivery circuit may be comprised of active or passive valves and/or a computer or other electronic means to control the volumes of, and/or switch the composition or source of, the gas inspired by the subject.

The controlled gas mixture is made available to the sequential gas delivery circuit for inspiration, optionally, at a fixed rate. On each inspiration, the sequential gas delivery circuit ensures the controlled gas mixture is inspired first, for example with active or passive valves that connect the subject's airway to a source of the controlled gas mixture. The supply of the controlled gas mixture is controlled so that it is reliably depleted in each breath.

Once the supply of the controlled gas mixture is exhausted, the sequential gas delivery circuit provides the balance of the tidal volume from a supply of neutral gas exclusively, for example with active or passive valves that connect the subject airway to the subject's exhaled gas from a previous breath.

Gas expired in previous breaths, collected in a reservoir, is re-inspired in a subsequent breath. Alternatively, the composition of gas expired by the subject can be measured with a gas analyzer and a gas with equal composition delivered to the subject as neutral gas.

During inspiration of the neutral gas and expiration, the supply of the controlled gas mixture for the next inspiration accumulates at the rate it is made available to the sequential gas delivery circuit. In this way, the subject inspires only a fixed minute volume of the controlled gas mixture, determined by the rate at which the controlled gas mixture is made available to the sequential gas delivery circuit, independent of the subject's total minute ventilation, and the balance of subject's the minute ventilation is made up of neutral gas.

Examples of suitable sequential gas delivery circuits are disclosed in US Patent Application No. 20070062534.

The fixed availability of the controlled gas mixture may be accomplished by delivering a fixed flow rate of the controlled mixture to a physical reservoir from which the subject inspires. Upon exhaustion of the reservoir, the source of inspiratory gas is switched, by active or passive means, to neutral gas from a second gas source, for example a second reservoir, from which the balance of the tidal volume is provided.

It is assumed that in each breath the volume of the neutral gas inspired at least fills the subject's anatomical dead space. Herein, all of the controlled gas mixture reaches the alveolar space and any of the neutral gas that reaches the alveolar space does not exchange gas with the circulation as it is already in equilibrium with the pulmonary capillary blood.

Sequential gas delivery circuits may be imperfect in the sense that a subject will inspire what is substantially entirely a controlled gas mixture first. However, upon exhaustion of the supply of the controlled gas mixture, when neutral gas is inspired, an amount of controlled gas mixture is continually inspired along with the neutral gas rather than being accumulated by the sequential gas delivery circuit for the next inspiration (2). The result is that the subject inspires exclusively controlled gas mixture, followed by a blend of neutral gas and controlled gas mixture. As a result of the imperfect switching of gases, a small amount of the controlled gas mixture is inspired at the end of inspiration and enters the anatomical dead space rather than reaching the alveolar space. In practise, the amount of controlled gas mixture lost to the anatomical dead space is small, and therefore, the amount of controlled gas mixture that reaches the alveolar space can still be assumed equal to the rate at which the controlled gas mixture is made available to the sequential gas delivery circuit for inspiration. Therefore, the method described herein can be executed, as described, with imperfect sequential gas delivery circuits.

A simple implementation of sequential rebreathing using a gas blender and passive sequential gas delivery circuit is described in references cited below (2; 3). Other implementations of sequential gas delivery are described in patents (4-8).

The contents of all references set forth below are hereby incorporated by reference.

Various implementations of sequential gas delivery have described by Joseph Fisher et al. in the scientific and patent literature.

As seen FIG. 1, which shows a high level overview of the movement of blood and the exchange of gases throughout the entire system, the majority of the total blood flow (Q) passes through the pulmonary circulation. Upon transiting the pulmonary capillaries, the partial pressures of gases in the pulmonary blood equilibrate with the partial pressure of gases in the lungs ($P_{ET}[i]$)—the result is partial pressures of gases in the pulmonary end-capillary blood equal to the end-tidal partial pressures of gases in the lungs. The blood gas contents of this blood ($C_P[i]$) can then be determined from these partial pressures. The remaining fraction (s) of the total blood flow is shunted past the lungs and flows directly from the mixed-venous circulation into the arterial circulation without undergoing any gas exchange. Therefore, the gas contents of the arterial blood ($C_a[i]$) are a flow weighted average of the pulmonary end-capillary blood with gas contents equilibrated to that of the lungs, and the shunted blood with gas contents which are equal to the mixed-venous blood entering the pulmonary circulation ($C_{MV}[i]$). The arterial blood flows through the tissue capillary beds, where gases are exchanged between the blood and the tissues. There are one or more tissue capillary beds, each of which receives a fraction of the total blood flow (q) and has unique production, consumption, storage, and exchange characteristics for each gas. The gas contents in the venous blood leaving each tissue ($C_V[i]$) can be determined from these characteristics. The gas contents of the mixed-venous blood leaving the tissues ($C_{MV(T)}[i]$) are given by the flow weighted average of the gas contents in the venous blood leaving each tissue. The mixed-venous blood leaving the tissues enters the pulmonary circulation after the recirculation delay ($n_R$).

FIG. 2—The Tissues

Figure 2:
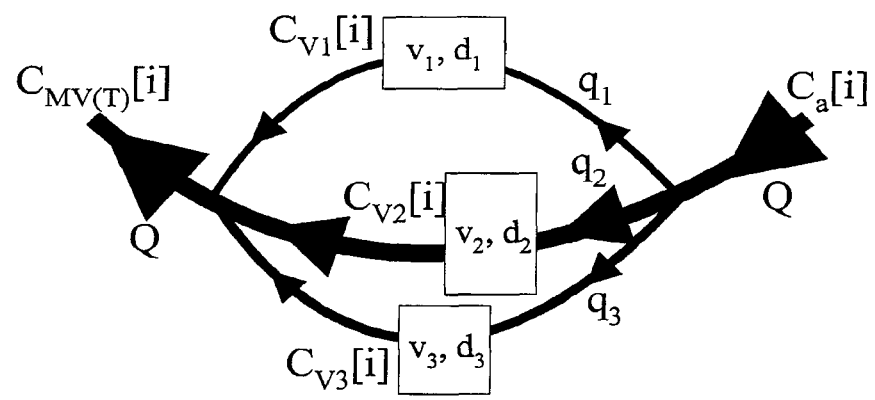
FIG. 2 is a detailed schematic representation of the movement of blood and the exchange of gases at the tissues.

As shown in FIG. 2, the total blood flow (Q) enters the tissue capillary beds from the arterial circulation, where the gas contents of the arterial blood ($C_a[i]$) are modified by gas exchange between the blood and the tissues. To obtain input of the gas contents of the mixed-venous blood, the flow of blood through the tissues is modelled as a system of one or more compartments where each compartment represents a single tissue or group of tissues. Each compartment is assumed to receive a fraction of the total blood flow (q) and has a unique production or consumption (v) of, and storage capacity (d) for, each gas. The content of gases in the venous blood leaving each compartment ($C_v[i]$) can be determined from the arterial inflow of gases, and the assumed production or consumption, and storage of the gas in the compartment. The blood flows leaving each compartment unite to form the mixed-venous circulation. Therefore, the gas contents of the mixed-venous blood leaving the tissues ($C_{MV(T)}[i]$) are given by the flow weighted average of the gas contents in the venous blood leaving each tissue.

FIG. 3—The Lungs (No Sequential Rebreathing)

As shown in FIG. 3, gas enters the lungs in two ways—diffusion from the pulmonary circulation and inspiration though the airways. The pulmonary blood flow is equal to the total blood flow (Q) less the fraction (s) of the total blood flow that is shunted past the lungs. The flux rate of gas between the lungs and the pulmonary blood flow in a breath (VB[i]) is, by mass balance, the product of the pulmonary blood flow and the difference between the gas contents of the mixed-venous blood ($C_{MV}[i]$) entering the pulmonary circulation and the gas contents of the pulmonary end-capillary blood ($C_P[i]$) leaving the pulmonary circulation.

The starting volume of the lungs in any breath is given by the functional residual capacity (FRC). This is the gas left over in the lungs at the end of the previous expiration, and contains partial pressures of gases equal to the target end-tidal partial pressures from the previous breath ($P_{ET}[i-1]^T$). The first part of inspiration draws gas in the anatomical dead space ($V_D$) from the previous breath into the alveolar space. The partial pressures of gases in this volume are equal to the target end-tidal partial pressures from the previous breath. Subsequently, a volume of a controlled gas mixture ($VG_1$) with controllable partial pressures of gases ($P_1[i]$) is inspired.

Figure 4:
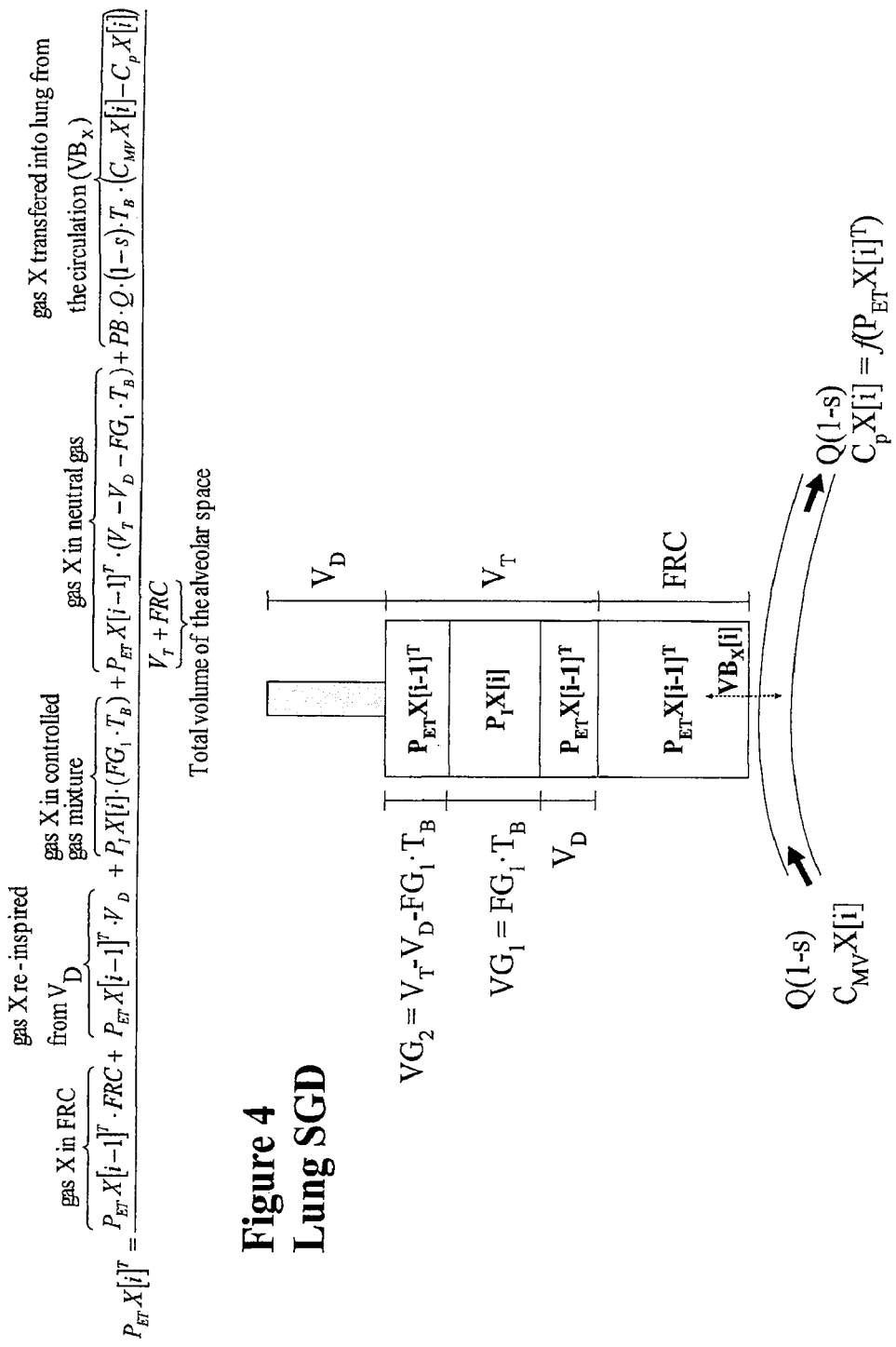
FIG. 4 is a detailed schematic representation of the movement of blood and the exchange of gases at the lungs when sequential rebreathing is employed.

FIG. 4—The Lungs (Sequential Rebreathing)

As shown in FIG. 4, gas enters the lungs in two ways diffusion from the pulmonary circulation and inspiration though the airways. The pulmonary blood flow is equal to the total blood flow (Q) less the fraction (s) of the total blood flow that is shunted past the lungs. The flux rate of gas between the lungs and the pulmonary blood flow in a breath (VB[i]) is, by mass balance, the product of the pulmonary blood flow and the difference between the gas contents of the mixed-venous blood ($C_{MV}[i]$) entering the pulmonary circulation and the gas contents of the pulmonary end-capillary blood ($C_P[i]$) leaving the pulmonary circulation.

The starting volume of the lungs in any breath is given by the functional residual capacity (FRC). This is the gas left over in the lungs at the end of the previous expiration, and contains partial pressures of gases equal to the target end-tidal partial pressures from the previous breath ($P_{ET}[i-1]^T$). The first part of inspiration draws gas in the anatomical dead space ($V_D$) from the previous breath into the alveolar space. The partial pressures of gases in this volume are equal to the target end-tidal partial pressures from the previous breath. Subsequently, a volume of a controlled gas mixture ($VG_1$) with controllable partial pressures of gases ($P_1[i]$) is inspired. The average volume of the controlled gas mixture inspired into the alveoli in each breath ($VG_1$) is given by the flow rate of the controlled gas mixture ($FG_1$) to the sequential gas delivery circuit (SGDC) delivered over one breath period ($T_B$). The balance of the tidal volume ($V_T$) is composed of a volume of neutral gas ($VG_2$). Where a sequential gas delivery circuit is used that provides previously expired gas as neutral gas, this volume contains partial pressures of gases equal to the target end-tidal partial pressures from the previous breath.

FIG. 5—Apparatus

Figure 5:
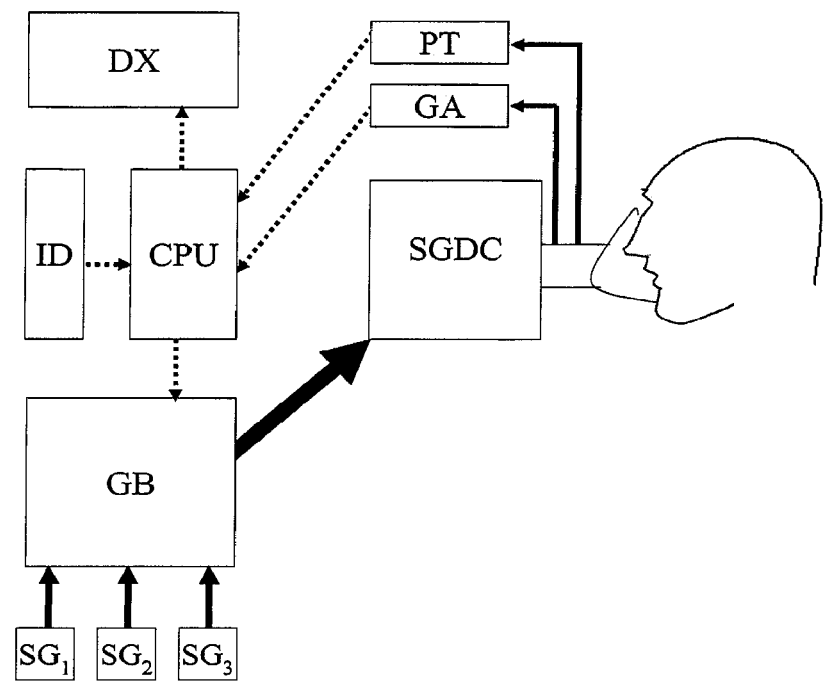
FIG. 5 is a schematic diagram of one embodiment of an apparatus according to the invention that can be used to implement an embodiment of a method according to the invention.

As shown in FIG. 5, according to one embodiment of an apparatus according to the invention, the apparatus consists of a gas blender (GB), a Hi-OX$_{SR}$ sequential gas delivery circuit (SGDC), gas analyzers (GA), a pressure transducer (PT), a computer (CPU), an input device (ID), and a display (DX). The gas blender contains three rapid flow controllers which are capable of delivering accurate mixes of three source gases ($SG_1$, $SG_2$, $SG_3$) to the circuit. The gases are delivered to the circuit via a gas delivery tube connecting the outlet of the gas blender to the inlet of the sequential gas delivery circuit. The gas analyzers measure the partial pressures of gases at the airway throughout the breath. The analyzers sample gas for analysis proximal to the subject's airway via a sampling catheter. A small pump is used to draw gases from the subject's airway through the gas analyzers. The pressure transducer is used for measurement of the breath period ($T_B$) and end-tidal detection, and also connected by a sampling catheter proximal to the subject's airway. The gas analyzers and pressure transducer communicate with the computer via analog or digital electrical signals. The computer runs a software implementation of the end-tidal targeting algorithm and demands the required mixtures from the blender via analog or digital electrical signals. The operator enters the target end-tidal values and subject parameters into the computer via the input device. The display shows the measured and targeted end-tidal gases.

FIG. 6—Tuning

Figure 6:
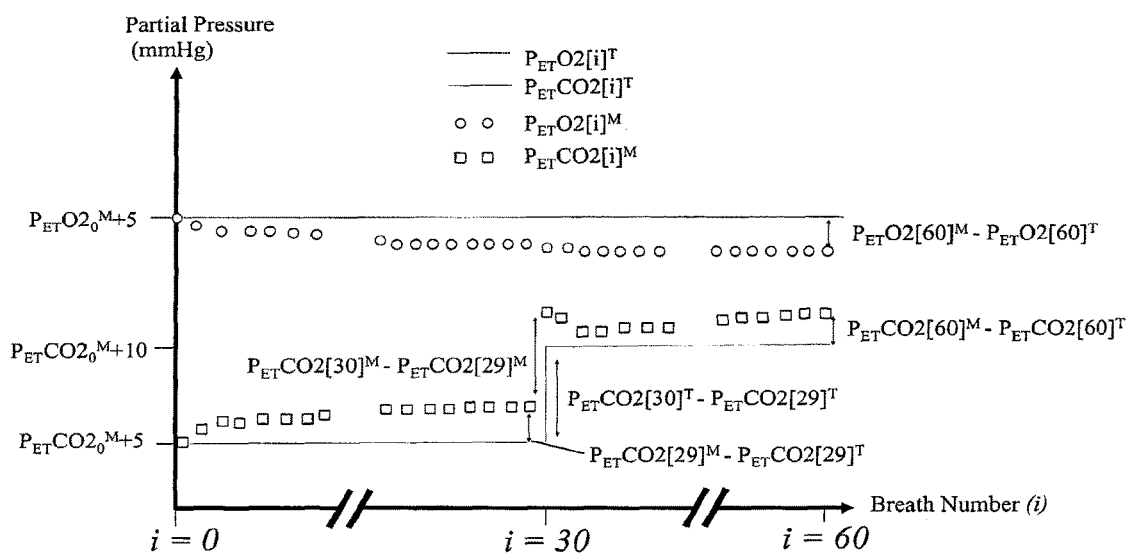
FIG. 6 is a graphic representation of a tuning sequence and observed errors that can be used to tune model parameters.

As illustrated in FIG. 6, with reference to examples of gas X (oxygen and carbon dioxide) parameters representing inputs for computation of $F_I X$ can be tuned so that the measured end-tidal partial pressures of O2 ($P_{ET}O2[i]^M$) and the measured end-tidal partial pressures of CO2 ($P_{ET}CO2[i]^M$) during any sequence more closely reflect the target end-tidal partial pressures of O2 ($P_{ET}O2[i]^T$) and the target end-tidal partial pressures of CO2 ($P_{ET}CO2[i]^T$). To tune the system parameters, standardized tuning sequences are run and the measured results compared to the targets. The difference between measured end-tidal partial pressures and the target end-tidal partial pressures in the standardized tuning sequences can be used to refine the estimates of some physiological parameters.

The tuning sequence optionally sets the target end-tidal partial pressure of O2 ($P_{ET}O2[i]^T$) at 5 mmHg above the baseline end-tidal partial pressure of O2 ($P_{ET}O2_0^M$) throughout the sequence, and executes a 5 mmHg step-change in the end-tidal partial pressure of CO2 ($P_{ET}CO2[i]^T$) from 5 mmHg above the baseline end-tidal partial pressure of CO2 ($P_{ET}CO2_0^M$) to 10 mmHg above the baseline end-tidal partial pressure of CO2 in breath 30 (i=30) of the sequence.

Embodiments of mass balance equations:

No SGD:

$$F_I X[i] = \frac{P_{ET}X[i]^T \cdot (FRC + V_T) - P_{ET}X[i-1]^T \cdot (FRC + V_D) - PB \cdot Q \cdot (1-s) \cdot T_B \cdot (C_{MV}X[i] - C_P X[i])}{(V_T - V_D) \cdot PB}$$

SGD:

$$F_I X[i] = \frac{(P_{ET}X[i]^T - P_{ET}X[i-1]^T) \cdot (FRC + V_T) + P_{ET}X[i-1]^T \cdot (FG_1 \cdot T_B) - PB \cdot Q \cdot (1-s) \cdot T_B \cdot (C_{MV}X[i] - C_P X[i])}{FG_1 \cdot T_B \cdot PB}$$

Abbreviations and terms are in FIG. 7.

Physiological Inputs

This section describes how to obtain measurements or estimates of all the physiological inputs required to execute a prospective end-tidal targeting sequence.

Subject Weight, Height, Age, and Sex:

Subject weight (W), height (H), age (A), and sex (G) can be obtained from a subject interview, an interview with a family member, from an attending physician, or from medical records. Weight and height can also be measured.

Bicarbonate:

The bicarbonate concentration ([$HCO_3$]) can be obtained from a blood gas measurement. If a blood gas measurement is not available or possible, it can be estimated as the middle of the normal range 24 mmol/L (9; 10).

Temperature:

Body temperature (T) can be obtained from a recent invasive or non-invasive measurement. If a measurement is not available or possible, it can be estimated as the middle of the normal range—37 C (11; 12).

Haemoglobin Concentration:

The haemoglobin concentration (Hb) can be obtained from a blood gas measurement. If a blood gas measurement is not available or possible, it can be estimated as the middle of the normal range for the subject's sex (G):

| | |
|---|---|
| 15 g/dL | for males |
| 13 g/dL | for females (10; 13) |

Shunt Fraction:

The intrapulmonary shunt fraction (s) can be measured using a variety of invasive and non-invasive techniques (14-17). If measurement is not available or possible, it can be estimated as the middle of the normal range—0.05 (18; 19).

Cardiac Output:

The cardiac output (Q) can be measured using a variety of invasive and non-invasive techniques (20-23). If measurement is not available or possible, it can be estimated from the subject's weight (W) according to the relationship:

$$Q = 10 \cdot (0.066 \cdot W + 1.4) \tag{24}$$

Breath Period:

The breath period ($T_B$) can be measured using a pressure transducer (PT) or flow transducer (FT) proximal to the subject's airway. Alternatively, the subject can be coached to breathe at a predetermined rate using a metronome or other prompter. If the subject is mechanically ventilated, this parameter can be determined from the ventilator settings or ventilator operator.

Recirculation Time:

The number of breaths for recirculation to occur ($n_R$) can be measured using a variety of invasive and non-invasive techniques (25-27). If measurement is not available or possible, it can be estimated from the breath period ($T_B$) and an average recirculation time (0.3 min) (28) according to the relationship:

$$n_R = 0.3/T_B$$

Metabolic O2 Consumption:

The overall metabolic O2 consumption (VO2) can be measured using a metabolic cart. If measurement is not available or possible, it can be estimated from the subject's weight (W), height (H), age (A), and sex (G) according to the relationship:

$$VO2 = \frac{10 \cdot W + 625 \cdot H - 5 \cdot A + 5}{6.8832} \text{ for males} \tag{29}$$

$$VO2 = \frac{10 \cdot W + 625 \cdot H - 5 \cdot A - 161}{6.8832} \text{ for females}$$

Metabolic CO2 Production:

The overall metabolic CO2 production (VCO2) can be measured using a metabolic cart. If measurement is not available or possible, it can be estimated from the overall metabolic O2 consumption (VO2) and average respiratory exchange ratio (0.8 ml CO2/ml O2) (30) according to the relationship:

$$VCO2 = 0.8 \cdot VO2$$

Functional Residual Capacity:

The functional residual capacity (FRC) can be measured using a variety of respiratory manoeuvres (31). If measurement is not available or possible, it can be estimated from the subject's height (H), age (A), and sex (G) according to the relationship:

$$FRC = (2.34 \cdot H + 0.01 \cdot A - 1.09) \cdot 1000 \text{ for males}$$

$$FRC = (2.24 \cdot H + 0.001 \cdot A - 1.00) \cdot 1000 \text{ for females} \tag{32}$$

Anatomical Dead Space:

The anatomical dead space ($V_D$) can be measured using a variety of respiratory manoeuvres (33-35). If measurement is not available or possible, it can be estimated from the subject's weight (W) and sex (G) according to the relationship:

$$V_D = 1.765 \cdot W + 32.16 \text{ for males}$$

$$V_D = 1.913 \cdot W + 21.267 \text{ for females} \tag{36}$$

Rate at which the controlled gas mixture is made available for inspiration when using a sequential gas delivery circuit (SGDC)

When using a sequential gas delivery circuit (SGDC), the rate at which the controlled gas mixture is made available for inspiration ($FG_1$) should be set so that the volume of the neutral gas inspired in each breath ($VG_2$) is greater than or equal to the anatomical dead space ($V_D$). The subject can be coached to increase their ventilation and/or the availability of the controlled gas mixture decreased until a sufficient volume of the neutral gas is observed to be inspired in each breath.

Tidal Volume:

The tidal volume ($V_T$) can be measured using a flow transducer (FT) proximal to the subject's airway. If measurement is not available or possible, in spontaneous breathers when using a sequential gas delivery circuit (SGDC), it can be estimated from the rate at which the controlled gas mixture ($G_1$) is made available for inspiration ($FG_1$), the breath period ($T_B$), and the anatomical dead space ($V_D$) according to the empirical relationship:

If $FG_1 < 15000$: $V_T = (0.75 \cdot FG_1 + 3750) \cdot T_B + V_D$ else: $V_T = FG_1 \cdot T_B + V_D$ Alternatively, the subject can be coached or trained to breathe to a defined volume using a prompter which measures the cumulative inspired volume and prompts the subject to stop inspiration when the defined volume has been inspired. If the subject is mechanically ventilated, this parameter can be determined from the ventilator settings or ventilator operator.

Target Sequence Input

The operator enters a target sequence of n breaths consisting of a target end-tidal partial pressures of O2 ($P_{ET}O2[i]^T$) and a target end-tidal partial pressure of CO2 ($P_{ET}CO2[i]^T$) for every breath (i) of the sequence.

Calculation of the Inspired Gas Composition to Induce Target End-Tidal Values

The partial pressure of O2 in the controlled gas mixture ($P_IO2[i]$) and the partial pressure of CO2 in the controlled gas mixture ($P_ICO2[i]$) required to induce the sequence of target end-tidal partial pressures of O2 ($P_{ET}O2[i]^T$) and target end-tidal partial pressures of CO2 ($P_{ET}CO2[i]^T$) can be calculated by executing the steps outlined in sections 6-15 for every breath of the sequence (i, i=1 ... n).

Calculate the O2 and CO2 Partial Pressures of Pulmonary End-Capillary Blood

When sequential rebreathing is employed (2; 37; 38), we assume that the partial pressure of O2 in pulmonary end-capillary blood ($P_pO2[i]$) is equal to the target end-tidal partial pressure of O2 ($P_{ET}O^2[i]^T$), and the partial pressure of CO2 in pulmonary end-capillary blood ($P_pCO2[i]$) is equal to the target end-tidal partial pressure of CO2 ($P_{ET}CO2[i]^T$) (39).

$$P_pO2[i] = P_{ET}O2[i]^T$$

$$P_pCO2[i] = P_{ET}CO2[i]^T$$

Various other formulas have been proposed to derive blood gas partial pressures from end-tidal partial pressures. For example, see (40; 41). Any of these relationships can be used in place of the above equalities.

Calculate the pH Pulmonary End-Capillary Blood

The pH of the pulmonary end-capillary blood (pH[i]) can be calculated from the Henderson Hasselbalch equation using the blood bicarbonate concentration ($[HCO_3]$), the blood CO2 partial pressure ($P_pCO2[i]$), and the solubility of CO2 in blood (0.03 mmol/L/mmHg) (9).

$$pH[i] = 6.1 + \log\left(\frac{[HCO_3]}{0.03 \cdot P_pCO2[i]}\right)$$

Calculate the O2 Saturation of Pulmonary End-Capillary Blood

The O2 saturation of pulmonary end-capillary blood ($S_pO2[i]$) can be calculated from experimental equations using the body temperature (T), the blood pH (pH[i]), the blood CO2 partial pressure ($P_pCO2[i]$), and the blood O2 partial pressure ($P_pO2[i]$) (42).

$$S_pO2[i] = 100 \cdot \frac{-8532.2289 \cdot z + 2121.401 \cdot z^2 - 67.073989 \cdot z^3 + z^4}{935960.87 - 31346.258 \cdot z + 2396.1674 \cdot z^2 - 67.104406 \cdot z^3 + z^4}$$

where $z = P_pO2[i] \cdot 10^{0.024 \cdot (37-T)+0.4 \cdot (pH[i]-7.4)+0.06 \cdot (\log 40 - \log P_pCO2[i])}$ Calculate the O2 Content of Pulmonary End-Capillary Blood The O2 content of pulmonary end-capillary blood ($C_pO2[i]$) can be calculated from the O2 saturation of the blood ($S_pO2[i]$), the blood haemoglobin concentration (Hb), the O2 carrying capacity of haemoglobin (1.36 ml/g), and the solubility of O2 in blood (0.003 ml/dL/mmHg) (43).

$$C_pO2[i] = 1.36 \cdot Hb \cdot \frac{S_pO2[i]}{100} + 0.003 \cdot P_pO2[i]$$

Alternative derivations of pH, O2 saturation, and O2 content are reviewed in detail in (44).

Calculate the CO2 Content of Pulmonary End-Capillary Blood

The CO2 content of pulmonary end-capillary blood ($C_pCO2[i]$) can be calculated from the blood haemoglobin concentration (Hb), the O2 saturation of the blood ($S_pO2[i]$), the blood pH (pH[i]), and the blood CO2 partial pressure ($P_pCO2[i]$) (45).

$$C_pCO2[i] = \left(1.0 - \frac{0.02924 \cdot Hb}{\left(2.244 - 0.422 \cdot \left(\frac{SpO2[i]}{100}\right)\right) \cdot (8.740 - pH[i])}\right) \cdot C_{pl}$$

where: $C_{pl} = 0.0301 \cdot P_pCO2[i] \cdot (1 + 10^{pH[i]-6.10}) \cdot 2.226$ See also (46-48) for alternative calculations of CO2 content.

Calculate the O2 and CO2 Content of Arterial Blood

The arterial blood is a mixture of the pulmonary end-capillary blood and the blood shunted past the lungs. The percentage of the cardiac output (Q) that is shunted past the lungs is given by the intrapulmonary shunt fraction (s).

The content of O2 in the arterial blood ($C_aO2[i]$) is a weighted average of the O2 content of the pulmonary end-capillary blood ($C_pO2[i]$) and the O2 content of the blood which is shunted directly from the mixed-venous circulation ($C_{MV}O2[i]$).

$$C_aO2[i] = (1-s) \cdot C_pO2[i] + s \cdot C_{MV}O2[i]$$

The content of CO2 in the arterial blood ($C_aCO2[i]$) is a weighted average of the CO2 content of the pulmonary end-capillary blood ($C_pCO2[i]$) and the CO2 content of the blood which is shunted directly from the mixed-venous circulation ($C_{MV}CO2[i]$).

$$C_aCO2[i] = (1-s) \cdot C_pCO2 + s \cdot C_{MV}CO2[i]$$

Calculate the O2 Content of the Mixed-Venous Blood

Before returning to the venous circulation, the arterial blood passes through the tissue capillary beds where O2 is consumed and exchanged. This system can be modelled as a compartmental system where each compartment (j) represents a single tissue or group of tissues. Each compartment is assigned a storage capacity for O2 ($dO2_j$). Each compartment is also modelled as being responsible for a fraction ($vo2_j$) of the overall metabolic O2 consumption (VO2), and receiving a fraction ($q_j$) of the total cardiac output (Q). The content of O2 in the venous blood leaving a compartment ($C_VO2[i]$) is equal to the content of O2 in the compartment. Assuming an O2 model with $n_{O2}$ compartments, the O2 content of the venous blood leaving each compartment can be calculated from the O2 content in the compartment during the previous breath ($C_VO2_j[i-1]$), the compartment parameters, and the period of the breath ($T_B$).

For j=1 ... $n_{O2}$ $$C_VO2_j[i] = C_VO2_j[i-1] + \frac{100 \cdot T_B}{dO2_j} \cdot (q_j \cdot Q \cdot (C_aO2[i] - C_VO2_j[i-1]) - vo2_j \cdot VO2)$$

The values for a one compartment model ($n_{O2}=1$) are given below. The model assumes a single compartment with a storage capacity for O2 ($dO2_k$) proportional to the subjects weight W) (49).

| j | $q_j$ | $dO2_j$ | $vo2_j$ |
|---|---|---|---|
| 1 | 1 | $(1500/70) \cdot W$ | 1 |

The mixed-venous O2 content leaving the tissues ($C_{MV(T)}O2[i]$) is the sum of the O2 content leaving each compartment ($C_VO2_j[i]$) weighted by the fraction of the cardiac output ($q_j$) received by the compartment.

$$C_{MV(T)}O2[i] = \sum_{j=1}^{n_{O2}} q_j \cdot C_V O2_j[i]$$

Alternatively, since the storage capacity of O2 in the tissues of the body is small, the O2 content of the mixed-venous blood leaving the tissues ($C_{MV(T)}O2[i]$) can be assumed to be equal to the arterial inflow of O2 to the tissues ($Q \cdot C_aO2_j[i]$) less the overall metabolic O2 consumption of the tissues (VO2) distributed over the cardiac output (Q).

$$C_{MV(T)}O2_j[i] = \frac{Q \cdot C_a O2[i] - VO2}{Q}$$

The O2 content of the mixed-venous blood entering the pulmonary circulation ($C_{MV}O2[i]$) is equal to the O2 content of the mixed-venous blood leaving the tissues delayed by the recirculation time ($C_{MV(T)}O2[i-n_R]$)

$$C_{MV}O2[i] = C_{MV(T)}O2[i-n_R]$$

Other O2 model parameters are available from (49; 50).

Calculate the CO2 Content of the Mixed-Venous Blood

Before returning to the venous circulation, the arterial blood passes through the tissue capillary beds where CO2 is produced and exchanged. This system can be modelled as a compartmental system where each compartment (k) represents a single tissue or group of tissues. Each compartment is assigned a storage capacity for CO2 ($dCO2_k$). Each compartment is also modelled as being responsible for a fraction ($vco2_k$) of the overall metabolic CO2 production (VCO2), and receiving a fraction ($q_k$) of the total cardiac output (Q). The content of CO2 in the venous blood leaving a compartment ($C_VCO2_k[i]$) is equal to the content of CO2 in the compartment. Assuming a CO2 model with $n_{CO2}$ compartments, the CO2 content of the venous blood leaving each compartment can be calculated from the CO2 content in the compartment during the previous breath ($C_VCO2_j[i-1]$), the compartment parameters, and the period of the breath ($T_B$).

For $k=1 \ldots n_{CO2}$ $$C_V CO2_k[i] = C_V CO2_k[i-1] + \frac{100 \cdot T_B}{dCO2_k} \cdot (vco2_k \cdot VCO2 - q_k \cdot Q \cdot (C_V CO2_k[i-1] - C_a CO2[i]))$$

The values for a five compartment model ($n_{CO2}=5$) are given below (51). The model assumes each compartment has a storage capacity for CO2 ($dCO2_k$) proportional to the subjects weight (W).

| k | $q_k$ | $dCO2_k$ | $vco2_k$ |
|---|---|---|---|
| 1 | 0.04 | $(225/70) \cdot W$ | 0.11 |
| 2 | 0.14 | $(902/70) \cdot W$ | 0.28 |
| 3 | 0.16 | $(9980/70) \cdot W$ | 0.17 |
| 4 | 0.15 | $(113900/70) \cdot W$ | 0.15 |
| 5 | 0.51 | $(3310/70) \cdot W$ | 0.29 |

The values for a one compartment model ($n_{CO2}=1$) are given below. The model assumes a single compartment with a storage capacity for CO2 ($dCO2_k$) proportional to the subjects weight (W). The storage capacity for the single compartment is calculated as the average of the storage capacity for each compartment of the multi-compartment model weighted by the fraction of the cardiac output assigned to the compartment.

| k | $q_k$ | $dCO2_k$ | $vco2_k$ |
|---|---|---|---|
| 1 | 1 | $(20505/70) \cdot W$ | 1 |

The mixed-venous CO2 content leaving the tissues ($C_{MV(T)}CO2[i]$) is the sum of the CO2 content leaving each compartment ($C_VCO2_k[i]$) weighted by the fraction of the cardiac output ($q_k$) received by the compartment.

$$C_{MV(T)}CO2[i] = \sum_{k=1}^{n_{CO2}} q_k \cdot C_V CO2_k[i]$$

The CO2 content of the mixed-venous blood entering the pulmonary circulation ($C_{MV}CO2[i]$) is equal to the CO2 content of the mixed-venous blood leaving the tissues delayed by the recirculation time ($C_{MV(T)}CO2[i-n_R]$)

$$C_{MV}CO2[i] = C_{MV(T)}CO2[i-n_R]$$

Other CO2 model parameters are available from (49; 52).

Calculate PIO2 and PICO2 to Deliver with no Sequential Gas Delivery Circuit

On each inspiration, a tidal volume ($V_T$) of gas is inspired into the alveoli. When the subject is not connected to a sequential gas delivery circuit, gas is inspired in the following order: a) the gas in the anatomical dead space ($V_D$) is re-inspired with a partial pressure of O2 equal to the target end-tidal partial pressure of O2 from the previous breath ($P_{ET}O2[i-1]^T$) and a partial pressure of CO2 equal to the target end-tidal partial pressure of CO2 from the previous breath ($P_{ET}CO2[i-1]^T$); b) a volume of controlled gas mixture ($VG_1$) with controllable partial pressure of O2 ($P_IO2[i]$) and controllable partial pressure of CO2 ($P_ICO2[i]$). This inspired gas mixes with the volume of gas in the functional residual capacity (FRC) with a partial pressure of O2 and CO2 equal to the target end-tidal partial pressures from the previous breath.

A volume of O2 is transferred between the alveolar space and the pulmonary circulation $VB_{O2}[i]$). The rate of O2 transfer between the alveolar space and the pulmonary circulation depends on the product of the cardiac output (Q) less the intrapulmonary shunt fraction (s), and the difference between the mixed-venous O2 content entering the pulmonary circulation ($C_{MV}O2[i]$) and the pulmonary end-capillary O2 content ($C_pO2[i]$) leaving the pulmonary circulation. This transfer occurs over the breath period ($T_B$).

$$VB_{O2}[i]=Q \cdot (1-s) \cdot T_B \cdot (C_{MV}O2[i] - C_pO2[i])$$

A volume of CO2 is transferred between the alveolar space and the pulmonary circulation ($VB_{CO2}[i]$). The rate of CO2 transfer between the alveolar space and the pulmonary circulation depends on the product of the cardiac output (Q) less the intrapulmonary shunt fraction (s), and the difference between the mixed-venous CO2 content entering the pulmonary circulation ($C_{MV}CO2[i]$) and the pulmonary end-capillary CO2 content ($C_pCO2[i]$) leaving the pulmonary circulation. This transfer occurs over the breath period ($T_B$).

$$VB_{CO2}[i]=Q \cdot (1-s) \cdot T_B \cdot (C_{MV}CO2[i] - C_pCO2[i])$$

The average volume of the controlled gas mixture inspired into the alveoli in each breath ($VG_1$) is given by the tidal volume ($V_T$) less the anatomical dead space ($V_D$).

$$VG_1 = V_T - V_D$$

The end-tidal partial pressure O2 ($P_{ET}O2[i]^T$) is simply the total volume of O2 in the alveolar space, divided by the total volume of the alveolar space. The end-tidal partial pressure CO2 ($P_{ET}CO2[i]^T$) is simply the total volume of CO2 in the alveolar space, divided by the total volume of the alveolar space.

$$P_{ET}O2[i]^T = \frac{\left(\overbrace{P_{ET}O2[i-1]^T \cdot FRC}^{O2\ in\ FRC} + \overbrace{P_{ET}O2[i-1]^T \cdot V_D}^{O2\ re-inspired\ from\ V_D} + \overbrace{P_IO2[i] \cdot (V_T - V_D)}^{O2\ in\ controlled\ gas\ mixture} + \overbrace{PB \cdot Q \cdot (1-s) \cdot T_B \cdot (C_{MV}O2[i] - C_pO2[i])}^{O2\ transferred\ into\ lung\ from\ the\ circulation\ (VB_{O2})}\right)}{\underbrace{V_T + FRC}_{Total\ volume\ of\ the\ alveolar\ space}}$$

$$P_{ET}CO2[i]^T = \frac{\left(\overbrace{P_{ET}CO2[i-1]^T \cdot FRC}^{CO2\ in\ FRC} + \overbrace{P_{ET}CO2[i-1]^T \cdot V_D}^{CO2\ re-inspired\ from\ V_D} + \overbrace{P_ICO2[i] \cdot (V_T - V_D)}^{CO2\ in\ controlled\ gas\ mixture} + \overbrace{PB \cdot Q \cdot (1-s) \cdot T_B \cdot (C_{MV}CO2[i] - C_pCO2[i])}^{CO2\ transferred\ into\ lung\ from\ the\ circulation\ (VB_{CO2})}\right)}{\underbrace{V_T + FRC}_{Total\ volume\ of\ the\ alveolar\ space}}$$

Since all of these volumes and partial pressures are either known, or can be estimated, the partial pressure of O2 in the controlled gas mixture ($P_IO2[i]$) and the partial pressure of CO2 in the controlled gas mixture ($P_ICO2[i]$) can be set to induce target end-tidal partial pressures.

In some cases, some of the terms (braced terms in the numerator of the above equations) contributing to the target end-tidal partial pressure of O2 ($P_{ET}O2[i]^T$) or the target end-tidal partial pressure of CO2 ($P_{ET}CO2[i]^T$) may be neglected. For example, in most cases, the O2 or CO2 re-inspired from the anatomical dead space ($V_D$) is small compared to the O2 or CO2 in the other volumes that contribute to the end-tidal partial pressures. In a case where the volume of $O_2$ or $CO_2$ in the controlled gas mixture is very large, for example when trying to induce a large increase in the target end-tidal partial pressures, the $O_2$ or $CO_2$ transferred into the lung from the circulation may be comparatively small and neglected. Neglecting any terms of the mass balance equations will decrease computational complexity at the expense of the accuracy of the induced end-tidal partial pressures of gases.

After re-arranging the above equations for the partial pressure of O2 in the controlled gas mixture and the partial pressure of CO2 in the controlled gas mixture, simplification, and grouping of terms:

$$P_IO2[i] = \frac{P_{ET}O2[i]^T \cdot (FRC + V_T) - P_{ET}O2[i-1]^T \cdot (FRC + V_D) - PB \cdot Q \cdot (1-s) \cdot T_B \cdot (C_{MV}O2[i] - C_pO2[i])}{V_T - V_D}$$

$$P_ICO2[i] = \frac{P_{ET}CO2[i]^T \cdot (FRC + V_T) - P_{ET}CO2[i-1]^T \cdot (FRC + V_D) - PB \cdot Q \cdot (1-s) \cdot T_B \cdot (C_{MV}CO2[i] - C_pCO2[i])}{V_T - V_D}$$

These equations can be used to calculate the partial pressure of O2 in the controlled gas mixture ($P_IO2[i]$) and the partial pressure of CO2 in the controlled gas mixture ($P_ICO2[i]$) required to induce a target end-tidal partial pressure of O2 ($P_{ET}O2[i]^T$) and target end-tidal partial pressure of CO2 ($P_{ET}CO2[i]^T$) where the target end-tidal partial pressure of O2 from the previous breath ($P_{ET}O2[i-1]^T$), the target end-tidal partial pressure of CO2 from the previous breath ($P_{ET}CO2[i-1]^T$), the functional residual capacity (FRC), the anatomical dead space ($V_D$), tidal volume ($V_T$), the breath period ($T_B$), cardiac output (Q), intrapulmonary shunt fraction (s), mixed-venous content of O2 entering the pulmonary circulation ($C_{MV}O2[i]$), mixed-venous content of CO2 entering the pulmonary circulation ($C_{MV}CO2[i]$), pulmonary end-capillary content of O2 ($C_pO2[i]$), and pulmonary end-capillary content of CO2 ($C_pCO2[i]$) are either known, calculated, estimated, measured, or predicted.

Notice that the partial pressure of O2 in the controlled gas mixture ($P_IO2[i]$) and the partial pressure of CO2 in the controlled gas mixture ($P_ICO2[i]$) required to induce a target end-tidal partial pressure of O2 ($P_{ET}O2[i]^T$) or a target end-tidal partial pressure of CO2 ($P_{ET}CO2[i]^T$) depends strongly on the tidal volume ($V_T$), anatomical dead space ($V_D$), and the functional residual capacity (FRC).

It is often useful in practise to maintain the end-tidal partial pressures of gases steady for a predefined number of breaths or period of time. This is a special case of inducing target end-tidal partial pressures of gases where the target end-tidal partial pressure of a gas in a breath is equal to the target end-tidal partial pressure of said gas from the previous breath.

$$P_{ET}O2[i]^T = P_{ET}O2[i-1]^T \text{ OR}$$

$$P_{ET}CO2[i]^T = P_{ET}CO2[i-1]^T$$

Herein, the above general equations for calculating the composition of the controlled gas mixture reduce to the following:

$$P_I O2[i] = \frac{P_{ET}O2[i]^T \cdot (V_T - V_D) - PB \cdot Q \cdot (1-s) \cdot T_B \cdot (C_{MV}O2[i] - C_p O2[i])}{V_T - V_D}$$

$$P_I CO2[i] = \frac{P_{ET}CO2[i]^T \cdot (V_T - V_D) - PB \cdot Q \cdot (1-s) \cdot T_B \cdot (C_{MV}CO2[i] - C_p CO2[i])}{V_T - V_D}$$

Notice, these equations still require the estimation, measurement, or determination of many of the subject's ventilatory or pulmonary parameters, namely, tidal volume ($V_T$), functional residual capacity (FRC), breath period ($T_B$), and anatomical dead space ($V_D$). Therefore, in the absence of sequential rebreathing, the calculation of the partial pressure of $O_2$ in the controlled gas mixture ($P_I O2[i]$) and the partial pressure of $CO2$ in the controlled gas mixture ($P_I CO2[i]$) required to induce a target end-tidal partial pressure of $O_2$ ($P_{ET}O2[i]^T$) and a target end-tidal partial pressure of $CO_2$ ($P_{ET}CO2[i]^T$) is highly dependant on the subjects ventilatory and pulmonary parameters. However, some of these parameters, namely functional residual capacity (FRC) and the anatomical dead space ($V_D$), can be measured or estimated prior to execution of the targeting sequence, and can be reasonably assumed not to change over the course of the experiment. Other parameters, namely tidal volume ($V_T$) and breath period ($T_B$), while normally highly variable, are very well controlled and stable in mechanically ventilated subjects.

This method, therefore, is optional, especially where a simpler approach is preferred, and the subject's ventilation can be reasonably controlled or predicted.

It will be recognized that the volumes and partial pressures required to calculate the partial pressure of $O_2$ in the controlled gas mixture ($P_I O2[i]$) and the partial pressure of $CO_2$ in the controlled gas mixture ($P_I CO2[i]$) may need to be corrected for differences in temperature or presence of water vapour between the lung and the conditions under which they are measured, estimated, or delivered. The corrections applied will depend on the conditions under which these volumes and partial pressures are measured, estimated, or delivered. All volumes and partial pressures should be corrected to body temperature and pressure saturated conditions. A person skilled in the art will be comfortable with these corrections.

A person skilled in the art will also recognize the equivalence between partial pressures and fractional concentrations. Any terms expressed as partial pressures can be converted to fractional concentrations and vice-versa. For example, the partial pressure of O2 in the controlled gas mixture ($P_I O2[i]$) and the partial pressure of CO2 in the controlled gas mixture $P_I CO2[i]$) may be converted a fractional concentration of O2 in the controlled gas mixture $F_I O2[i]$) and a fractional concentration of CO2 in the controlled gas mixture ($F_I CO2[i]$).

$$F_I O2[i] = \frac{P_I O2[i]}{PB}$$

$$F_I CO2[i] = \frac{P_I CO2[i]}{PB}$$

Calculate PIO2 and PICO2 to Deliver to a Sequential Gas Delivery Circuit

On each inspiration, a tidal volume ($V_T$) of gas is inspired into the alveoli. When the subject is connected to a sequential gas delivery circuit (SGDC) that collects previously expired gas in a reservoir for later inspiration as neutral gas (ex. Hi-Ox$_{SR}$), gas is inspired in the following order: a) the gas in the anatomical dead space ($V_D$) is re-inspired with a partial pressure of O2 equal to the target end-tidal partial pressure of O2 from the previous breath ($P_{ET}O2[i-1]^T$) and a partial pressure of CO2 equal to the target end-tidal partial pressure of $CO_2$ from the previous breath ($P_{ET}CO2[i-1]^T$); b) a volume of controlled gas mixture ($VG_1$) with controllable partial pressure of $O_2$ ($P_I O2[i]$) and controllable partial pressure of CO2 ($P_I CO2[i]$); c) a volume of neutral gas ($VG_2$) with a partial pressure of O2 and CO2 equal to the target end-tidal partial pressures from the previous breath. This inspired gas mixes with the volume of gas in the functional residual capacity (FRC) with a partial pressure of O2 and CO2 equal to the target end-tidal partial pressures from the previous breath.

A volume of O2 is transferred between the alveolar space and the pulmonary circulation ($VB_{O2}[i]$). The rate of O2 transfer between the alveolar space and the pulmonary circulation depends on the product of the cardiac output (Q) less the intrapulmonary shunt fraction (s), and the difference between the mixed-venous O2 content entering the pulmonary circulation $C_{MV}O2[i]$) and the pulmonary end-capillary O2 content ($C_p O2[i]$) leaving the pulmonary circulation. This transfer occurs over the breath period ($T_B$).

$$VB_{O2}[i] = Q \cdot (1-s) \cdot T_B \cdot (C_{MV}O2[i] - C_p O2[i])$$

A volume of CO2 is transferred between the alveolar space and the pulmonary circulation ($VB_{CO2}[i]$). The rate of CO2 transfer between the alveolar space and the pulmonary circulation depends on the product of the cardiac output (Q) less the intrapulmonary shunt fraction (s), and the difference between the mixed-venous CO2 content entering the pulmonary circulation ($C_{MV}CO2[i]$) and the pulmonary end-capillary CO2 content ($C_p CO2[i]$) leaving the pulmonary circulation. This transfer occurs over the breath period ($T_B$).

$$VB_{CO2}[i] = Q \cdot (1-s) \cdot T_B \cdot (C_{MV}CO2[i] - C_p CO2[i])$$

Assuming a neutral gas at least fills the subject's anatomical dead space ($V_D$), the average volume of the controlled gas mixture inspired into the alveoli in each breath ($VG_1$) is given by the rate at which the controlled gas mixture is made available for inspiration ($FG_1$) delivered over a single breath period ($T_B$):

$$VG_1 = FG_1 \cdot T_B$$

The average volume of neutral gas that is inspired into the alveoli in each breath is given by the tidal volume ($V_T$) less the volume of inspired controlled gas mixture ($VG_1$) and the volume of gas that remains in the anatomical dead space ($V_D$):

$$VG_2 = V_T - V_D - FG_1 \cdot T_B$$

The end-tidal partial pressure O2 ($P_{ET}O2[i]^T$) is simply the total volume of O2 in the alveolar space, divided by the total volume of the alveolar space. The end-tidal partial pressure CO2 ($P_{ET}CO2[i]^T$) is simply the total volume of CO2 in the alveolar space, divided by the total volume of the alveolar space.

$$P_{ET}O2[i]^T = \frac{\left(\overbrace{P_{ET}O2[i-1]^T \cdot FRC}^{\text{O2 in FRC}} + \overbrace{P_{ET}O2[i-1]^T \cdot V_D}^{\substack{\text{O2 re-inspired} \\ \text{from } V_D}} + \overbrace{P_I O2[i] \cdot (FG_1 \cdot T_B)}^{\substack{\text{O2 in controlled} \\ \text{gas mixture}}} + \overbrace{P_{ET}O2[i-1]^T \cdot (V_T - V_D - FG_1 \cdot T_B)}^{\text{O2 in neutral gas}} + \right.}{\underbrace{V_T + FRC}_{\text{Total volume of the alveolar space}}}$$

$$\left.\overbrace{PB \cdot Q \cdot (1-s) \cdot T_B \cdot (C_{MV}O2[i] - C_p O2[i])}^{\substack{\text{O2 transfered into lung from} \\ \text{the circulation } (VB_{O2})}}\right)$$

$$P_{ET}CO2[i]^T = \frac{\left(\overbrace{P_{ET}CO2[i-1]^T \cdot FRC}^{\text{CO2 in FRC}} + \overbrace{P_{ET}CO2[i-1]^T \cdot V_D}^{\substack{\text{CO2 re-inspired} \\ \text{from } V_D}} + \overbrace{P_I CO2[i] \cdot (FG_1 \cdot T_B)}^{\substack{\text{CO2 in controlled} \\ \text{gas mixture}}} + \overbrace{P_{ET}CO2[i-1]^T \cdot (V_T - V_D - FG_1 \cdot T_B)}^{\text{CO2 in neutral gas}} + \right.}{\underbrace{V_T + FRC}_{\text{Total volume of the alveolar space}}}$$

$$\left.\overbrace{PB \cdot Q \cdot (1-s) \cdot T_B \cdot (C_{MV}CO2[i] - C_p CO2[i])}^{\substack{\text{CO2 transfered into lung from} \\ \text{the circulation } (VB_{CO2})}}\right)$$

Since all of these volumes and partial pressures are either known, or can be estimated, the partial pressure of O2 in the controlled gas mixture ($P_I O2[i]$) and the partial pressure of CO2 in the controlled gas mixture ($P_I CO2[i]$) can be set to induce target end-tidal partial pressures.

In some cases, some of the terms (braced terms in the numerator of the above equations) contributing to the target end-tidal partial pressure of O2 ($P_{ET}O2[i]^T$) or the target end-tidal partial pressure of CO2 ($P_{ET}CO2[i]^T$) may be neglected. For example, in most cases, the $O_2$ or $CO_2$ re-inspired from the anatomical dead space ($V_D$) is small compared to the $O_2$ or $CO_2$ in the other volumes that contribute to the end-tidal partial pressures. In the case where the volume of O2 or CO2 in the controlled gas mixture is very large, for example when trying to induce a large increase in the target end-tidal partial pressures, the O2 or CO2 transferred into the lung from the circulation may be comparatively small and neglected. Neglecting any terms of the mass balance equations will decrease computational complexity at the expense of the accuracy of the induced end-tidal partial pressures of gases.

After re-arranging the above equations for the partial pressure of O2 in the controlled gas mixture and the partial pressure of CO2 in the controlled gas mixture, simplification, and grouping of terms:

$$P_I O2[i] = \frac{\begin{array}{c}(P_{ET}O2[i]^T - P_{ET}O2[i-1]^T) \cdot (FRC + V_T) + \\ P_{ET}O2[i-1]^T \cdot (FG_1 \cdot T_B) - PB \cdot Q \cdot \\ (1-s) \cdot T_B \cdot (C_{MV}O2[i] - C_p O2[i])\end{array}}{FG_1 \cdot T_B}$$

-continued $$P_I CO2[i] = \frac{\begin{array}{c}(P_{ET}CO2[i]^T - P_{ET}CO2[i-1]^T) \cdot (FRC + V_T) + \\ P_{ET}CO2[i-1]^T \cdot (FG_1 \cdot T_B) - PB \cdot Q \cdot \\ (1-s) \cdot T_B \cdot (C_{MV}CO2[i] - C_p O2[i])\end{array}}{FG_1 \cdot T_B}$$

The above equations can be used to calculate the partial pressure of O2 in the controlled gas mixture ($P_I O2[i]$) and the partial pressure of CO2 in the controlled gas mixture ($P_I CO2[i]$) required to induce a target end-tidal target partial pressure of O2 ($P_{ET}O2[i]^T$) and a target end-tidal partial pressure of CO2 ($P_{ET}CO2[i]^T$) where the target end-tidal partial pressure of O2 from the previous breath ($P_{ET}O2[i-1]^T$), the target end-tidal partial pressure of CO2 from the previous breath ($P_{ET}CO2[i-1]^T$), the functional residual capacity (FRC), tidal volume ($V_T$), rate at which the controlled gas mixture is made available for inspiration ($FG_1$), the breath period ($T_B$), cardiac output (Q), intrapulmonary shunt fraction (s), recirculation time ($n_R$), mixed-venous content of O2 entering the pulmonary circulation ($C_{MV}O2[i]$), mixed-venous content of CO2 entering the pulmonary circulation ($C_{MV}CO2[i]$), pulmonary end-capillary content of O2 ($C_p O2[i]$), and pulmonary end-capillary content of CO2 ($C_p CO2[i]$) are either known, calculated, estimated, measured, or predicted.

Notice that where this form sequential rebreathing is employed, the anatomical dead space ($V_D$) does not factor into the above equations and end-tidal targeting is independent of its measurement or estimation. Notice also that the tidal volume ($V_T$) appears only in summation with the functional residual capacity (FRC). Since the tidal volume is, in general, small compared to the functional residual capacity ($V_T \leq 0.1 \cdot FRC$), errors in measurement or estimation of the tidal volume have little effect on inducing target end-tidal partial pressures of gases. In fact, the above equations can be used with the tidal volume term omitted completely with little effect on results.

It is often useful in practise to maintain the end-tidal partial pressures of gases steady for a predefined number of breaths or period of time. This is a special case of inducing target end-tidal partial pressures of gases where the target end-tidal partial pressure of a gas in a breath is equal to the target end-tidal partial pressure of said gas from the previous breath.

$$P_{ET}O2[i]^T = P_{ET}O2[i-1]^T \text{ OR}$$

$$P_{ET}CO2[i]^T = P_{ET}CO2[i-1]^T$$

Herein, the above general equations for calculating the composition of the controlled gas mixture reduce to the following:

$$P_I O2[i] = \frac{P_{ET}O2[i]^T \cdot FG_1 - PB \cdot Q \cdot (1-s) \cdot (C_{MV}O2[i] - C_p O2[i])}{FG_1}$$

$$P_I CO2[i] = \frac{P_{ET}CO2[i]^T \cdot FG_1 - PB \cdot Q \cdot (1-s) \cdot (C_{MV}CO2[i] - C_p CO2[i])}{FG_1}$$

Notice, these equations do not require the estimation, measurement, or determination of any of the subject's ventilatory or pulmonary parameters, namely, tidal volume ($V_T$), functional residual capacity (FRC), breath period ($T_B$), or anatomical dead space ($V_D$).

The reduced or eliminated sensitivity of the equations to the subject's ventilatory parameters makes this method useful in practise with spontaneously breathing subjects. It is, however, not limited to spontaneously breathing subjects, and may also be used in mechanically ventilated subjects.

A person skilled in the art will recognize that the volumes and partial pressures required to calculate the partial pressure of O2 in the controlled gas mixture ($P_I O2[i]$) and the partial pressure of CO2 in the controlled gas mixture ($P_I CO2[i]$) may need to be corrected for differences in temperature or presence of water vapour between the lung and the conditions under which they are measured, estimated, or delivered. The corrections applied will depend on the conditions under which these volumes and partial pressures are measured, estimated, or delivered. All volumes and partial pressures should be corrected to body temperature and pressure saturated conditions. A person skilled in the art will be comfortable with these corrections.

A person skilled in the art will also recognize the equivalence between partial pressures and fractional concentrations. Any terms expressed as partial pressures can be converted to fractional concentrations and vice-versa. For example, the partial pressure of O2 in the controlled gas mixture ($P_I O2[i]$) and the partial pressure of CO2 in the controlled gas mixture ($P_I CO2[i]$) may be converted a fractional concentration of O2 in the controlled gas mixture ($F_I O2[i]$) and a fractional concentration of CO2 in the controlled gas mixture ($F_I CO2[i]$).

$$F_I O2[i] = \frac{P_I O2[i]}{PB}$$

$$F_I CO2[i] = \frac{P_I CO2[i]}{PB}$$

Determine if Targets are Logistically Feasible

In practise, many different implementations of gas delivery devices and sequential gas delivery circuits may be used. In general, it is logistically feasible to induce the target end-tidal partial pressures for the current breath ($P_{ET}O2[i]^T$, $P_{ET}CO2[i]^T$) if:

1) The required partial pressures of gases in the controlled gas mixture are physically realizable:

$$0 \leq P_I O2[i] \leq PB \qquad \text{a)}$$

$$0 \leq P_I CO2[i] \leq PB \qquad \text{b)}$$

$$P_I O2[i] + P_I CO2[i] \leq PB \qquad \text{c)}$$

2) The gas delivery device is capable of delivering a controlled mixture of the desired composition at the required flow rate Where sequential rebreathing is carried out with a Hi-Ox$_{SR}$ sequential gas delivery circuit and a gas blender:

Assuming $n_{SG}$ source gases ($SG_1 \ldots SG_{n_G}$) are blended to deliver the required mixture to the Hi-Ox$_{SR}$ sequential gas delivery circuit (SGDC). Each gas (m) contains a known fractional concentration of O2 ($fo2_m$) and a known fractional concentration of CO2 ($fco2_m$). The flow rate of each gas ($FSG_m[i]$) required to deliver the total desired flow rate of the controlled gas ($FG_1$) with the required partial pressure of O2 ($P_I O2[i]$) and the required partial pressure of CO2 ($P_I CO2[i]$) can be determined by solving the following set of equations:

$$\sum_{m=1}^{n_{SG}} FSG_m[i] = FG_1$$

$$\sum_{m=1}^{n_{SG}} fo2_m \cdot FSG_m[i] = \frac{P_I O2[i]}{PB} \cdot FG_1$$

$$\sum_{m=1}^{n_{SG}} fco2_m \cdot FSG_m[i] = \frac{P_I CO2[i]}{PB} \cdot FG_1$$

The target end-tidal partial pressures for the current breath ($P_{ET}O2[i]^T$, $P_{ET}CO2[i]^T$) are logistically feasible if:

$$0 \leq P_I O2[i] \leq PB \qquad \text{1)}$$

$$0 \leq P_I CO2[i] \leq PB \qquad \text{2)}$$

$$P_I O2[i] + P_I CO2[i] \leq PB \qquad \text{3)}$$

4) There exists a solution to the above system of equations, and $$FSG_m[i] \geq 0 \, \forall_m \qquad \text{5)}$$

6) The gas blender is capable of delivering a controlled mixture of the desired composition at the required flow rate It is therefore required that $n_{SG} \geq 3$. It is computationally optimal to have $n_{SG} = 3$.

One possible set of gases is:

$SG_1$: $fco2_1=0, fo2_1=1$ $SG_2$: $fco2_2=1, fo2_2=0$ $SG_3$: $fco2_3=0, fo2_3=0$ It may enhance the safety of the system to use gases with a minimal concentration of O2 and maximum concentration of CO2. In this case, a possible set of gases is:

$SG_1$: $fco2_1=0, fo2_1=0.1$ $SG_2$: $fco2_2=0.4, fo2_2=0.1$ $SG_3$: $fco2_3=0, fo2_3=1$ The balance of the source gases when not entirely composed of O2 and CO2 can be made up of any gas or combination of gases, which may vary depending on the context. The balance of the source gases is most often made up of N2 because it is physiologically inert.

Adjusting Parameters to Make Logistically Infeasible Targets Logistically Feasible:

It may occur that inducing a target end-tidal partial pressure of O2 ($P_{ET}O2[i]^T$) or a target end-tidal partial pressure of CO2 ($P_{ET}CO2[i]^T$) in a given breath is not logistically feasible. This may occur because the partial pressure of O2 in the controlled gas mixture ($P_IO2[i]$) or the partial pressure of CO2 in the controlled gas mixture ($P_ICO2[i]$) required to induce the target end-tidal partial pressure of O2 or the target end-tidal partial pressure of CO2 is either not physically realizable, or there does not exist a blend of the current source gases ($SG_1 \ldots SG_{n_G}$) resulting in the required the partial pressure of O2 in the controlled gas mixture and the required partial pressure of CO2 in the controlled gas mixture. If the composition of the controlled gas mixture is not physically realizable for a given set of targets, the targets may be modified and/or the rate at which the controlled gas mixture is made available to the circuit ($FG_1$) modified, or where applicable, the tidal volume ($V_T$) modified, until the composition is physically realizable. If the composition of the controlled gas mixture is physically realizable for a given set of targets, but no combination of the source gases results in the required composition, the targets may be modified and/or the rate at which the controlled gas mixture is made available to the circuit modified, or where applicable, the tidal volume ($V_T$) modified, and/or different source gases used.

If $P_IO2[i]<0$—The target end-tidal partial pressure of O2 ($P_{ET}O2[i]^T$) is not logistically feasible because the partial pressure of O2 in the controlled gas mixture ($P_IO2[i]$) required to induce the target end-tidal partial pressure of O2 is not physically realizable. To make induction of the target logistically feasible, increase the target end-tidal partial pressure of O2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_IO2[i]>PB$—The target end-tidal partial pressure of O2 ($P_{ET}O2[i]^T$) is not logistically feasible because the partial pressure of O2 in the controlled gas mixture ($P_IO2[i]$) required to induce the target end-tidal partial pressure of O2 is not physically realizable. To make induction of the target logistically feasible, decrease the target end-tidal partial pressure of O2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_ICO2[i]<0$—The target end-tidal partial pressure of CO2 ($P_{ET}CO2[i]^T$) is not logistically feasible because the partial pressure of CO2 in the controlled gas mixture ($P_ICO2[i]$) required to induce the target end-tidal partial pressure of CO2 is not physically realizable. To make induction of the target logistically feasible, decrease the target end-tidal partial pressure of CO2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_ICO2[i]>PB$—The target end-tidal partial pressure of CO2 ($P_{ET}CO2[i]^T$) is not logistically feasible because the partial pressure of CO2 in the controlled gas mixture ($P_ICO2[i]$) required to induce the target end-tidal partial pressure of CO2 is not physically realizable. To make induction of the target logistically feasible, decrease the target end-tidal partial pressure of CO2. Alternatively, where sequential rebreathing is used, the rate at which the controlled gas mixture is made available to the circuit ($FG_1$) may be modified. Where sequential rebreathing is not used, the tidal volume ($V_T$) may be modified.

If $P_IO2[i]+P_ICO2[i]>PB$—The combination of the target end-tidal partial pressure of O2 ($P_{ET}O2[i]^T$ and the target end-tidal partial pressure of CO2 ($P_{ET}CO2[i]^T$) is not logistically feasible because the combination of the partial pressure of O2 in the controlled gas mixture ($P_IO2[i]$) and the partial pressure of CO2 in the controlled gas mixture ($P_ICO2[i]$) required to induce the targets is not physically realizable. To make induction of the targets logistically feasible, decrease the target end-tidal partial pressure of O2 and/or the target end-tidal partial pressure of CO2. Alternatively, where sequential rebreathing is used, the rate at which the controlled gas mixture is made available to the circuit ($FG_1$) may be modified. Where sequential rebreathing is not used, the tidal volume ($V_T$) may be modified.

If there does not exist a solution to the above system of equations, or there exists a solution for which $FSG_m[i]<0$ for any m, then the current source gases ($SG_1 \ldots SG_{n_G}$) cannot be blended to create the controlled gas mixture. Different source gases must be used to induce the end-tidal target of O2 ($P_{ET}O2[i]^T$) and the end-tidal target of CO2 ($P_{ET}CO2[i]^T$), or the desired targets must be changed. Alternatively, it may be possible to modify the rate at which the controlled gas mixture is made available to the circuit ($FG_1$) until the partial pressure of O2 in the controlled gas mixture ($P_IO2[i]$) and the partial pressure of CO2 in the controlled gas mixture ($P_ICO2[i]$) required to induce the targets are realizable with the current source gases.

Often, the rate at which the controlled gas mixture is made available to the circuit ($FG_1$) is modified to make a target end-tidal partial pressure of O2 ($P_{ET}O2[i]^T$) or a target end-tidal partial pressure of CO2 ($P_{ET}CO2[i]^T$) logistically feasible to induce. However, the rate at which the controlled gas mixture is made available to the circuit should not be increased to a rate beyond which the subject fails to consistently exhaust the supply of the controlled gas mixture in each breath. This maximal rate varies between subjects. However, it is not necessary that the rate at which the controlled gas mixture is made available to the circuit be the same in every breath. Therefore, the rate at which the controlled gas mixture is made available to the circuit may be set to some basal value for most breaths, and only increased in particular breaths in which the inducing the target end-tidal partial pressures is not logistically feasible at the basal rate of flow. The basal rate at which the controlled gas mixture is made available to the circuit should be a rate at which the subject can comfortably, without undo ventilatory effort, exhaust the supply of the controlled gas mixture in each breath. The maximal rate at which the controlled gas mixture is made available to the circuit should be the maximum rate at which the subject can consistently exhaust the supply of the controlled gas mixture in each breath with a maximal ventilatory effort. The subject may be prompted to increase their ventilatory effort in breaths where the rate at which the controlled gas mixture is made available to the circuit is increased.

Initializing the System

Let the index [0] represent the value of a variable for all breaths before the start of the sequence (all values of i≤0). To initialize the system, the subject is allowed to breathe freely, without intervention, until the measured end-tidal partial pressure of O2 ($P_{ET}CO2^M$) and the measured end-tidal partial pressure of CO2 ($P_{ET}CO2^M$) are stable—these are taken as the baseline partial pressure of O2 ($P_{ET}O2_0^M$) and the baseline partial pressure of CO2 ($P_{ET}CO2_0^M$). The measured end-tidal partial pressures are considered stable when there is less than ±5 mmHg change in the measured end-tidal partial pressure of O2 and less than ±2 mmHg change in the measured end-tidal partial pressure of CO2 over 3 consecutive breaths. The rest of the variables are initialized by assuming the whole system has equilibrated to a steady state at the baseline end-tidal partial pressures.

Assume that end-tidal partial pressures are equal to the baseline measurements:

$$P_{ET}O2[0]^T = P_{ET}O2_0^M$$

$$P_{ET}CO2[0]^T = P_{ET}CO2_0^M$$

Assume pulmonary end-capillary partial pressures are equal to end-tidal partial pressures:

$$P_pO2[0] = P_{ET}O2[0]^T$$

$$P_pCO2[0] = P_{ET}CO2[0]^T$$

Calculate O2 Blood Contents Assuming Steady State:
Pulmonary End-Capillary O2 Saturation:

$$pH[0] = 6.1 + \log\left(\frac{[HCO_3]}{0.03 \cdot P_pCO2[0]}\right)$$

$$S_pO2[0] = 100 \cdot \frac{-8532.2289 \cdot z + 2121.401 \cdot z^2 - 67.073989 \cdot z^3 + z^4}{935960.87 - 31346.258 \cdot z + 2396.1674 \cdot z^2 - 67.104406 \cdot z^3 + z^4}$$

where $z = P_pO2[0] \cdot 10^{0.024 \cdot (37-T) + 0.4 \cdot (pH[0] - 7.4) + 0.06 \cdot (\log 40 - \log P_pCO2[0])}$ Pulmonary End-Capillary O2 Content:

$$C_pO2[0] = 1.36 \cdot Hb \cdot \frac{S_pO2[0]}{100} + 0.003 \cdot P_pO2[0]$$

Mixed-Venous O2 Content:

$$C_{MV(T)}O2[0] = C_pO2[0] - \frac{VO2}{(1-s) \cdot Q}$$

$$C_{MV}O2[0] = C_{MV(T)}O2[0]$$

Arterial O2 Content:

$$C_aO2[0] = (1-s) \cdot C_pO2[0] + s \cdot C_{MV}O2[0]$$

O2 Content of Each Compartment in the Model:
For j=1 ... $n_{O2}$ $$C_VO2_j[0] = C_aO2[0] - \frac{vo2_j \cdot VO2}{q_j \cdot Q}$$

Calculate CO2 Blood Contents Assuming Steady State:
Pulmonary End-Capillary CO2 Content:

$$C_pCO2[0] = \left(1.0 - \frac{0.02924 \cdot Hb}{\left(2.244 - 0.422 \cdot \left(\frac{SpO2[0]}{100}\right)\right) \cdot (8.740 - pH[0])}\right) \cdot C_{pl}$$

$$C_{pl} = 0.0301 \cdot P_pCO2[0] \cdot (1 + 10^{pH[0] - 6.10}) \cdot 2.226$$

Mixed-Venous CO2 Content:

$$C_{MV(T)}CO2[0] = C_pCO2[0] + \frac{VCO2}{(1-s) \cdot Q}$$

$$C_{MV}CO2[0] = C_{MV(T)}CO2[0]$$

Arterial CO2 Content:

$$C_aCO2[0] = (1-s) \cdot C_pCO2[0] + s \cdot C_{MV}CO2[0]$$

CO2 Content of Each Compartment in the Model:
For k=1 ... $n_{CO2}$ $$C_VCO2_k[0] = C_aCO2[0] + \frac{vco2_k \cdot VCO2}{q_k \cdot Q}$$

Tuning the System

The parameters of the system can be tuned so that the measured end-tidal partial pressures of O2 ($P_{ET}O2[i]^M$) and the measured end-tidal partial pressures of CO2 ($P_{ET}CO2[i]^M$) during any sequence more closely reflect the target end-tidal partial pressures of O2 ($P_{ET}O2[i]^T$) and target end-tidal partial pressures of CO2 ($P_{ET}CO2[i]^T$). To tune the system parameters, standardized tuning sequences are run and the measured results compared to the targets. The difference between measured end-tidal partial pressures and the target end-tidal partial pressures in the standardized tuning sequences can be used to refine the estimates of some physiological parameters.

Example Tuning Sequence:

The tuning sequence sets the target end-tidal partial pressure of O2 ($P_{ET}O2[i]^T$) at 5 mmHg above the baseline end-tidal partial pressure of O2 ($P_{ET}O2_0^M$) throughout the sequence, and executes a 5 mmHg step-change in the end-tidal partial pressure of CO2 ($P_{ET}CO2[i]^T$) from 5 mmHg above the baseline end-tidal partial pressure of CO2 ($P_{ET}CO2_0^M$) to 10 mmHg above the baseline end-tidal partial pressure of CO2 in breath 30 (i=30) of the sequence.

$$P_{ET}O2[i]^T = P_{ET}O2_0^M + 5 \quad i = 1 \ldots 60$$

$$P_{ET}CO2[i]^T = P_{ET}CO2_0^M + 5 \quad i = 1 \ldots 29$$

$$P_{ET}CO2[i]^T = P_{ET}CO2_0^M + 10 \quad i = 30 \ldots 60$$

The estimate of the functional residual capacity (FRC) can be refined as a function of the difference between the actual step change induced in the end-tidal CO2 ($P_{ET}CO2[30]^M - P_{ET}CO2[29]^M$) and the target step-change ($P_{ET}CO2[30]^T - P_{ET}CO2[29]^T = 5$) in breath 30 (i=30).

$$FRC = FRC_0 + \alpha((P_{ET}CO2[30]^M - P_{ET}CO2[29]^M) - (P_{ET}CO2[30]^T - P_{ET}CO2[29]^T))$$

$\alpha = 200$ ml/mmHg

In general, the correction factor ($\alpha$) can range from 50-500 ml/mmHg. Lower values of the correction factor will produce a more accurate estimate of the functional residual capacity (FRC) while requiring more tuning iterations. Higher values will reduce the number of tuning iterations but may cause the refined estimate of the parameter to oscillate around the optimal value.

The estimate of the overall metabolic O2 consumption (VO2) can be refined as a function of the difference between the target end-tidal partial pressure of O2 ($P_{ET}O2[60]^T$) and the measured end-tidal partial pressure of O2 ($P_{ET}O2[60]^M$) in breath 60 (i=60).

$$VO2 = VO2_0 - \beta(P_{ET}O2[60]^M - P_{ET}O2[60]^T) \quad \beta = 10 \text{ ml/min/mmHg}$$

In general, the correction factor ($\beta$) can range from 5-200 ml/min/mmHg. Lower values of the correction factor will produce a more accurate estimate of the overall metabolic O2 consumption (VO2) while requiring more tuning iterations. Higher values will reduce the number of tuning iterations but may cause the refined estimate of the parameter to oscillate around the optimal value.

The estimate of the overall metabolic CO2 production (VCO2) can be refined as a function of the difference between the target end-tidal partial pressure of CO2 ($P_{ET}CO2[29]^T$) and the measured end-tidal partial pressure of CO2 ($P_{ET}CO2[29]^M$) in breath 29 (i=29).

$$VCO2 = VCO2_0 + \gamma(P_{ET}CO2[29]^M - P_{ET}CO2[29]^T) \quad \gamma = 10 \text{ ml/min/mmHg}$$

Alternatively, the estimate of the overall metabolic CO2 production (VCO2) can be refined as a function of the difference between the target end-tidal partial pressure of CO2 ($P_{ET}CO2[60]^T$) and the measured end-tidal partial pressure of CO2 ($P_{ET}CO2[60]^M$) in breath 60 (i=60)

$$VCO2 = VCO2_0 + \gamma(P_{ET}CO2[60]^M - P_{ET}CO2[60]^T) \quad \gamma = 10 \text{ ml/min/mmHg}$$

In general, the correction factor ($\gamma$) can range from 5-200 ml/min/mmHg. Lower values of the correction factor will produce a more accurate estimate of the overall metabolic CO2 production (VCO2) while requiring more tuning iterations. Higher values will reduce the number of tuning iterations but may cause the refined estimate of the parameter to oscillate around the optimal value.

General Requirements of a Tuning Sequence:

In breaths where the target end-tidal partial pressures of gases are transitioning between values, the estimate of the functional residual capacity (FRC) determines the magnitude of the change induced in the actual end-tidal tidal partial pressures of gases. The estimate of the overall metabolic O2 consumption (VO2) influences the induced/measured end-tidal partial pressure of O2 ($P_{ET}O2[i]^M$) in steady state. Similarly, the estimate of the overall metabolic CO2 production (VCO2) influences the induced/measured end-tidal partial pressure of CO2 ($P_{ET}CO2[i]^M$) in steady state.

It therefore follows that a difference between the measured change in the end-tidal partial pressure of O2 ($P_{ET}O2[i]^M - P_{ET}O2[i-1]^M$) and the targeted change in the end-tidal partial pressure of O2 ($P_{ET}O2[i]^T - P_{ET}O2[i-1]^T$) in breaths where the target end-tidal partial pressure of O2 is not equal to the target end-tidal partial pressure of O2 from the previous breath ($P_{ET}O2[i]^T \neq P_{ET}O2[i-1]^T$), or a difference between the measured change in the end-tidal partial pressure of CO2 ($P_{ET}CO2[i]^M - P_{ET}CO2[i-1]^M$) and the targeted change in the end-tidal partial pressure of CO2 ($P_{ET}CO2[i]^T - P_{ET}CO2[i-1]^T$) in breaths where the target end-tidal partial pressure of CO2 is not equal to the target end-tidal partial pressure of CO2 from the previous breath ($P_{ET}CO2[i]^T \neq P_{ET}CO2[i-1]^T$), reflect errors in the estimate of the functional residual capacity (FRC).

Conversely, differences between the target end-tidal partial pressure of O2 ($P_{ET}O2[i]^T$) and the measured end-tidal tidal partial pressure of O2 ($P_{ET}O2[i]^M$) in breaths at the end of a long (20 breath) period of constant target end-tidal partial pressures of O2 ($P_{ET}O2[i]^T = P_{ET}O2[i-1]^T$) reflect errors in the overall metabolic O2 consumption (VO2). It is assumed that the measured end-tidal partial pressures of O2 will have stabilized (less than ±5 mmHg change in the measured end-tidal partial pressure of O2 over 3 consecutive breaths), although not necessarily at the target end-tidal partial pressure of O2, after 20 breaths of targeting the same end-tidal partial pressures of O2. If, however, the measured end-tidal partial pressure of O2 has not stabilized after 20 breaths of targeting the same end-tidal partial pressures of O2, a longer duration of targeting the same end-tidal partial pressure of O2 should be used for tuning the overall metabolic consumption of O2.

Differences between the target end-tidal partial pressure of CO2 ($P_{ET}CO2[i]^T$) and the measured end-tidal tidal partial pressure of CO2 ($P_{ET}CO2[i]^M$) in breaths at the end of a long (20 breath) period of constant target end-tidal partial pressures of CO2 ($P_{ET}CO2[i]^T = P_{ET}CO2[i-1]^T$) reflect errors in the overall metabolic CO2 production (VCO2). It is assumed that the measured end-tidal partial pressures of CO2 will have stabilized (less than ±2 mmHg change in the measured end-tidal partial pressure of CO2 over 3 consecutive breaths), although not necessarily at the target end-tidal partial pressure of CO2, after 20 breaths of targeting the same end-tidal partial pressures of CO2. If, however, the measured end-tidal partial pressure of CO2 has not stabilized after 20 breaths of targeting the same end-tidal partial pressures of CO2, a longer duration of targeting the same end-tidal partial pressure of CO2 should be used for tuning the overall metabolic production of CO2.

The tuning sequence described above is only an example of one sequence that can be used to tune the estimates of the physiological parameters.

The functional residual capacity (FRC) can be tuned by observing the difference between the measured change in the end-tidal partial pressure of O2 ($P_{ET}O2[i]^M - P_{ET}O2[i-1]^M$) and the targeted change in the end-tidal partial pressure of O2 ($P_{ET}O^2[i]^T - P_{ET}O2[i-1]^T$) in breaths where the target end-tidal partial pressure of O2 is not equal to the target end-tidal partial pressure of O2 from the previous breath ($P_{ET}O2[i]^T \neq P_{ET}O2[i-1]^T$), or a difference between the measured change in the end-tidal partial pressure of CO2 ($P_{ET}CO2[i]^M - P_{ET}CO2[i-1]^M$) and the targeted change in the end-tidal partial pressure of CO2 ($P_{ET}CO2[i]^T - P_{ET}CO2[i-1]^T$) in breaths where the target end-tidal partial pressure of CO2 is not equal to the target end-tidal partial pressure of CO2 from the previous breath ($P_{ET}CO2[i]^T \neq P_{ET}CO2[i-1]^T$). Therefore, any sequence that targets the induction of a change in the end-tidal partial pressure of O2, or a change in the end-tidal partial pressure of CO2, can be used to tune the estimate of the functional residual capacity.

The overall metabolic consumption of O2 (VO2) can be tuned by observing the difference between the target end-tidal partial pressure of O2 ($P_{ET}O2[i]^T$) and the measured end-tidal tidal partial pressure of O2 ($P_{ET}O^2[i]^M$) in breaths at the end of a long (20 breath) period of constant target end-tidal partial pressures of O2 ($P_{ET}O2[i]^T=P_{ET}O2[i-1]^T$). It is assumed that the measured end-tidal partial pressures of O2 will have stabilized (less than ±5 mmHg change in the measured end-tidal partial pressure of O2 over 3 consecutive breaths), although not necessarily at the target end-tidal partial pressures of O2, after 20 breaths of targeting the same end-tidal partial pressures of O2. If, however, the measured end-tidal partial pressure of O2 has not stabilized after 20 breaths of targeting the same end-tidal partial pressures of O2, a longer duration of targeting the same end-tidal partial pressure of O2 should be used for tuning the overall metabolic consumption of O2. Therefore, any sequence that targets to maintain the end-tidal partial pressure of O2 constant for a sufficiently long duration may be used to tune the estimate of the overall metabolic consumption of O2.

The overall metabolic production of CO2 (VCO2) can be tuned by observing the difference between the target end-tidal partial pressure of CO2 ($P_{ET}CO2[i]^T$) and the measured end-tidal tidal partial pressure of CO2 ($P_{ET}CO2[i]^M$) in breaths at the end of a long (20 breath) period of constant target end-tidal partial pressures of CO2 ($P_{ET}CO2[i]^T=P_{ET}CO2[i-1]^T$). It is assumed that the measured end-tidal partial pressures of CO2 will have stabilized (less than ±2 mmHg change in the measured end-tidal partial pressure of CO2 over 3 consecutive breaths), although not necessarily at the target end-tidal partial pressure of CO2, after 20 breaths of targeting the same end-tidal partial pressures of CO2. If, however, the measured end-tidal partial pressure of CO2 has not stabilized after 20 breaths of targeting the same end-tidal partial pressures of CO2, a longer duration of targeting the same end-tidal partial pressure of CO2 should be used for tuning the overall metabolic production of CO2. Therefore, any sequence that targets to maintain the end-tidal partial pressure of CO2 constant for a sufficiently long duration may be used to tune the estimate of the overall metabolic production of CO2.

It is not required that all parameter estimates are tuned in the same sequence. Tuning of all parameters in the example sequence is done only for convenience. Different tuning sequences may be used to tune the estimates of different individual, or groups of, parameters.

Embodiments of Mass Balance Equations:
No SGD:

$$F_I X[i] = \frac{P_{ET}X[i]^T \cdot (FRC+V_T) - P_{ET}X[i-1]^T \cdot (FRC+V_D) - PB \cdot Q \cdot (1-s) \cdot T_B \cdot (C_{MV}X[i] - C_P X[i])}{(V_T - V_D) \cdot PB}$$

SGD:

$$F_I X[i] = \frac{(P_{ET}X[i]^T - P_{ET}X[i-1]^T) \cdot (FRC+V_T) + P_{ET}X[i-1]^T \cdot (FG_1 \cdot T_B) - PB \cdot Q \cdot (1-s) \cdot T_B \cdot (C_{MV}X[i] - C_P X[i])}{FG_1 \cdot T_B \cdot PB}$$

Figure 8A:
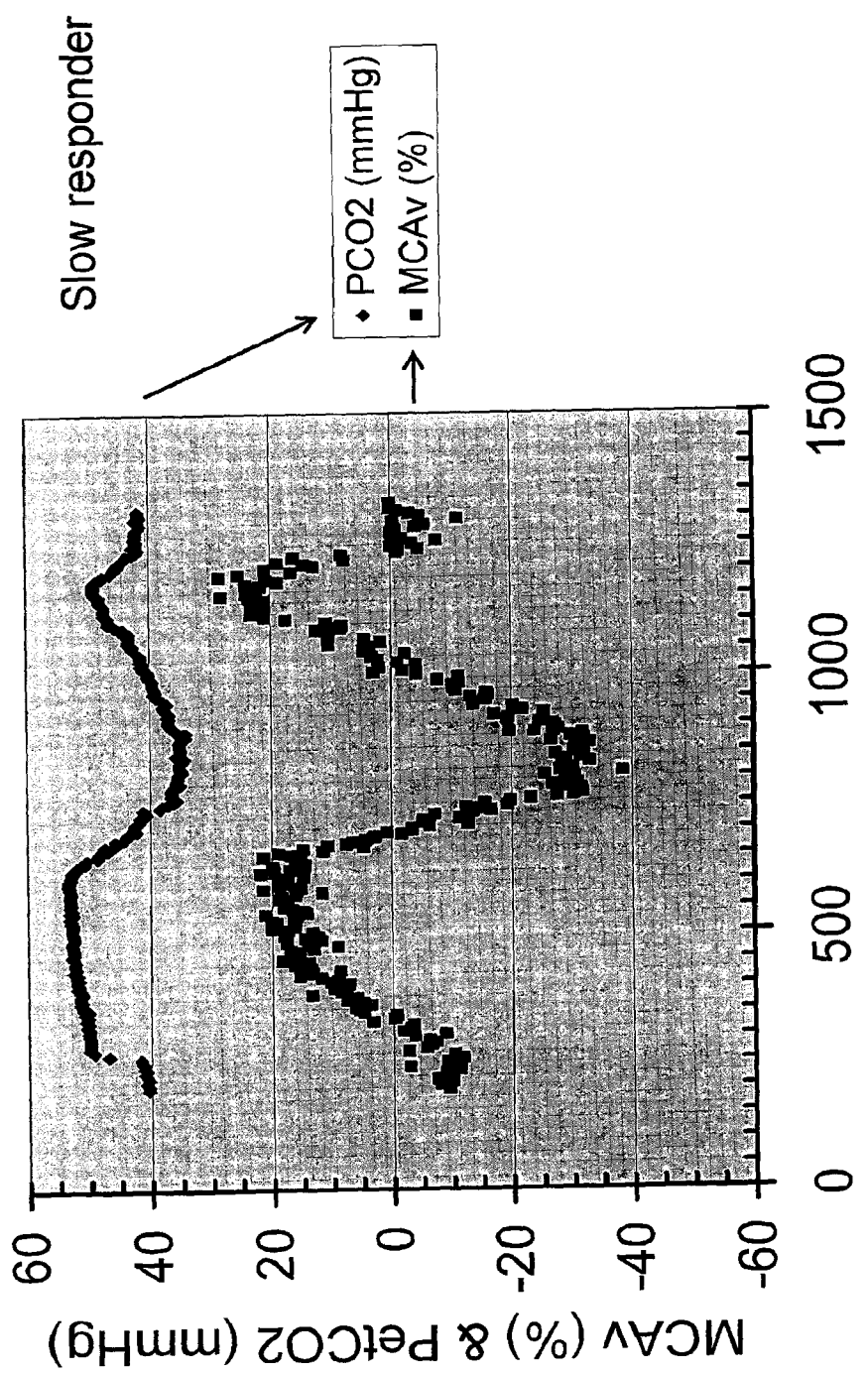
FIGS. 8a and 8b are graphical representations of changes in target end tidal values of CO2 and response—mid-cerebral artery blood flow velocity, for a slow responder and a fast responder as revealed by a ramp sequence.
Figure 8B:
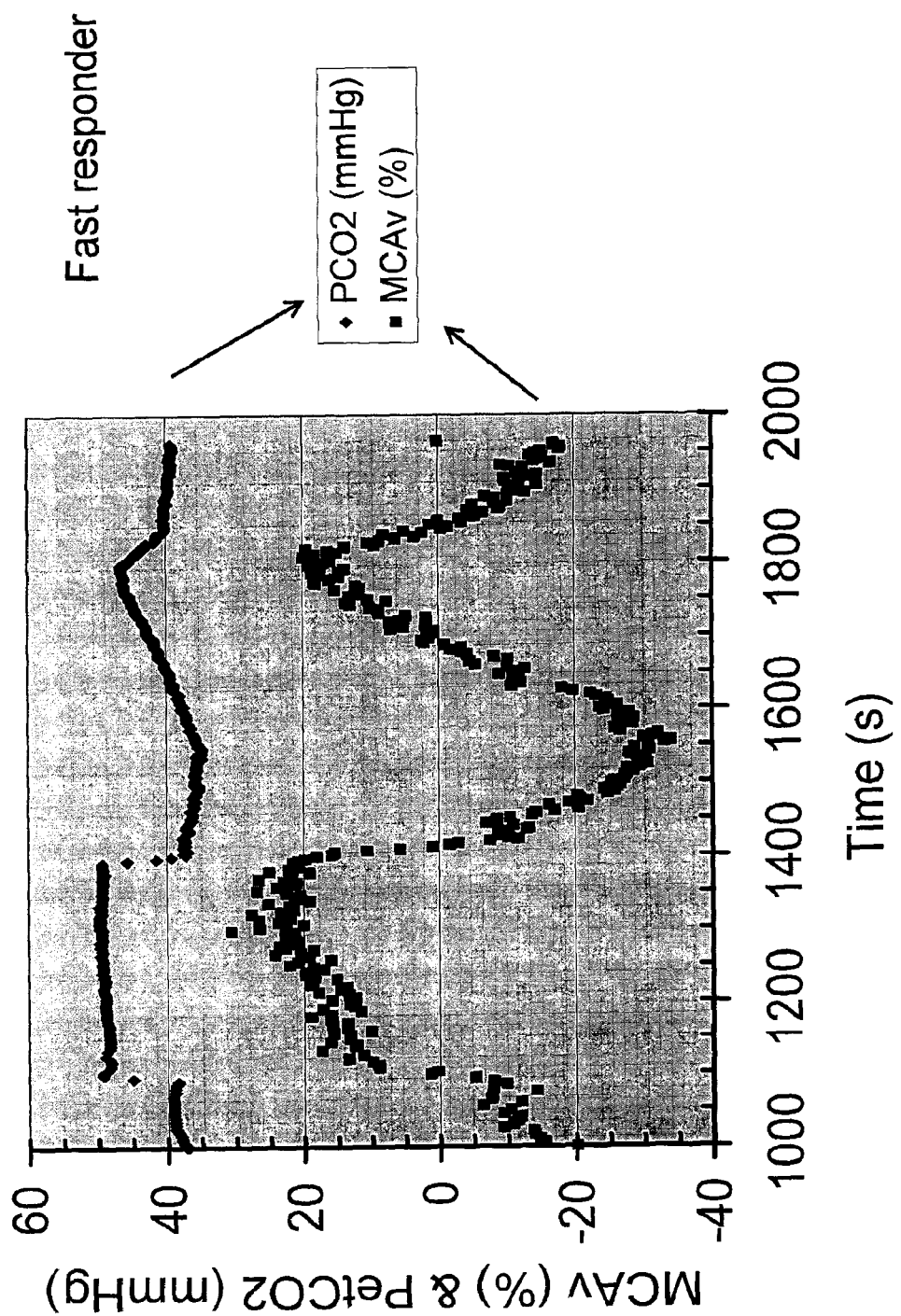

As seen in FIGS. 8a and 8b a ramp sequence reveals the sigmoidal nature of a pattern of a physiological response—mid-cerebral artery blood flow velocity—showing its sigmoidal nature over different time courses depending on whether the subject is a fast or slow responder.

Figure 9:
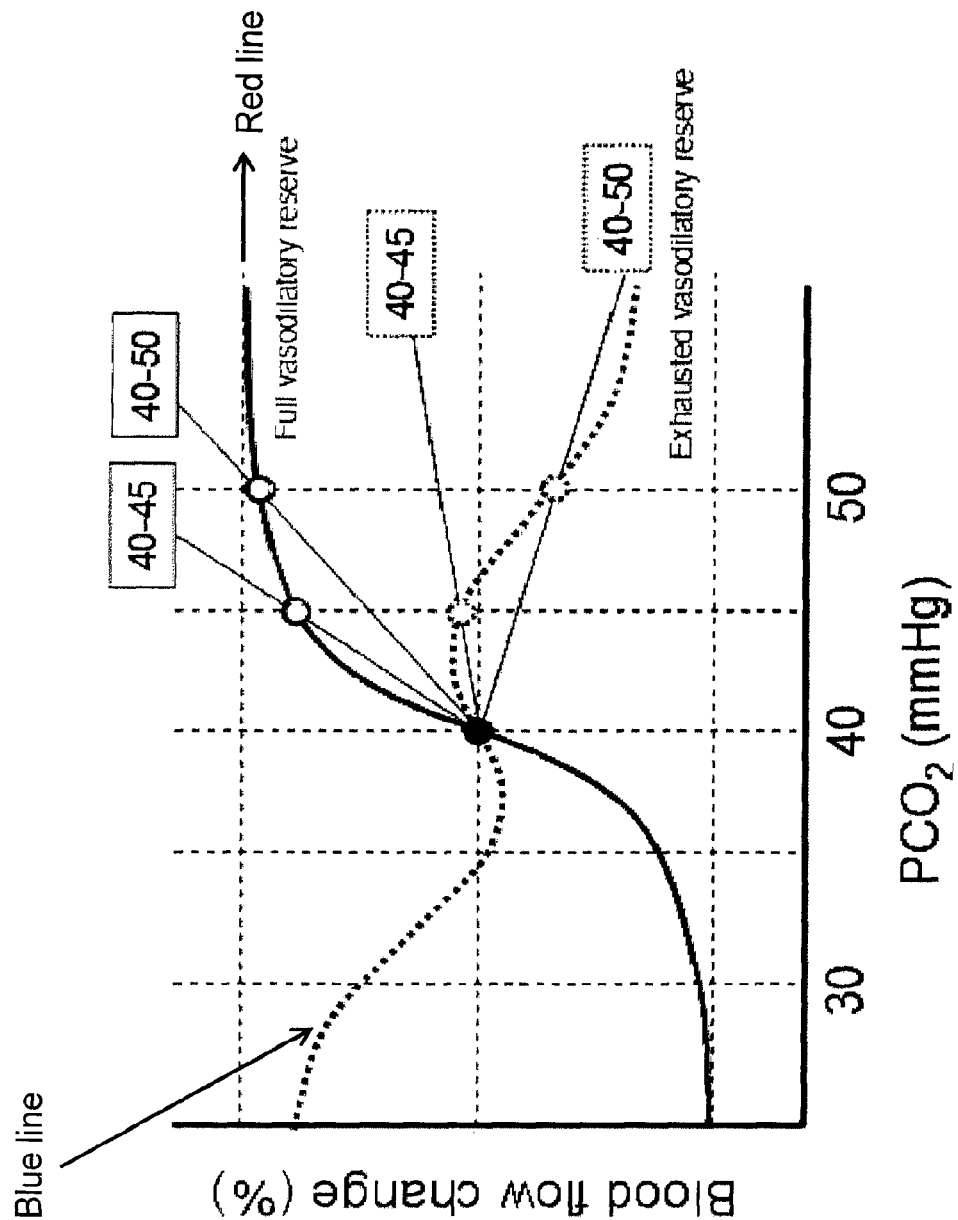
FIG. 9 is a graphical representation of blood flow responses to $PCO_2$ predicted for the model of a brain vascular territory with a partially-stenosed vessel branch and a healthy branch in parallel as revealed by a ramp sequence.

FIG. 9 blood flow responses to $PCO_2$ predicted for the model of a brain vascular territory with a partially-stenosed vessel branch and a healthy branch in parallel. Where there is some blood flow resistance upstream from the branches, it causes the partially-stenosed vessel to encroach on its vasodilatory reserve by an auto-regulatory mechanism. A vasodilatory stimulus such as in increase in arterial $CO_2$ will stimulate all vessels to dilate, but those vessels that have already dilated in response to the increase in upstream resistance have a reduced range of response. The solid red line in FIG. 9 depicts the sigmoidal response of a normal branch. The dotted blue line depicts the response of the partially stenosed vessel branch when coupled in parallel with the normal vessel branch, showing steal in hypercapnia and reverse steal in hypocapnia. The slopes of the straight lines show the predicted CVR values for $PCO_2$ stimulus ranges 40-45 and 40-50 mmHg. The filled circle marks the resting blood flow at resting $PCO_2$ and the open circles show the measured responses for a healthy territory (solid circles and line) and a territory perfused via a stenosed vessel (dotted circles and line).

FIG. 9 illustrates the sigmoidal relationship between regional blood flow and $PCO_2$ predicts that CVR in a vascular territory with adequate vasodilatory reserve will be greater for increases in $PCO_2$ from 40 to 45 mmHg vs. increases from 40 to 50 mmHg. By contrast, a vascular territory downstream from a hemodynamically significant stenosis may have a positive CVR when the $PCO_2$ change is in a range where some vasodilatory reserve is preserved, but, with a greater stimulus range such as 40-50 mmHg $PCO_2$, these vessels reach their vasodilatory limit and the continued vasodilatory capacity in other regions will induce steal.

The model outlined in FIG. 9 was investigated a comprehensive manner by using it to predict the change in CBF region by region in response to graded changes in $P_{ET}CO_2$ in a patient with steno-occlusive disease.

Figure 10:
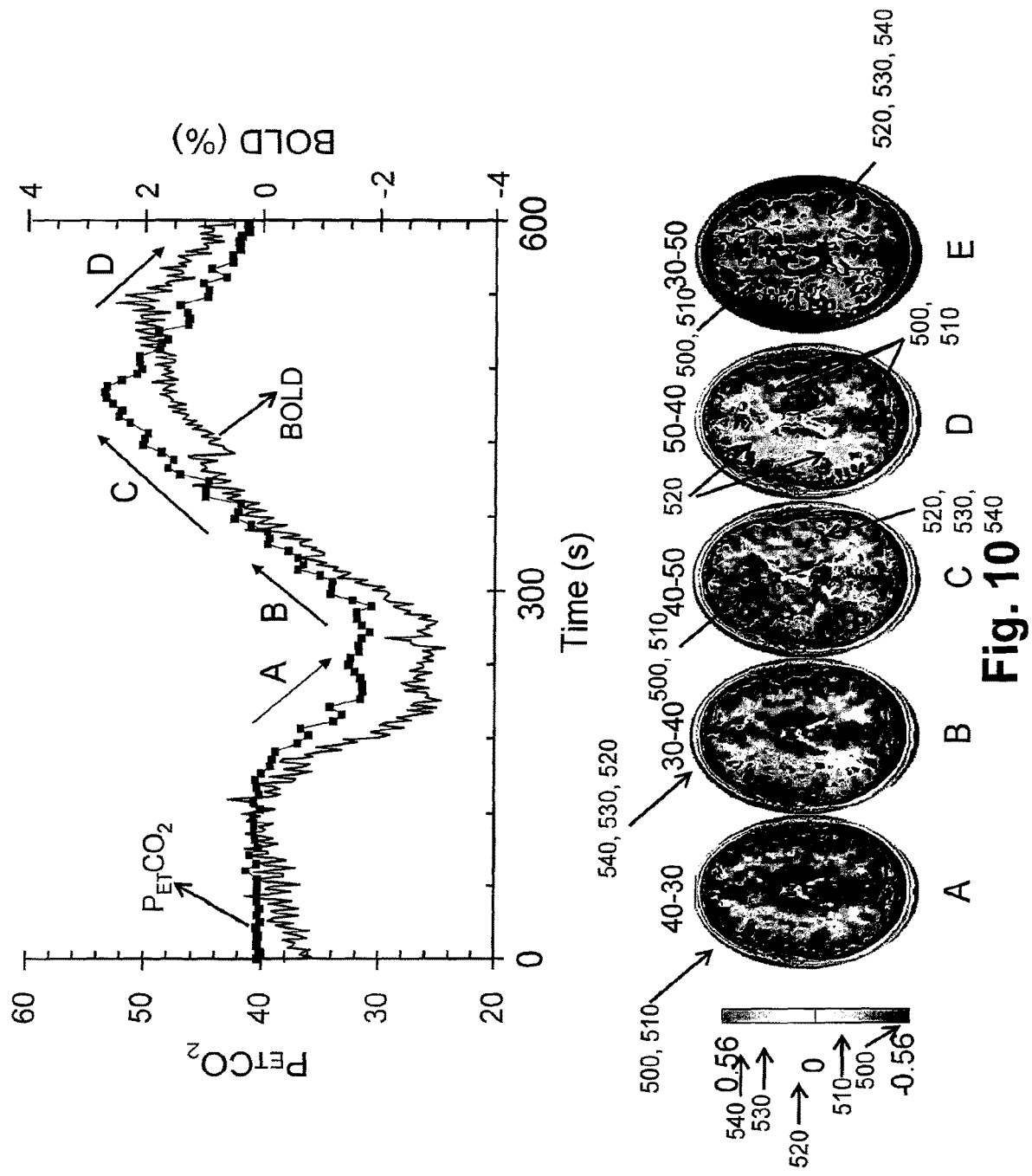
FIG. 10 is a graphical representation of a bold signal response to $PCO_2$ as revealed by a ramp sequence and corresponding CVR maps for an axial slice at different $PetCO_2$ ranges for a patient with moya moya disease.

FIG. 10 shows an example of the development of steal with hypercapnia, and reverse steal (Robin Hood effect) with hypocapnia [Lassen, 1968 #16325]. Both of these conditions were observed in the same patient, confirming that steal and reverse steal are a function of the changes taking place in the parallel branches of the vascular bed with intact cerebral autoregulation. The CVR map in response to a hypercapnic change in $P_{ET}CO_2$ from 30 to 50 mmHg is shown in FIG. 10A and colour coded with the scale shown. We interpret the blue colour of the right MCA territory as signifying a vascular bed with reduced vasodilatory reserve (presumably as a result of MCA stenosis). The CVR maps for an axial slice at different $P_{ET}CO_2$ ranges for a 18 year old male patient with moya moya disease affecting the right MCA territory are divided as follows (A) CVR map calculated for a hypocapnic $P_{ET}CO_2$ change from 40 to 30 mmHg. (B) CVR map calculated for a hypercapnic $P_{ET}CO_2$ change from 30 to 40 mmHg. (C) CVR map calculated for a hypercapnic $P_{ET}CO_2$ change from 40 to 50 mmHg. (D) CVR map calculated for a hypocapnic $P_{ET}CO_2$ change from 50 to 40 mmHg. (E) CVR map calculated over the full hypercapnic $P_{ET}CO_2$ change from 30 to 50 mmHg. In this subject, inducing a reduction of $P_{ET}CO_2$ from 40 mmHg to 30 mmHg produces a robust constriction in the healthy left brain territory and a decrease in the blood flow and BOLD signal (FIG. 10, CVR A). The CVR is color coded as before, but with the convention that its sign follows the BOLD change, so the CVR map is predominantly blue in the 'normal' vascular beds. However, a careful inspection of FIG. 10 (CVR A) shows some yellow and orange colouration in the right MCA territory, indicating areas of increasing blood flow and CVR due to reverse steal, as predicted by the model demonstrated in FIG. 9. With another change in the direction of the stimulus, the hypercapnic increase in $P_{ET}CO_2$ from 30 to 40 mmHg produces a large increase in flow in the healthy left MCA region, but a lesser increase in the compromised right MCA region (FIG. 10, CVR B). Within this range of $P_{ET}CO_2$ hypercapnia, the right MCA territory demonstrates some vasodilatory reserve. Nevertheless, as predicted and illustrated in FIG. 9, further hypercapnia to 50 mmHg results in a greater steal and the CVR values are negative, and the map is coloured blue (FIG. 10, CVR C). Finally, our conceptual model predicts that withdrawal of the vasodilatory stimulus will abolish the steal and induce a reverse steal via the Robin Hood effect. Once again, this result is observed in FIG. 10 (CVR D); this CVR map is virtually the reverse image of the CVR map calculated for the full range of 30 to 50 mmHg change in $P_{ET}CO_2$ (FIG. 10, CVR E). In FIG. 10 the BOLD signal vs. time is presented for the whole brain, an average value of all voxels.

EXAMPLE 1

An apparatus according to the invention was used to target end tidal gas concentrations of $CO_2$ and $O_2$ in 35 subjects. We targeted the following sequence (values attained in brackets): normocapnia (60 seconds a $PetCO_2$=40 mm Hg, SD=1 mm; $PetO_2$=100 mm Hg, SD=2 mm), Hypercapnia (60 seconds at $PetCO_2$=50 mm Hg, SD=1 mm; $PetO_2$=100 mm Hg, SD=2 mm), normocapnia (100 seconds), hypercapnia (180 seconds), and normocapnia (110 seconds). FIG. 11 comprises a partial raw data set for 6 subjects.

The content of all of the patent and scientific references herein is hereby incorporated by reference.

1. Robbins P A, Swanson G D, Howson M G. A prediction-correction scheme for forcing alveolar gases along certain time courses. J Appl Physiol 1982 May; 52(5):1353-1357. [cited 2011 Oct. 11]
2. Slessarev M, Han J, Mardimae A, Prisman E, Preiss D, Volgyesi G, Ansel C, Duffin J, Fisher J A. Prospective targeting and control of end-tidal CO2 and O2 concentrations. J. Physiol. (Lond.) 2007 June; 581(Pt 3):1207-1219. [cited 2011 Oct. 6]
3. Banzett R B, Garcia R T, Moosavi S H. Simple contrivance "clamps" end-tidal and despite rapid changes in ventilation. Journal of Applied Physiology 2000 May; 88(5):1597-1600. [cited 2011 Oct. 7]
4. Fisher J. Breathing circuits to facilitate the measurement of cardiac output during . . . [Internet]. [date unknown]; [cited 2011 Oct. 11] Available from: http://www.google.com/patents/about?id=RSqbAAAAEBAJ
5. Fisher J. Method of measuring cardiac related parameters non-invasively via the lung . . . [Internet]. [date unknown]; [cited 2011 Oct. 11] Available from: http://www.google.com/patents/about?id=QiqbAAAAEBAJ
6. Fisher J A. Method And Apparatus For Inducing And Controlling Hypoxia [Internet]. [date unknown]; [cited 2011 Oct. 11] Available from: http://www.google.com/patents/about?id=Cd7HAAAAEBAJ
7. Slessarev M. Method and Apparatus to Attain and Maintain Target End Tidal Gas Concentrations [Internet]. [date unknown]; [cited 2011 Oct. 11] Available from: http://www.google.com/patents/about?id=23XGAAAAEBAJ
8. Stenzler A. High FIO2 oxygen mask with a sequential dilution feature [Internet]. [date unknown]; [cited 2011 Oct. 11] Available from: http://www.google.com/patents/about?id=v1WIAAAAEBAJ
9. Bray J, Cragg P A, Macknight A, Mills R, Taylor D. Lecture Notes on Human Physiology. 4th ed. Wiley-Blackwell; 1999.
10. Kratz A, Lewandrowski K B. Case records of the Massachusetts General Hospital. Weekly clinicopathological exercises. Normal reference laboratory values. N. Engl. J. Med. 1998 October; 339(15):1063-1072. [cited 2011 Oct. 6]
11. Sund-Levander M, Forsberg C, Wahren L K. Normal oral, rectal, tympanic and axillary body temperature in adult men and women: a systematic literature review. Scand J Caring Sci 2002 June; 16(2):122-128. [cited 2011 Oct. 6]
12. Mackowiak P A, Wasserman S S, Levine M M. A critical appraisal of 98.6 degrees F., the upper limit of the normal body temperature, and other legacies of Carl Reinhold August Wunderlich. JAMA 1992 September; 268(12): 1578-1580. [cited 2011 Oct. 6]
13. Beutler E, Waalen J. The definition of anemia: what is the lower limit of normal of the blood hemoglobin concentration? Blood 2006 March; 107(5):1747-1750. [cited 2011 Oct. 6]
14. Peyton P J, Poustie S J, Robinson G J B, Penny D J, Thompson B. Non-invasive measurement of intrapulmonary shunt during inert gas rebreathing. Physiol Meas 2005 June; 26(3):309-316. [cited 2011 Oct. 6]
15. Peyton P J, Robinson G J B, McCall P R, Thompson B. Noninvasive measurement of intrapulmonary shunting. J. Cardiothorac. Vasc. Anesth. 2004 February; 18(1):47-52. [cited 2011 Oct. 6]
16. Hope D A, Jenkins B J, Willis N, Maddock H, Mapleson W W. Non-invasive estimation of venous admixture: validation of a new formula. Br J Anaesth 1995 May; 74(5):538-543. [cited 2011 Oct. 6]
17. Smith H L, Jones J G. Non-invasive assessment of shunt and ventilation/perfusion ratio in neonates with pulmonary failure. Arch. Dis. Child. Fetal Neonatal Ed. 2001 September; 85(2):F127-132. [cited 2011 Oct. 6]
18. Finley T N, Lenfant C, Haab P, Piiper J, Rahn H. Venous admixture in the pulmonary circulation of anestethetized dogs. J Appl Physiol 1960 May; 15:418-424.[cited 2011 Oct. 6]
19. Krowka M J, Cortese D A. Hepatopulmonary syndrome: an evolving perspective in the era of liver transplantation. Hepatology 1990 January; 11(1):138-142. [cited 2011 Oct. 6]
20. Reuter D A, Goetz A E. Measurement of cardiac output. Anaesthesist 2005 November; 54(11):1135-1151; quiz 1152-1153. [cited 2011 Oct. 6]
21. Ehlers K C, Mylrea K C, Waterson C K, Calkins J M. Cardiac output measurements. A review of current techniques and research. Ann Biomed Eng 1986; 14(3):219-239. [cited 2011 Oct. 6]
22. Geerts B F, Aarts L P, Jansen J R. Methods in pharmacology: measurement of cardiac output. Br J Clin Pharmacol 2011 March; 71(3):316-330. [cited 2011 Oct. 6]
23. Pugsley J, Lerner A B. Cardiac output monitoring: is there a gold standard and how do the newer technologies compare? Semin Cardiothorac Vasc Anesth 2010 December; 14(4):274-282. [cited 2011 Oct. 6]
24. Jegier W, Sekelj P, Auld P A, Simpson R, McGregor M. The relation between cardiac output and body size. Br Heart J 1963 July; 25:425-430. [cited 2011 Oct. 6]

25. Ross D N. Theophylline-ethylenediamine in the measurement of blood circulation time. Br Heart J 1951 January; 13(1):56-60. [cited 2011 Oct. 6]
26. Zubieta-Calleja G R, Zubieta-Castillo G, Paulev P-E, Zubieta-Calleja L. Non-invasive measurement of circulation time using pulse oximetry during breath holding in chronic hypoxia. J. Physiol. Pharmacol. 2005 September; 56 Suppl 4:251-256. [cited 2011 Oct. 6]
27. Sowton E, Bloomfield D, Jones N L, Higgs B E, Campbell E J. Recirculation time during exercise. Cardiovasc. Res. 1968 October; 2(4):341-345. [cited 2011 Oct. 6]
28. Chapman C B, Fraser R S. Studies on the effect of exercise on cardiovascular function. I. Cardiac output and mean circulation time. Circulation 1954 January; 9(1):57-62. [cited 2011 Oct. 6]
29. Mifflin M D, St Jeor S T, Hill L A, Scott B J, Daugherty S A, Koh Y O. A new predictive equation for resting energy expenditure in healthy individuals. Am. J. Clin. Nutr. 1990 February; 51(2):241-247. [cited 2011 Oct. 6]
30. Lenfant C. Time-dependent variations of pulmonary gas exchange in normal man at rest. J Appl Physiol 1967 April; 22(4):675-684. [cited 2011 Oct. 6]
31. Wanger J, Clausen J L, Coates A, Pedersen O F, Brusasco V, Burgos F, Casaburi R, Crapo R, Enright P, van der Grinten C P M, Gustafsson P, Hankinson J, Jensen R, Johnson D, Macintyre N, McKay R, Miller M R, Navajas D, Pellegrino R, Viegi G. Standardisation of the measurement of lung volumes. Eur. Respir. J. 2005 September; 26(3):511-522. [cited 2011 Oct. 6]
32. Stocks J, Quanjer P H. Reference values for residual volume, functional residual capacity and total lung capacity. ATS Workshop on Lung Volume Measurements. Official Statement of The European Respiratory Society. Eur. Respir. J. 1995 March; 8(3):492-506. [cited 2011 Oct. 6]
33. Arnold J H, Thompson J E, Arnold L W. Single breath $CO_2$ analysis: description and validation of a method. Crit. Care Med. 1996 January; 24(1):96-102. [cited 2011 Oct. 6]
34. Heller H, Könen-Bergmann M, Schuster K D. An algebraic solution to dead space determination according to Fowler's graphical method. Comput. Biomed. Res. 1999 April; 32(2):161-167. [cited 2011 Oct. 6]
35. Williams E M, Hamilton R M, Sutton L, Viale J P, Hahn C E. Alveolar and dead space volume measured by oscillations of inspired oxygen in awake adults. Am. J. Respir. Crit. Care Med. 1997 December; 156(6):1834-1839. [cited 2011 Oct. 6]
36. Hart M C, Orzalesi M M, Cook C D. Relation between anatomic respiratory dead space and body size and lung volume. Journal of Applied Physiology 1963 May; 18(3):519-522. [cited 2011 Oct. 6]
37. Ito S, Mardimae A, Han J, Duffin J, Wells G, Fedorko L, Minkovich L, Katznelson R, Meineri M, Arenovich T, Kessler C, Fisher J A. Non-invasive prospective targeting of arterial $PCO_2$ in subjects at rest. J. Physiol. (Lond.) 2008 August; 586(Pt 15):3675-3682. [cited 2011 Oct. 6]
38. Somogyi R B, Vesely A E, Preiss D, Prisman E, Volgyesi G, Azami T, lscoe S, Fisher J A, Sasano H. Precise control of end-tidal carbon dioxide levels using sequential rebreathing circuits. Anaesth Intensive Care 2005 December; 33(6):726-732. [cited 2011 Oct. 6]
39. Fierstra J, Machina M, Battisti-Charbonney A, Duffin J, Fisher J A, Minkovich L. End-inspiratory rebreathing reduces the end-tidal to arterial $PCO_2$ gradient in mechanically ventilated pigs. Intensive Care Med 2011 September; 37(9):1543-1550. [cited 2011 Oct. 6]
40. Jones N L, Robertson D G, Kane J W, Campbell E J. Effect of $PCO_2$ level on alveolar-arterial $PCO_2$ difference during rebreathing. J Appl Physiol 1972 June; 32(6):782-787. [cited 2011 Oct. 6]
41. Raine J M, Bishop J M. A-a difference in $O_2$ tension and physiological dead space in normal man. J Appl Physiol 1963 March; 18:284-288. [cited 2011 Oct. 6]
42. Kelman G R. Digital computer subroutine for the conversion of oxygen tension into saturation. J Appl Physiol 1966 July; 21(4):1375-1376. [cited 2011 Oct. 6]
43. Wheeler D S, Wong H R, Shanley T P. Pediatric Critical Care Medicine: Basic Science and Clinical Evidence. 1st ed. Springer; 2007.
44. Burnett R W, Noonan D C. Calculations and correction factors used in determination of blood pH and blood gases. Clin. Chem. 1974 December; 20(12):1499-1506. [cited 2011 Oct. 6]
45. Loeppky J A, Luft U C, Fletcher E R. Quantitative description of whole blood $CO_2$ dissociation curve and Haldane effect. Respir Physiol 1983 February; 51(2):167-181. [cited 2011 Oct. 6]
46. Douglas A R, Jones N L, Reed J W. Calculation of whole blood $CO_2$ content. J. Appl. Physiol. 1988 July; 65(1):473-477. [cited 2011 Oct. 6]
47. Kelman G R. Digital computer procedure for the conversion of $PCO_2$ into blood $CO_2$ content. Respir Physiol 1967 August; 3(1):111-115. [cited 2011 Oct. 6]
48. Olszowka A J, Farhi L E. A system of digital computer subroutines for blood gas calculations. Respir Physiol 1968 March; 4(2):270-280. [cited 2011 Oct. 6]
49. Cherniack N S, Longobardo G S. Oxygen and carbon dioxide gas stores of the body. Physiol. Rev. 1970 April; 50(2):196-243. [cited 2011 Oct. 6]
50. Cherniack N S, Longobardo G S, Palermo F P, Heymann M. Dynamics of oxygen stores changes following an alteration in ventilation. J Appl Physiol 1968 June; 24(6):809-816. [cited 2011 Oct. 6]
51. Farhi L E, Rahn H. Dynamics of changes in carbon dioxide stores. Anesthesiology 1960 December; 21:604-614. [cited 2011 Oct. 6]
52. Cherniack N S, Longobardo G S, Staw I, Heymann M. Dynamics of carbon dioxide stores changes following an alteration in ventilation. J Appl Physiol 1966 May; 21(3):785-793. [cited 2011 Oct. 6]

What is claimed is:

1. An apparatus for controlling an amount of at least one gas X in a subject's lung to attain a series of targeted end tidal partial pressures of the at least one gas X ($PetX^T$), the series of targeted end tidal partial pressures of the at least one gas X ($PetX^T$) selected to stimulate a physiological response, the apparatus comprising:
   (1) a gas delivery device;
   (2) a control system for controlling the gas delivery device, wherein the control system is adapted to target a series of $PetX^T$ values for a series of respective breaths [i], the series of $PetX^T$ values comprising at least one of a set of $PetX^T$ increments and a set of $PetX^T$ decrements, the control system including means for:
   a. obtaining input of a series of logistically attainable $PetX^T$ values for the series of respective breaths [i];
   b. performing a prospective computation of an amount of gas X required to be inspired by the subject in an inspired gas to target the $PetX^T$ for a respective breath [i], the performing comprising:
      i. computing a mass balance equation including input of the concentration of gas X in the mixed venous blood entering the subject's pulmonary circulation for gas exchange in a respective breath [i] (CMVX [i]); and ii. outputting one or more values required to control the amount of gas X in a volume of gas delivered to the subject, based on the mass balance equation; and c. controlling the amount of gas X in a volume of gas delivered to the subject in a respective breath [i] to target the respective $PetX^T$ for the breath [i];

wherein at least one of a length and a number of breaths [i] in the series of respective breaths [i] is selected to show a pattern of the subject's physiological response including a dose response to the at least one of the set of $PetX^T$ increments and the set of $PetX^T$ decrements.

2. The apparatus of claim 1, wherein the at least one gas X includes carbon dioxide ($CO_2$) and wherein the physiological response is a vasodilatory response, wherein at least a set of logistically attainable $PetCO_2^T$ increments representing a desired range of a vasoactive stimulus is input in step a. to attain a series of $PetCO_2^T$ values for the series of respective breaths [i], and wherein the series of breaths [i] are selected to satisfy a condition, the condition defined by at least one of a predicted and measured attainment of at least a minimum increment in the subject's vasodilatory response to an increment in the subject's end tidal partial pressure of carbon dioxide.

3. The apparatus of claim 1, wherein the prospective computation relies on a tidal model of the lung.

4. The apparatus of claim 1, wherein the mass balance equation is computed in terms of discrete respective breaths [i] including one or more discrete volumes corresponding to a subject's functional residual capacity, anatomic dead space, a volume of gas transferred between the subject's lung and pulmonary circulation in the respective breath [i] and an individual tidal volume of the respective breath [i].

5. The apparatus of claim 1, where the physiologic response over the time course of the response is exponential, and wherein a rate of change in $PetX^T$ is selected such that three time constants in the progress of the response are achieved before a next breath [i].

6. The apparatus of claim 1, where the physiologic response over its time course is exponential, and wherein a rate of change in $PetX^T$ is selected such that three time constants in the progress of the response are achieved before a next breath [i].

7. The apparatus of claim 1, wherein the control system, in each respective breath [i], controls the delivery of at least a first inspired gas and wherein delivery of the first inspired gas is coordinated with delivery of a second inspired neutral gas, wherein a selected volume of the first inspired gas is delivered in the first part of the respective breath [i] followed by the second inspired neutral gas for the remainder of the respective breath [i], wherein volume of the first inspired gas is fixed or selected for one or more sequential breaths by way of user input so that intake of the second inspired neutral gas at least fills the entirety of the anatomic dead space.

8. The apparatus of claim 1, wherein the gas delivery device is a gas blender.

9. The apparatus of claim 1, wherein the gas X is $CO_2$.

10. The apparatus of claim 9, wherein a series of $PetCO_2$ targets provide a series of controlled vasoactive stimuli for measurement of vascular reactivity.

11. The apparatus of claim 10, wherein the series of $PetCO_2$ targets provide at least one of the following:

a) a controlled as active stimulus for measurement of cerebrovascular reactivity;

b) a controlled vasoactive stimulus for measurement of liver, kidney, heart or eye vascular reactivity;

c) a simultaneous change in the subject's end tidal partial pressures of oxygen and carbon dioxide to selected values, to potentiate a diagnosis or to treat cancer; and d) a controlled vasoactive stimulus for diagnosing steno-occlusive-disease.

12. The apparatus of claim 1, wherein a respective PetX $[i]^T$ for a series of breaths [i] increases every Nth breath in respective selected increments ("Z") from the start of the series to the end of the series (from $PetX[i^1]^T$ to $PetX[i'']^T$), wherein either N equals 1 and Z is greater than 0 in each breath in the series, or N is greater than 1 and Z may be zero in breaths which are not the Nth breath and Z is greater than 0 in every Nth breath.

13. A computer program product for use in conjunction with a gas delivery device to control an amount of at least one gas X in a subject's lung to attain a series of target end tidal partial pressure of the at least one gas X ($PetX^T$) selected to stimulate a physiological response, the computer program comprising program code for:

a. obtaining input of a series of logistically attainable end tidal partial pressure of gas X ($PetX^T$) for a respective breath [i]; and b. performing a prospective computation to obtain input of an amount of gas X required to be inspired by the subject in an inspired gas to target the $PetX_{[i]}^T$ based on the input, the performing comprising:

i. computing a mass balance equation including input of the concentration of gas X in the mixed venous blood entering the subject's pulmonary circulation for gas exchange in a respective breath [i] (CMVX [i]); and ii. outputting one or more values required to control the amount of gas X in a volume of gas delivered to the subject, based on the mass balance equation;

wherein at least one of a length and a number of breaths [i] is selected to disclose a pattern of a physiologic response to the series of targeted end tidal partial pressures of the at least one gas X.

14. A method for controlling an amount of at least one gas X in a subject's lung to attain a series of targeted end tidal partial pressures of at least one gas X ($PetX^T$), the method comprising:

a. obtaining input of a series of logistically attainable $PetX^T$ values for a series of respective breaths [i] comprising at least one of a set of $PetX^T$ increments and set of $PetX^T$ decrements; and b. performing a prospective computation of an amount of gas X required to be inspired by the subject in an inspired gas to target the respective $PetX^T$ for the breath [i], the performing comprising:

i. computing a mass balance equation including input of the concentration of gas X in the mixed venous blood entering the subject's pulmonary circulation for gas exchange in a respective breath [i] (CMVX [i]); and ii. outputting one or more values required to control the amount of gas X in a volume of gas delivered to the subject, based on the mass balance equation;

wherein at least one of a length and a number of breaths [i] in the series of respective breaths [i] is selected to disclose a pattern of a physiologic response to the series of targeted end tidal partial pressures of the at least one gas X.

15. The method of claim 14, wherein each breath [i] is a respective breath [i] and wherein a respective $PetX_{[i]}^T$ for the series of breaths [i] increases every Nth breath in respective selected increments ("Z") from the start of the series to the end of the series (from $PetX[i^1]^T$ to $PetX[i'']^T$), wherein either N equals 1 and X is greater than 0 in each breath in the series, or N is greater than 1 and Z may be zero in breaths which are not the Nth breath and Z is greater than 0 in every Nth breath.

16. The method of claim 14, wherein the physiologic response over the time course of the response is exponential, and wherein a rate of change in $PetX^T$ is selected such that two time constants in the progress of the response are achieved before a next breath [i].

17. The method of claim 14, wherein the physiologic response over the time course of the response is exponential, and wherein a rate of change in $PetX^T$ is selected such that three time constants in the progress of the response are achieved before a next breath [i].

18. The method of claim 14, wherein the gas X is $CO_2$ and wherein a series of $PetCO_2$ targets provide a series of controlled vasoactive stimuli for measurement of vascular reactivity.

19. The method of claim 14, wherein X is $CO_2$ and wherein a series of $PetCO_2$ targets provide a series of controlled vasoactive stimuli for measurement of at least one of the following:
   a) a controlled vasoactive stimuli for measurement of cerebrovascular reactivity;
   b) a controlled vasoactive stimulus for measurement of liver, kidney, heart or eye vascular reactivity;
   c) a simultaneous change in the subject's end tidal partial pressures of oxygen and carbon dioxide to selected values, for example to potentiate a diagnosis or to treat cancer; and
   d) a controlled vasoactive stimulus for diagnosing steno-occlusive-disease.

* * * * *

UNITED STATES PATENT AND TRADEMARK OFFICE
CERTIFICATE OF CORRECTION

PATENT NO. : 11,077,266 B2  
APPLICATION NO. : 15/904235  
DATED : August 3, 2021  
INVENTOR(S) : Michael Klein et al.

Page 1 of 1

It is certified that error appears in the above-identified patent and that said Letters Patent is hereby corrected as shown below:

On the Title Page

Inventors item (72) Line 9 insert --David Mikulis, Oakville (CA)--

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*